US012304963B2

(12) United States Patent
Fiori et al.

(10) Patent No.: US 12,304,963 B2
(45) Date of Patent: May 20, 2025

(54) ANTIBODY COMPLEX AND USES THEREOF

(71) Applicant: DIATHEVA S.R.L., Cartoceto (IT)

(72) Inventors: Valentina Fiori, Fano (IT); Sabrina Dominici, Fermignano (IT); Diego Moricoli, Fano (IT); Maria Elena Laguardia, Colli Al Metauro (IT); Cosimo Damiano Carbonella, Fano (IT); Maria Cristina Balducci, Fano (IT)

(73) Assignee: DIATHEVA S.R.L., Cartoceto (IT)

( * ) Notice: Subject to any disclaimer, the term of this patent is extended or adjusted under 35 U.S.C. 154(b) by 1109 days.

(21) Appl. No.: 15/734,775

(22) PCT Filed: Jun. 3, 2019

(86) PCT No.: PCT/IB2019/054571

§ 371 (c)(1),
(2) Date: Dec. 3, 2020

(87) PCT Pub. No.: WO2019/234580

PCT Pub. Date: Dec. 12, 2019

(65) Prior Publication Data

US 2021/0230292 A1 Jul. 29, 2021

(30) Foreign Application Priority Data

Jun. 4, 2018 (IT) ........................ 102018000005991
Jun. 4, 2018 (IT) ........................ 102018000005993

(51) Int. Cl.
*C07K 16/28* (2006.01)
*A61K 39/00* (2006.01)
*A61P 35/02* (2006.01)

(52) U.S. Cl.
CPC .......... *C07K 16/2896* (2013.01); *A61P 35/02* (2018.01); *A61K 2039/505* (2013.01); *C07K 2317/565* (2013.01); *C07K 2317/622* (2013.01)

(58) Field of Classification Search
CPC .......... C07K 16/2896; C07K 2317/622; C07K 2317/626
See application file for complete search history.

(56) References Cited

U.S. PATENT DOCUMENTS 8,710,194 B2 * 4/2014 Picci ....................... A61P 35/00 536/23.53
2012/0282257 A1 11/2012 Picci et al.
2016/0272720 A1 9/2016 Park et al.
2017/0029524 A1 2/2017 Liu et al.

FOREIGN PATENT DOCUMENTS

WO 2011/058517 5/2011
WO 2015/069935 5/2015
WO 2015/161267 10/2015
WO 2016/149682 9/2016
WO WO-2017144681 A1 * 8/2017 ............. A61K 35/17

OTHER PUBLICATIONS

Chiu et al., Antibodies, 8(55):1-80. (2019) (Year: 2019).*
Lichtman. The Oncologist 2017; 22(5); 542-548) (Year: 2017).*
Wan. Et al. Eur. J. Med. Chem. 2019, 183, 111691-111709) (Year: 2019).*
Rashid et. al. Eur. J. Med. Chem. 2019, 161, 205-238 (Year: 2019).*
Almagro et. al. Frontiers in Immunology. 8(1751):1-19 (Year: 2018).*
Reichert & Valge-Archer, Nat. Rev. Drug Disc. 2007; 6:349-356 (Year: 2007).*
Chan and Carter, Nature Reviews Immunology, 2010; 10:301-316 (Year: 2010).*
Blythe et al., Benchmarking B cell epitope prediction: Underperformance of existing methods, Protein Science (2005), 14:246-248 (Year: 2005).*
Schreiber et al., Wiley Interscience. 26(9):879-887 (2005) (Year: 2005).*
International Search Report issued Sep. 30, 2019 in corresponding PCT Application No. PCT/IB/2019/054571.
Written Opinion of the International Searching Authority issued Sep. 30, 2019 in corresponding PCT Application No. PCT/IB2019/054571.
Tavakkoli et al., "Do preclinical studies suggest that CD99 is a potential therapeutic target in acute myeloid leukemia and the myelodysplastic syndromes?", Expert Opinion On Therapeutic Targets, 2018, vol. 22, No. 5, pp. 381-383.
Pasello et al., "CD99 at the crossroads by physiology and pathology", Journal of Cell Communication and Signaling, 2018, vol. 12, No. 1, pp. 55-68.
Chung et al., "CD99 is a therapeutic target on disease stem cells in myeloid malignancies", Science Translational Medicine, 2017, vol. 9, No. 374, pp. 1-13.

(Continued)

*Primary Examiner* — Meera Natarajan
*Assistant Examiner* — Francesca Edgingtongiordano
(74) *Attorney, Agent, or Firm* — Wenderoth, Lind & Ponack, L.L.P.

(57) ABSTRACT

The present invention relates to a multivalent, preferably bivalent, antibody complex, more preferably a diabody, i.e. a bivalent scFv, capable of recognizing and binding the human protein CD99, a composition comprising said complex and the use thereof for diagnostic purposes and/or for the treatment and/or the follow-up of leukaemias and/or myelodysplastic syndromes. Furthermore, the present invention relates to antibodies, preferably monoclonal, of the immunoglobulins G group type capable of recognizing and binding the human protein CD99, a composition comprising said immunoglobulins and the medical use thereof, in particular for the treatment and/or the follow-up of cancer, preferably solid tumours that express CD99 and/or leukaemias and/or myelodysplastic syndromes.

17 Claims, 38 Drawing Sheets

Specification includes a Sequence Listing.

(56) References Cited

OTHER PUBLICATIONS

Manara et al., "CD99: A Cell Surface Protein with an Oncojanus Role in Tumors", Genes, 2018, vol. 9, No. 3, pp. 1-17.
Scotlandi et al., "Targeting CD99 in association with doxorubicin: An effective combined treatment for Ewing's sarcoma", European Journal of Cancer, 2006, vol. 42, No. 1, pp. 91-96.
Scotlandi et al., "CD99 Engagement: An Effective Therapeutic Strategy for Ewing Tumors", Cancer Research, AACR Annual Meeting 2017, 2000, vol. 60, No. 18, pp. 5134-5142.

* cited by examiner

A
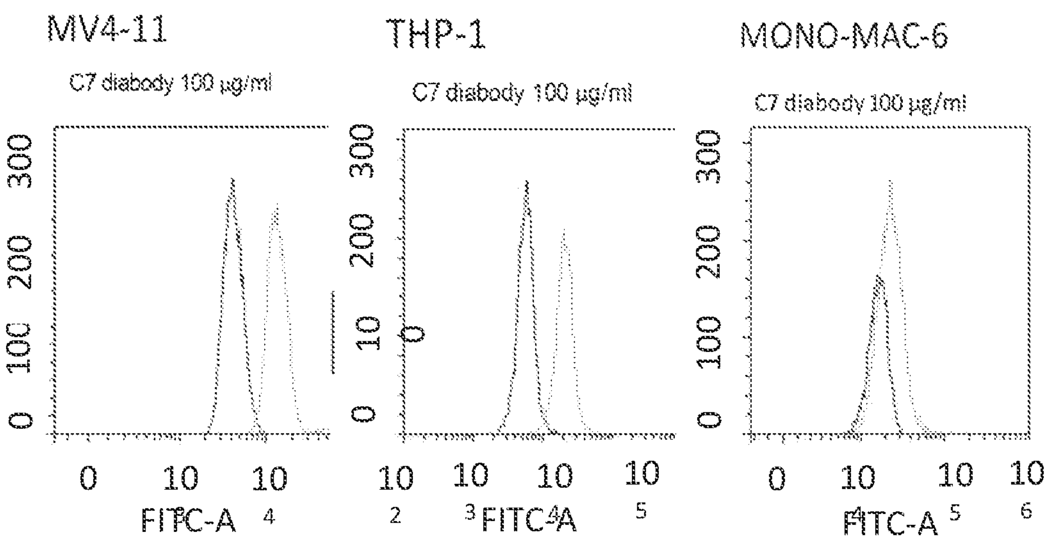
B
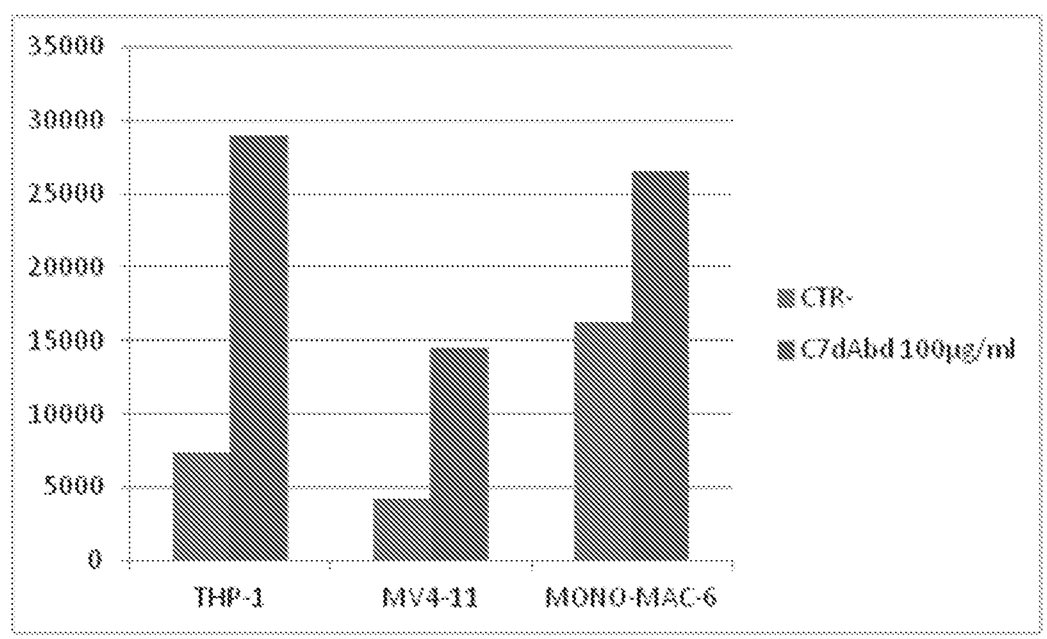
Fig. 3

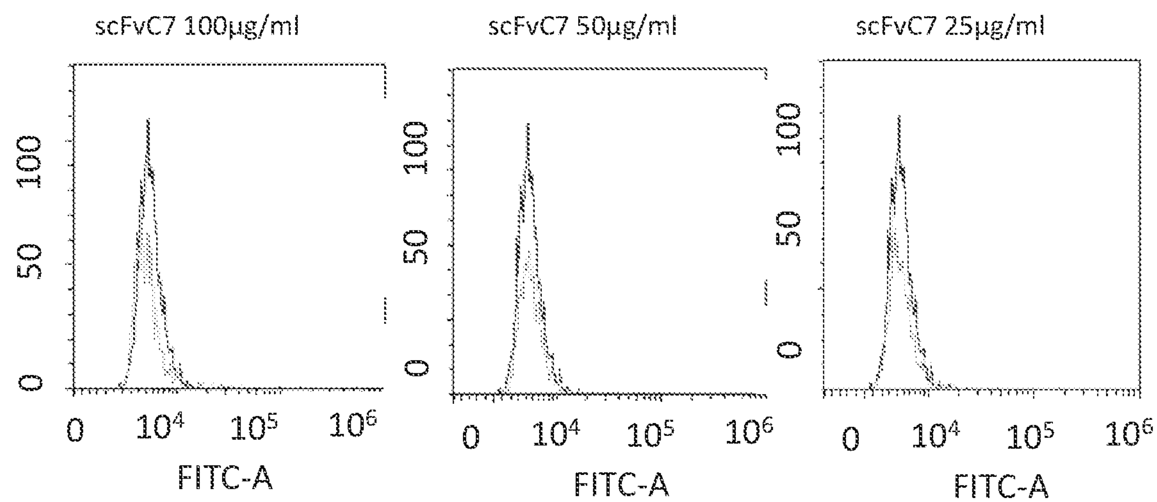
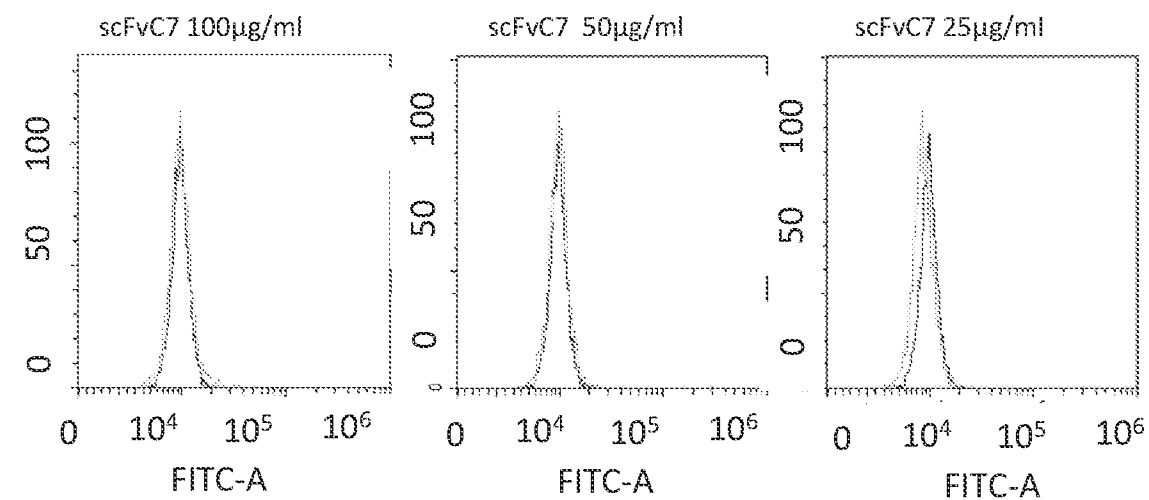
Fig. 4

A

```
man                MAAG----AALALLLFGLLGVLVA-APDGGFDLSDALPDNENKKPT---AIPKKPSAGDDFDLGDAVVDG
cynomolgus         MAAG-----AALALLLFGLLGALVA-APDDGFDLSDALPDKEGKKPT----AIPKKPSAGDDFDLGDAVVDG
green_monkey       ----------LALLLFGLLGALVA-APDDGFDLSDALPEKEDKKPT---AIPKKPSAGDDFDLGDAVVDG
mouse              MAPAAMSAAATVVLALALLGAAARGAASDDFNLGDALED-PNMKPTPKAPTPKKPSGG---FDLEDALPGG
Clustal Consensus             .:* :,***, .  *....*:*,*** :  . ***   , *****.*  *** **: .*

man                ENDDPRPPNPPKPMPNPNPNHP-GSSGSFSDADLADGVSGGEGKG---GSDG--GGSHRKEGEEAD
cynomolgus         GNDDPPPP---KPKPNPNPRQA-GSSGSFSDADLADGVSGGEGKG-----GSDG---GGSHRKEGEEAD
green_monkey       GNDDPPPPNPPKPKPNPNPRQA-GSSGSFSDADLADGVSGGEGKG----GSDG--GGSPRKEGEEAD
mouse              GGGGAGEKPGNRPQPDPKPPRPSGDSGGTSDSDLADAAGQGGGAGRRGSGDEGGSGGAGRAE-PEGT
Clustal Consensus   ....      :* *:*:* :. ..**.:**;****,.. * * *    *.:*  **: * *  *.
```

B

```
man            GDDFDLGDAVVDGENDDPRPPNPPK
cynomolgus     ............G....P..---.
green_monkey   ............G....P......
mouse          .--...E..LPG.GGGGAGEKPGNR
```

Fig. 12

A
IgG4Wt S228P IgG1
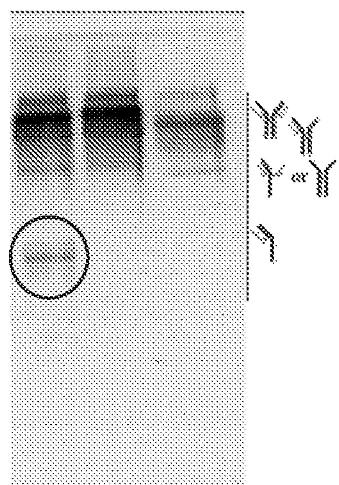
C
IgG4Wt S228P
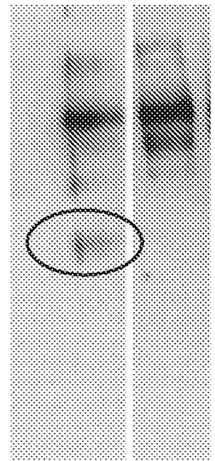
B
IgG4Wt S228P IgG1
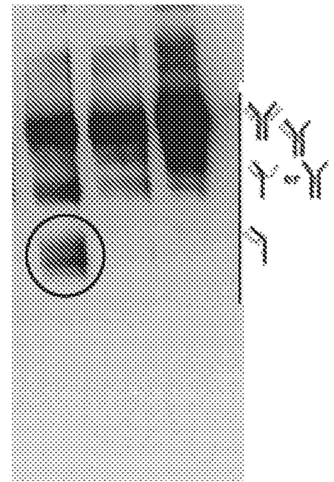
Fig. 15

A
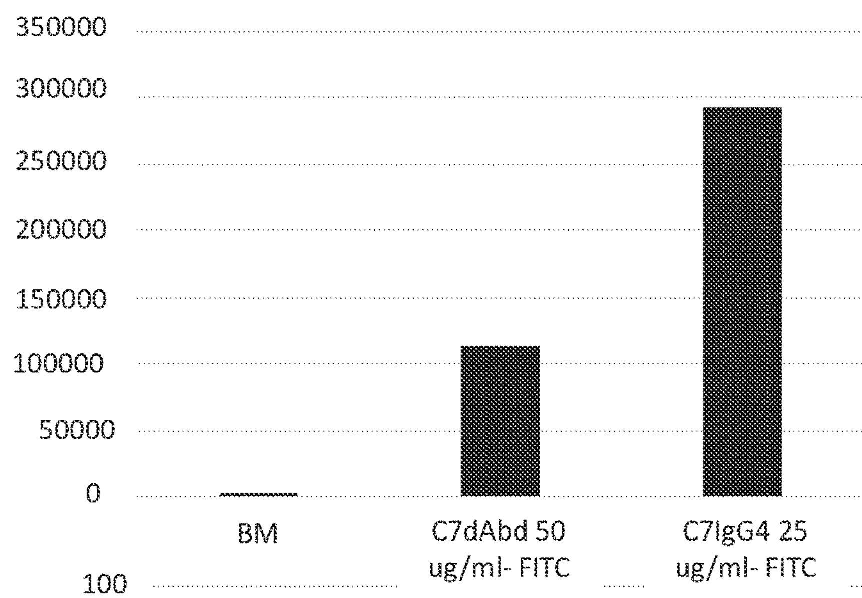
B
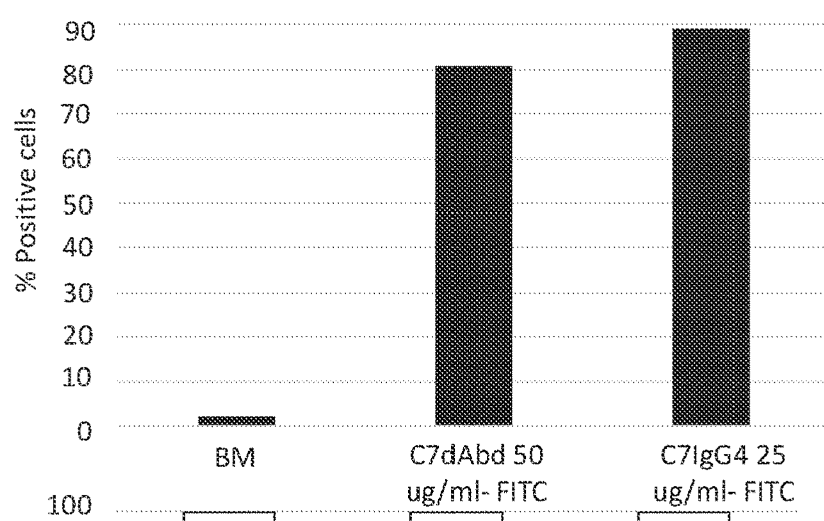
C
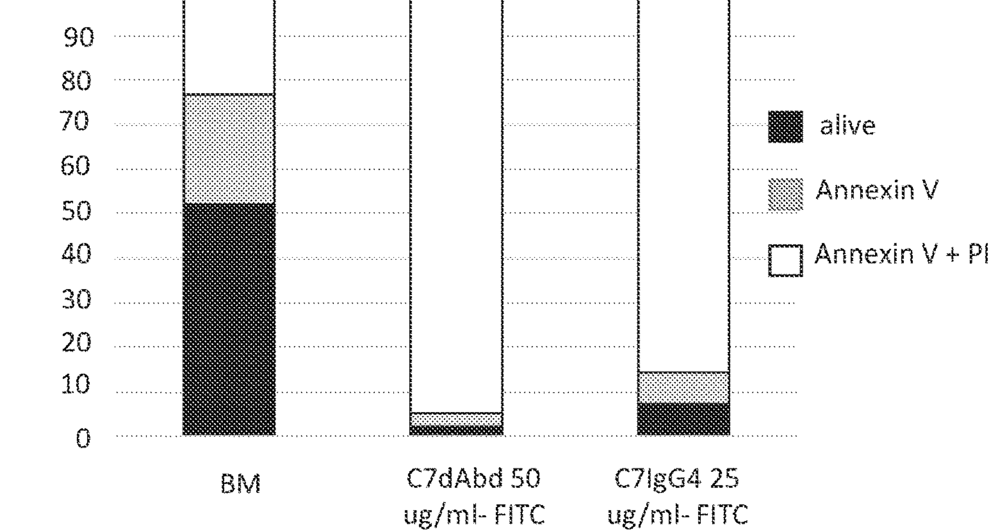
Fig. 18

C

A

B

| | % positive cells | MFI |
|---|---|---|
| CD34+ | 2.56 | 17578 |
| CD34+ CdAbdC7-FITC | 40.63 | 1479120 |

C

| | Lives | Annexin V | Annexin V+PI |
|---|---|---|---|
| CD34+ | 85.55 | 7.75 | 6.7 |
| CD34+ dAbdC7 50ug/ml | 57.89 | 35.58 | 6.53 |

A

B

| | % positive cells | MFI |
|---|---|---|
| CD34+ | 2.56 | 17578 |
| CD34+ IgG4-FITC | 23.41 | 608840 |

C

| | Lives | Annexin V | Annexin V+PI |
|---|---|---|---|
| CD34+ | 85.55 | 7.75 | 6.7 |
| CD34+ IgG4 25ug/ml | 79.69 | 11.5 | 8.81 |

Monocytes
C7IgG4 50µg/ml
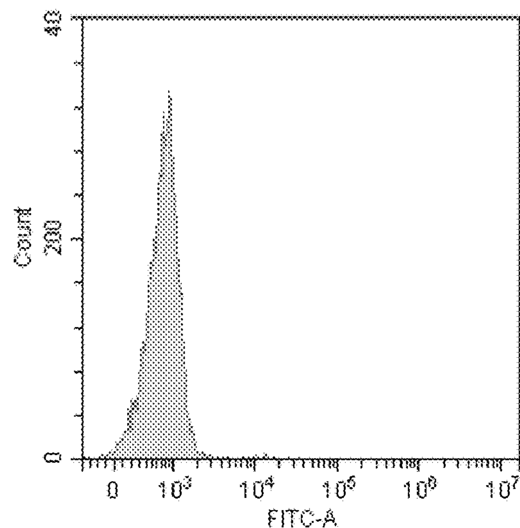
mAb 0662 5µg/ml
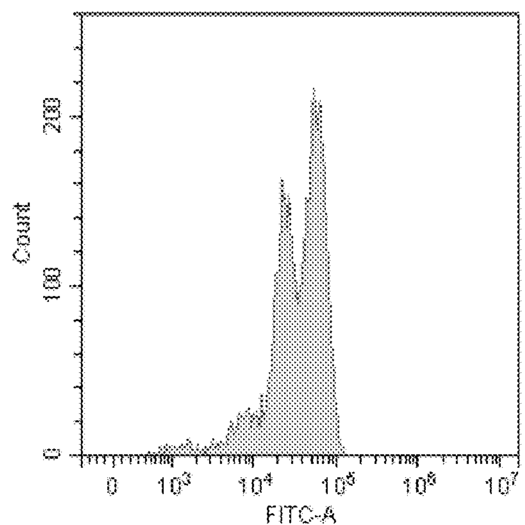
C7IgG4
25µg/ml
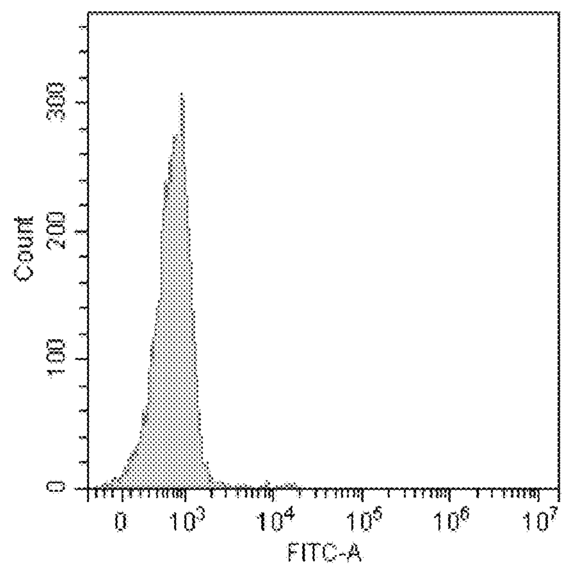
mAb 0662 2.5µg/ml
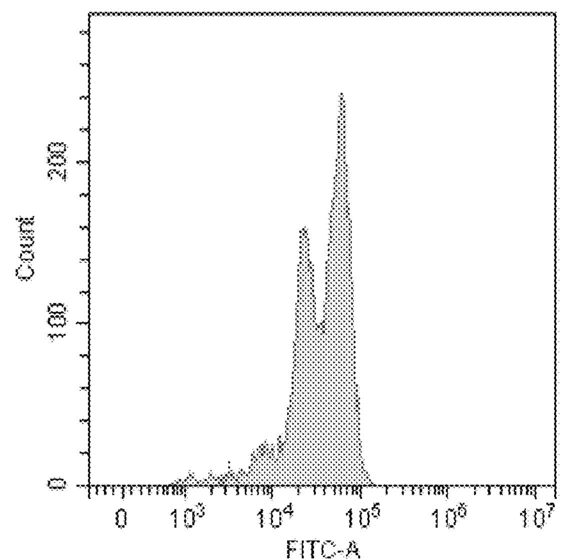
Fig. 24E

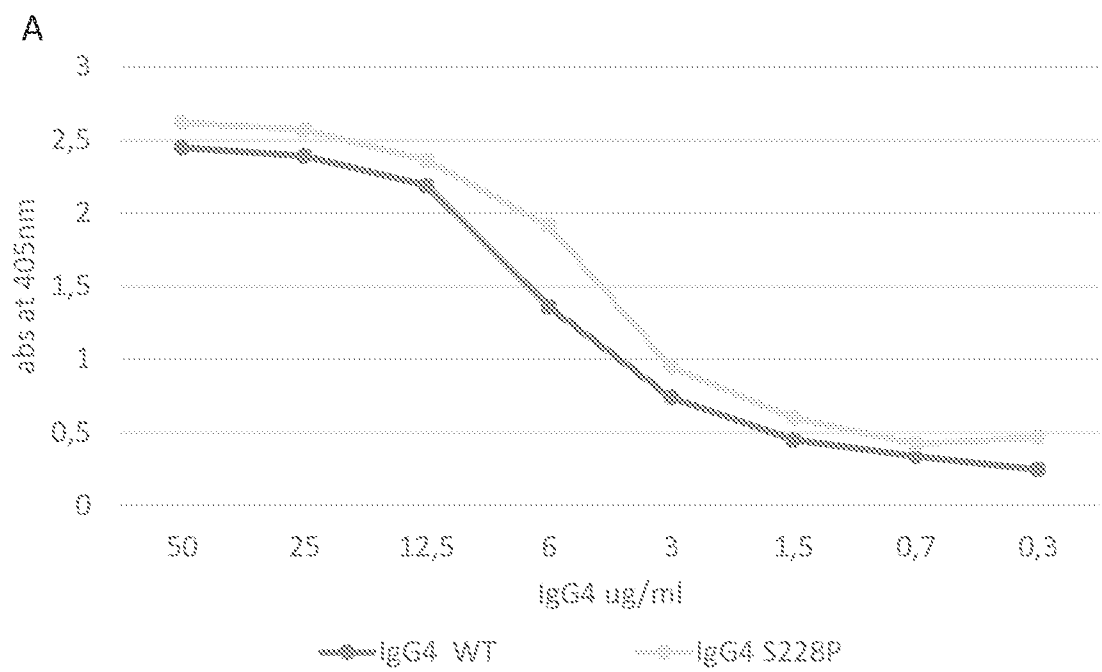
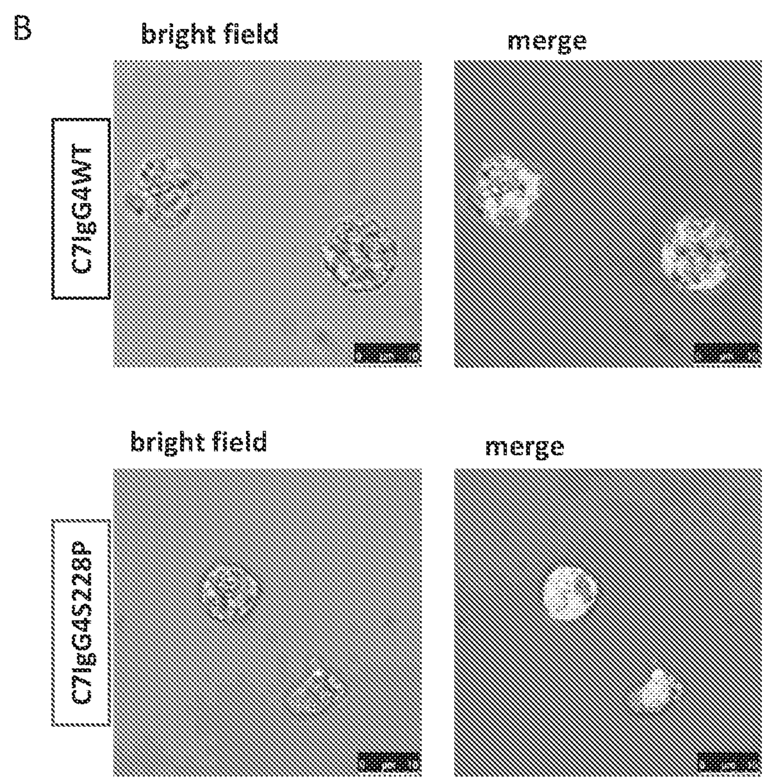
Fig. 26

SEQUENCE LISTING

```
<160> NUMBER OF SEQ ID NOS: 42

<210> SEQ ID NO 1
<211> LENGTH: 9
<212> TYPE: PRT
<213> ORGANISM: Artificial Sequence
<220> FEATURE:
<223> OTHER INFORMATION: Amino acid sequence of CDR3 of the VH chain

<400> SEQUENCE: 1

Ala Lys Ser His Lys Arg Phe Asp Tyr
1               5


<210> SEQ ID NO 2
<211> LENGTH: 11
<212> TYPE: PRT
<213> ORGANISM: Artificial Sequence
<220> FEATURE:
<223> OTHER INFORMATION: Amino acid sequence of CDR3 of the VL chain

<400> SEQUENCE: 2

Asn Ser Ser Phe Pro Arg Thr Ser Ser Val Val
1               5                   10


<210> SEQ ID NO 3
<211> LENGTH: 10
<212> TYPE: PRT
<213> ORGANISM: Artificial Sequence
<220> FEATURE:
<223> OTHER INFORMATION: Amino acid sequence of CDR1 of the VH chain

<400> SEQUENCE: 3

Gly Phe Thr Phe Ser Ser Tyr Ala Met Ser
1               5                   10
```

```
<210> SEQ ID NO 4
<211> LENGTH: 9
<212> TYPE: PRT
<213> ORGANISM: Artificial Sequence
<220> FEATURE:
<223> OTHER INFORMATION: mino acid sequence of CDR2 of the VH chain

<400> SEQUENCE: 4

Ala Ile Ser Gly Ser Gly Gly Ser Thr
1               5


<210> SEQ ID NO 5
<211> LENGTH: 11
<212> TYPE: PRT
<213> ORGANISM: Artificial Sequence
<220> FEATURE:
<223> OTHER INFORMATION: mino acid sequence of CDR1 of the VL chain

<400> SEQUENCE: 5

Gln Gly Asp Ser Leu Arg Ser Tyr Tyr Ala Ser
1               5                   10


<210> SEQ ID NO 6
<211> LENGTH: 7
<212> TYPE: PRT
<213> ORGANISM: Artificial Sequence
<220> FEATURE:
<223> OTHER INFORMATION: mino acid sequence of CDR2 of the VL chain

<400> SEQUENCE: 6

Gly Lys Asn Asn Arg Pro Ser
1               5


<210> SEQ ID NO 7
<211> LENGTH: 116
<212> TYPE: PRT
<213> ORGANISM: Artificial Sequence
<220> FEATURE:
<223> OTHER INFORMATION: Amino acid sequence of the VH chain

<400> SEQUENCE: 7

Glu Val Gln Leu Val Glu Ser Gly Gly Gly Leu Val Arg Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser His Lys Arg Phe Asp Tyr Trp Gly Gln Gly Thr Leu Val
            100                 105                 110

Thr Val Ser Arg
        115


<210> SEQ ID NO 8
<211> LENGTH: 109
<212> TYPE: PRT
<213> ORGANISM: Artificial Sequence
```

<220> FEATURE:
<223> OTHER INFORMATION: Amino acid sequence of the VL chain

<400> SEQUENCE: 8

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ser Phe Pro Arg Thr Ser Ser
                85                  90                  95

Val Val Phe Gly Gly Gly Thr Lys Leu Thr Val Leu Gly
            100                 105
```

<210> SEQ ID NO 9
<211> LENGTH: 5
<212> TYPE: PRT
<213> ORGANISM: Artificial Sequence
<220> FEATURE:
<223> OTHER INFORMATION: Amino acid sequence of the linker component unit

<400> SEQUENCE: 9

```
Gly Gly Gly Gly Ser
1               5
```

<210> SEQ ID NO 10
<211> LENGTH: 229
<212> TYPE: PRT
<213> ORGANISM: Artificial Sequence
<220> FEATURE:
<223> OTHER INFORMATION: Amino acid sequence of the scFv unit of the scFv multivalent molecule

<400> SEQUENCE: 10

```
Glu Val Gln Leu Val Glu Ser Gly Gly Gly Leu Val Arg Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser His Lys Arg Phe Asp Tyr Trp Gly Gln Gly Thr Leu Val
            100                 105                 110

Thr Val Ser Arg Gly Gly Gly Gly Ser Ser Glu Leu Thr Gln Asp Pro
        115                 120                 125

Ala Val Ser Val Ala Leu Gly Gln Thr Val Arg Ile Thr Cys Gln Gly
    130                 135                 140

Asp Ser Leu Arg Ser Tyr Tyr Ala Ser Trp Tyr Gln Gln Lys Pro Gly
```

-continued

```
145                 150                 155                 160

Gln Ala Pro Val Leu Val Ile Tyr Gly Lys Asn Asn Arg Pro Ser Gly
                165                 170                 175

Ile Pro Asp Arg Phe Ser Gly Ser Ser Ser Gly Asn Thr Ala Ser Leu
            180                 185                 190

Thr Ile Thr Gly Ala Gln Ala Glu Asp Glu Ala Asp Tyr Tyr Cys Asn
        195                 200                 205

Ser Ser Phe Pro Arg Thr Ser Ser Val Val Phe Gly Gly Gly Thr Lys
    210                 215                 220

Leu Thr Val Leu Gly
225


<210> SEQ ID NO 11
<211> LENGTH: 27
<212> TYPE: DNA
<213> ORGANISM: Artificial Sequence
<220> FEATURE:
<223> OTHER INFORMATION: Nucleotide sequence of the CDR3 of the VH chain

<400> SEQUENCE: 11

gcgaaatcgc ataagcgttt tgactac                                         27


<210> SEQ ID NO 12
<211> LENGTH: 33
<212> TYPE: DNA
<213> ORGANISM: Artificial Sequence
<220> FEATURE:
<223> OTHER INFORMATION: Nucleotide sequence of the CDR3 of the VL chain

<400> SEQUENCE: 12

aactcctctt ttccccggac ttcttctgtg gta                                  33


<210> SEQ ID NO 13
<211> LENGTH: 30
<212> TYPE: DNA
<213> ORGANISM: Artificial Sequence
<220> FEATURE:
<223> OTHER INFORMATION: Nucleotide sequence of the CDR1 of the VH chain

<400> SEQUENCE: 13

ggattcacct ttagcagcta tgccatgagc                                      30


<210> SEQ ID NO 14
<211> LENGTH: 27
<212> TYPE: DNA
<213> ORGANISM: Artificial Sequence
<220> FEATURE:
<223> OTHER INFORMATION: Nucleotide sequence of the CDR2 of the VH chain

<400> SEQUENCE: 14

gctattagtg gtagtggtgg tagcaca                                         27


<210> SEQ ID NO 15
<211> LENGTH: 33
<212> TYPE: DNA
<213> ORGANISM: Artificial Sequence
<220> FEATURE:
<223> OTHER INFORMATION: Nucleotide sequence of the CDR1 of the VL chain

<400> SEQUENCE: 15

caaggagaca gcctcagaag ctattatgca agc                                  33


<210> SEQ ID NO 16
```

<211> LENGTH: 21
<212> TYPE: DNA
<213> ORGANISM: Artificial Sequence
<220> FEATURE:
<223> OTHER INFORMATION: Nucleotide sequence of the CDR2 of the VL chain

<400> SEQUENCE: 16
ggtaaaaaca accggccctc a 21

<210> SEQ ID NO 17
<211> LENGTH: 348
<212> TYPE: DNA
<213> ORGANISM: Artificial Sequence
<220> FEATURE:
<223> OTHER INFORMATION: Nucleotide sequence of the VH chain

<400> SEQUENCE: 17
gaggtgcagc tggtggagtc tgggggaggc ttggtacggc ctggggggtc cctgagactc 60
tcctgtgcag cctctggatt cacctttagc agctatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcaaatga acagcctgag agccgaggac acggccgtat attactgtgc gaaatcgcat 300
aagcgttttg actactgggg ccagggaacc ctggtcaccg tgtcgaga 348

<210> SEQ ID NO 18
<211> LENGTH: 327
<212> TYPE: DNA
<213> ORGANISM: Artificial Sequence
<220> FEATURE:
<223> OTHER INFORMATION: Nucleotide sequence of the VL chain

<400> SEQUENCE: 18
tgctctgagc tgactcagga ccctgctgtg tctgtggcct tgggacagac agtcaggatc 60
acatgccaag gagacagcct cagaagctat tatgcaagct ggtaccagca gaagccagga 120
caggcccctg tacttgtcat ctatggtaaa aacaaccggc cctcagggat cccagaccga 180
ttctctggct ccagctcagg aaacacagct tccttgacca tcactggggc tcaggcggaa 240
gatgaggctg actattactg taactcctct tttccccgga cttcttctgt ggtattcggc 300
ggagggacca agctgaccgt cctaggc 327

<210> SEQ ID NO 19
<211> LENGTH: 15
<212> TYPE: DNA
<213> ORGANISM: Artificial Sequence
<220> FEATURE:
<223> OTHER INFORMATION: Nucleotide sequence of the component of the linker

<400> SEQUENCE: 19
ggcggtggcg gatcg 15

<210> SEQ ID NO 20
<211> LENGTH: 687
<212> TYPE: DNA
<213> ORGANISM: Artificial Sequence
<220> FEATURE:
<223> OTHER INFORMATION: Nucleotide sequence of the scFv unit of the scFv multivalent molecule

<400> SEQUENCE: 20
gaggtgcagc tggtggagtc tgggggaggc ttggtacggc ctggggggtc cctgagactc 60

```
tcctgtgcag cctctggatt cacctttagc agctatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcaaatga acagcctgag agccgaggac acggccgtat attactgtgc gaaatcgcat    300

aagcgttttg actactgggg ccagggaacc ctggtcaccg tttcgagagg cggtggcgga    360

tcgtctgagc tgactcagga ccctgctgtg tctgtggcct tgggacagac agtcaggatc    420

acatgccaag gagacagcct cagaagctat tatgcaagct ggtaccagca gaagccagga    480

caggcccctg tacttgtcat ctatggtaaa aacaaccggc cctcagggat cccagaccga    540

ttctctggct ccagctcagg aaacacagct tccttgacca tcactggggc tcaggcggaa    600

gatgaggctg actattactg taactcctct tttccccgga cttcttctgt ggtattcggc    660

ggagggacca agctgaccgt cctaggc                                        687


<210> SEQ ID NO 21
<211> LENGTH: 100
<212> TYPE: PRT
<213> ORGANISM: Artificial Sequence
<220> FEATURE:
<223> OTHER INFORMATION: Amino acid sequence of the extracellular domain
      of CD99

<400> SEQUENCE: 21

Asp Gly Gly Phe Asp Leu Ser Asp Ala Leu Pro Asp Asn Glu Asn Lys
1               5                   10                  15

Lys Pro Thr Ala Ile Pro Lys Lys Pro Ser Ala Gly Asp Asp Phe Asp
            20                  25                  30

Leu Gly Asp Ala Val Val Asp Gly Glu Asn Asp Asp Pro Arg Pro Pro
        35                  40                  45

Asn Pro Pro Lys Pro Met Pro Asn Pro Asn Pro Asn His Pro Ser Ser
    50                  55                  60

Ser Gly Ser Phe Ser Asp Ala Asp Leu Ala Asp Gly Val Ser Gly Gly
65                  70                  75                  80

Glu Gly Lys Gly Gly Ser Asp Gly Gly Gly Ser His Arg Lys Glu Gly
                85                  90                  95

Glu Glu Ala Asp
            100


<210> SEQ ID NO 22
<211> LENGTH: 300
<212> TYPE: DNA
<213> ORGANISM: Artificial Sequence
<220> FEATURE:
<223> OTHER INFORMATION: coding sequence for the extracellular domain of
      CD99

<400> SEQUENCE: 22

gatggtggtt tcgatttatc cgatgccctt cctgacaatg agaacaagaa acccactgca     60

atccccaaga aacccagtgc tggggatgac tttgacttag gagatgctgt tgttgatgga    120

gaaaatgacg acccacgacc accgaaccca cccaaaccga tgccaaatcc aaaccccaac    180

caccctagtt cctccggtag cttttcagat gctgaccttg cggatggcgt ttcaggtgga    240

gaaggaaaag gaggcagtga tggtggaggc agccacagga aagaagggga agaggccgac    300


<210> SEQ ID NO 23
<211> LENGTH: 25
```

<212> TYPE: PRT
<213> ORGANISM: Artificial Sequence
<220> FEATURE:
<223> OTHER INFORMATION: Epitope: amino acids 50-74 of the extracellular domain of CD99

<400> SEQUENCE: 23

Gly Asp Asp Phe Asp Leu Gly Asp Ala Val Val Asp Gly Glu Asn Asp
1 5 10 15

Asp Pro Arg Pro Pro Asn Pro Pro Lys
20 25

<210> SEQ ID NO 24
<211> LENGTH: 22
<212> TYPE: DNA
<213> ORGANISM: Artificial Sequence
<220> FEATURE:
<223> OTHER INFORMATION: Primer For for scFvC7 VH

<400> SEQUENCE: 24
ccagccggcc atggccgagg tg 22

<210> SEQ ID NO 25
<211> LENGTH: 30
<212> TYPE: DNA
<213> ORGANISM: Artificial Sequence
<220> FEATURE:
<223> OTHER INFORMATION: Primer Rev for scFvC7 VH

<400> SEQUENCE: 25
gtcaccgtgt cgagaggcgg tggcggatcg 30

<210> SEQ ID NO 26
<211> LENGTH: 30
<212> TYPE: DNA
<213> ORGANISM: Artificial Sequence
<220> FEATURE:
<223> OTHER INFORMATION: Primer For for scFvC7 VL

<400> SEQUENCE: 26
cgatccgcca ccgcctctcg acacggtgac 30

<210> SEQ ID NO 27
<211> LENGTH: 27
<212> TYPE: DNA
<213> ORGANISM: Artificial Sequence
<220> FEATURE:
<223> OTHER INFORMATION: Primer Rev for scFvC7 VL

<400> SEQUENCE: 27
atcgaattcc tagcctagga cggtcag 27

<210> SEQ ID NO 28
<211> LENGTH: 26
<212> TYPE: DNA
<213> ORGANISM: Artificial Sequence
<220> FEATURE:
<223> OTHER INFORMATION: Primer For CD99BamHI

<400> SEQUENCE: 28
ggaacggatc cgatggtggt ttcgat 26

<210> SEQ ID NO 29
<211> LENGTH: 28
<212> TYPE: DNA
<213> ORGANISM: Artificial Sequence -continued
<220> FEATURE:
<223> OTHER INFORMATION: Primer Rev CD99_EcoRI

<400> SEQUENCE: 29
ggctggaatt cctagtcggc ctcttccc 28

<210> SEQ ID NO 30
<211> LENGTH: 23
<212> TYPE: DNA
<213> ORGANISM: Artificial Sequence
<220> FEATURE:
<223> OTHER INFORMATION: Primer For AGM_CD99_BamHI

<400> SEQUENCE: 30
gtcgcggatc cgatgatggt ttc 23

<210> SEQ ID NO 31
<211> LENGTH: 28
<212> TYPE: DNA
<213> ORGANISM: Artificial Sequence
<220> FEATURE:
<223> OTHER INFORMATION: Primer Rev AGM_CD99_BamHI

<400> SEQUENCE: 31
atcacgaatt cctagtccgc ctcctccc 28

<210> SEQ ID NO 32
<211> LENGTH: 25
<212> TYPE: DNA
<213> ORGANISM: Artificial Sequence
<220> FEATURE:
<223> OTHER INFORMATION: Primer For mmCD99BamHI

<400> SEQUENCE: 32
ggcgcggatc cgacgacttc aacct 25

<210> SEQ ID NO 33
<211> LENGTH: 29
<212> TYPE: DNA
<213> ORGANISM: Artificial Sequence
<220> FEATURE:
<223> OTHER INFORMATION: Primer Rev mmCD99EcoRI

<400> SEQUENCE: 33
accacgaatt cctacaagcc ctggggcgt 29

<210> SEQ ID NO 34
<211> LENGTH: 443
<212> TYPE: PRT
<213> ORGANISM: Artificial Sequence
<220> FEATURE:
<223> OTHER INFORMATION: Amino acid sequence of the entire IgG4 heavy chain

<400> SEQUENCE: 34

```
Glu Val Gln Leu Val Glu Ser Gly Gly Gly Leu Val Arg Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
```

```
65                  70                  75                  80

Leu Gln Met Asn Ser Leu Arg Ala Glu Asp Thr Ala Val Tyr Tyr Cys
                85                  90                  95

Ala Lys Ser His Lys Arg Phe Asp Tyr Trp Gly Gln Gly Thr Leu Val
            100                 105                 110

Thr Val Ser Arg Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Ser
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
        435                 440


<210> SEQ ID NO 35
<211> LENGTH: 214
<212> TYPE: PRT
<213> ORGANISM: Artificial Sequence
<220> FEATURE:
<223> OTHER INFORMATION: Amino acid sequence of the entire IgG4 light
      chain
```

<400> SEQUENCE: 35

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ser Phe Pro Arg Thr Ser Ser
                85                  90                  95

Val Val Phe Gly Gly Gly Thr Lys Leu Thr Val Leu Gly Gln Pro Lys
            100                 105                 110

Ala Asn Pro Thr Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 36
<211> LENGTH: 1332
<212> TYPE: DNA
<213> ORGANISM: Artificial Sequence
<220> FEATURE:
<223> OTHER INFORMATION: Nucleotide sequence of the entire IgG4 heavy chain

<400> SEQUENCE: 36

```
gaagtgcagc tggttgagtc tggcggagga ctcgttagac ctggcggaag cctgagactg     60

tcttgtgccg ccagcggctt cacctttagc agctacgcca tgagctgggt ccgacaggct    120

cctggcaaag gccttgaatg ggtgtccgcc atctctggct ctggcggcag cacatattac    180

gccgactctg tgaagggcag attcaccatc agccgggaca acagcaagaa caccctgtac    240

ctgcagatga acagcctgag agccgaggac accgccgtgt actactgtgc caagagccac    300

aagagattcg actactgggg ccagggcacc ctggtcacag tgtctagagc ctctacaaag    360

ggccccagcg tgttccctct ggctccttgt agcagaagca ccagcgagtc tacagccgct    420

ctgggctgtc tggtcaagga ctactttccc gagcctgtga ccgtgtcctg gaatagcgga    480

gcactgacaa gcggcgtgca cacctttcca gctgtgctgc aaagcagcgg cctgtactct    540

ctgagcagcg tcgtgacagt gcctagcagc tctctgggca ccaagaccta cacctgtaat    600

gtggaccaca agcctagcaa caccaaggtg gacaagcgcg tggaatctaa gtacggccct    660

ccttgtccta gctgccccgc tcctgaattt ctcggcggac cttccgtgtt cctgtttcct    720
```

```
ccaaagccta aggacaccct gatgatcagc agaacccctg aagtgacctg cgtggtggtg    780

gacgtgtccc aagaggatcc tgaggtgcag ttcaattggt acgtggacgg cgtggaagtg    840

cacaacgcca agaccaagcc tagagaggaa cagttcaaca gcacctacag agtggtgtcc    900

gtgctgaccg tgctgcacca ggattggctg aacggcaaag agtacaagtg caaggtgtcc    960

aacaagggcc tgccaagcag catcgagaaa accatcagca aggccaaggg ccagcctagg   1020

gaaccccagg tttacacact gcctccaagc caagaggaaa tgaccaagaa ccaggtgtcc   1080

ctgacctgcc tcgtgaaggg cttctaccct tccgatatcg ccgtggaatg ggagagcaat   1140

ggccagccag agaacaacta caagacaacc cctcctgtgc tggacagcga cggctcattc   1200

ttcctgtaca gcagactgac cgtggacaag agcagatggc aagagggcaa cgtgttcagc   1260

tgcagcgtga tgcacgaggc cctgcacaac cactacaccc agaagtctct gagcctgagc   1320

ctgggcaaat ga                                                       1332
```

```
<210> SEQ ID NO 37
<211> LENGTH: 645
<212> TYPE: DNA
<213> ORGANISM: Artificial Sequence
<220> FEATURE:
<223> OTHER INFORMATION: Nucleotide sequence of the entire IgG4 light
      chain

<400> SEQUENCE: 37

tctagtgaac tgacccagga tccagccgtg tctgtggctc tgggccagac agtgcggatt     60

acctgtcagg gcgatagcct gagaagctac tacgccagct ggtatcagca gaagcctgga    120

caggctcccg tgctggtcat ctacggcaag aacaacagac ccagcggcat ccccgataga    180

ttcagcggct ctagctctgg caataccgcc agcctgacaa tcactggcgc ccaggctgaa    240

gatgaggccg actactactg caacagcagc ttccccagaa ccagcagcgt ggtgtttggc    300

ggcggaacaa agctgacagt gctgggccag cctaaggcca atcctaccgt gacactgttc    360

cctccaagca gcgaagaact gcaggccaac aaggccacac tcgtgtgcct gatcagcgac    420

ttttatcctg gcgccgtgac cgtggcctgg aaggctgatg gatctcctgt gaaagccggc    480

gtggaaacca ccaagcctag caagcagagc aacaacaaat acgccgccag cagctacctg    540

agcctgacac ctgagcagtg gaagtcccac agatcctaca gctgccaagt gacccacgag    600

ggcagcaccg tggaaaaaac agtggcccct accgagtgca gctga                    645
```

```
<210> SEQ ID NO 38
<211> LENGTH: 446
<212> TYPE: PRT
<213> ORGANISM: Artificial Sequence
<220> FEATURE:
<223> OTHER INFORMATION: Amino acid sequence of the entire IgG1 heavy
      chain

<400> SEQUENCE: 38

Glu Val Gln Leu Val Glu Ser Gly Gly Gly Leu Val Arg Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60
```

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser His Lys Arg Phe Asp Tyr Trp Gly Gln Gly Thr Leu Val
            100                 105                 110

Thr Val Ser Arg Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 39
<211> LENGTH: 214
<212> TYPE: PRT
<213> ORGANISM: Artificial Sequence
<220> FEATURE:
<223> OTHER INFORMATION: Amino acid sequence of the entire IgG1 light

```
      chain

<400> SEQUENCE: 39

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ser Phe Pro Arg Thr Ser Ser
                85                  90                  95

Val Val Phe Gly Gly Gly Thr Lys Leu Thr Val Leu Gly Gln Pro Lys
            100                 105                 110

Ala Asn Pro Thr Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210


<210> SEQ ID NO 40
<211> LENGTH: 1338
<212> TYPE: DNA
<213> ORGANISM: Artificial Sequence
<220> FEATURE:
<223> OTHER INFORMATION: Nucleotide sequence of the entire IgG1 heavy
      chain

<400> SEQUENCE: 40

gaagtgcagc tggttgagtc tggcggagga ctcgttagac ctggcggaag cctgagactg      60

tcttgtgccg ccagcggctt cacctttagc agctacgcca tgagctgggt ccgacaggct     120

cctggcaaag gccttgaatg ggtgtccgcc atctctggct ctggcggcag cacatattac     180

gccgactctg tgaagggcag attcaccatc agccgggaca acagcaagaa caccctgtac     240

ctgcagatga acagcctgag agccgaggac accgccgtgt actactgtgc caagagccac     300

aagagattcg actactgggg ccagggcacc ctggtcacag tgtctagagc cagcaccaag     360

ggcccttccg tgtttccact ggcccctcc tctaaatcca catctggcgg caccgccgcc      420

ctgggctgtc tggtgaagga ctacttccca gagcctgtga cagtgtcctg gaactctggc     480

gccctgacat ccggcgtgca cacatttcca gccgtgctgc agagctccgg cctgtacagc     540

ctgtctagcg tggtgacagt gccctcctct agcctgggca cacagaccta tatctgcaac     600

gtgaatcaca agccaagcaa taccaaggtg gacaagaagg tggagcccaa gtcctgtgat     660
```

```
aagacacaca cctgcccccc ttgtcctgct cccgagctgc tgggcggccc tagcgtgttc    720

ctgtttccac ccaagcctaa ggacaccctg atgatctccc ggacacccga ggtgacctgc    780

gtggtggtgg acgtgtctca cgaggatcct gaggtgaagt tcaactggta tgtggatggc    840

gtggaggtgc acaatgccaa gaccaagccc agagaggagc agtacaactc tacatatagg    900

gtggtgagcg tgctgaccgt gctgcaccag gactggctga acggcaagga gtataagtgc    960

aaggtgtcca ataaggccct gcccgccccc atcgagaaga caatcagcaa ggccaagggc   1020

cagcctcggg agccacaggt gtacaccctg cctccatcca gagacgagct gacaaagaac   1080

caggtgtctc tgacatgtct ggtgaagggc ttctatccta gcgatatcgc cgtggagtgg   1140

gagtccaatg gccagccaga gaacaattac aagaccacac cccctgtgct ggactccgat   1200

ggctccttct ttctgtattc caagctgacc gtggataagt ctcggtggca gcagggcaac   1260

gtgttcagct gttccgtgat gcacgaagcc ctgcataatc actatactca gaaatccctg   1320

tccctgtcac ctggaaag                                                 1338


<210> SEQ ID NO 41
<211> LENGTH: 642
<212> TYPE: DNA
<213> ORGANISM: Artificial Sequence
<220> FEATURE:
<223> OTHER INFORMATION: Nucleotide sequence of the entire IgG1 light
      chain

<400> SEQUENCE: 41

tctagtgaac tgacccagga tccagccgtg tctgtggctc tgggccagac agtgcggatt     60

acctgtcagg gcgatagcct gagaagctac tacgccagct ggtatcagca gaagcctgga    120

caggctcccg tgctggtcat ctacggcaag aacaacagac ccagcggcat ccccgataga    180

ttcagcggct ctagctctgg caataccgcc agcctgacaa tcactggcgc ccaggctgaa    240

gatgaggccg actactactg caacagcagc ttccccagaa ccagcagcgt ggtgtttggc    300

ggcggaacaa agctgacagt gctgggccag cctaaggcca atcctaccgt gacactgttc    360

cctccaagca gcgaagaact gcaggccaac aaggccacac tcgtgtgcct gatcagcgac    420

ttttatcctg gcgccgtgac cgtggcctgg aaggctgatg gatctcctgt gaaagccggc    480

gtggaaacca ccaagcctag caagcagagc aacaacaaat acgccgccag cagctacctg    540

agcctgacac ctgagcagtg gaagtcccac agatcctaca gctgccaagt gacccacgag    600

ggcagcaccg tggaaaaaac agtggcccct accgagtgca gc                       642


<210> SEQ ID NO 42
<211> LENGTH: 443
<212> TYPE: PRT
<213> ORGANISM: Artificial Sequence
<220> FEATURE:
<223> OTHER INFORMATION: Nucleotide sequence of the entire IgG4 heavy
      chain mutated in S228P

<400> SEQUENCE: 42

Glu Val Gln Leu Val Glu Ser Gly Gly Gly Leu Val Arg Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60
```

-continued

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser His Lys Arg Phe Asp Tyr Trp Gly Gln Gly Thr Leu Val
            100                 105                 110

Thr Val Ser Arg Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
        435                 440
```

ANTIBODY COMPLEX AND USES THEREOF

TECHNICAL FIELD

The present invention relates to a multivalent, preferably bivalent, antibody complex, more preferably a diabody, i.e. a bivalent scFv, capable of recognizing and binding the human protein CD99, a composition comprising said complex and the use thereof for diagnostic purposes and/or for the treatment and/or the follow-up of leukaemias and/or myelodysplastic syndromes.

Furthermore, the present invention relates to antibodies, preferably monoclonal, of the immunoglobulins G group type, capable of recognizing and binding the human protein CD99, a composition comprising said immunoglobulins and the medical use thereof, in particular for the treatment and/or the follow-up of cancer, preferably solid tumours expressing CD99 and/or leukaemias and/or myelodysplastic syndromes.

STATE OF THE ART

It is well known that cancer represents one of the main causes of death worldwide.

Furthermore, it has a large impact on the social life and health costs of every country. The efforts to find therapies capable of alleviating or curing cancer are considerable and come from every direction.

Leukaemias are among the most common forms of cancer.

Leukaemia is a term indicating a set of malignant diseases, various types of cancer or tumours, characterized by a neoplastic proliferation of haemopoietic stem cells, and it results in a high number of abnormal white blood cells. These white blood cells are not fully developed and are called blasts or leukaemia cells.

Haemopoietic stem cells, which are to be found in red bone marrow, give rise to two cell lines:

The myeloid line, from which red blood cells, some types of white blood cells (granulocytes and monocytes) and platelets originate;

The lymphoid line, from which lymphocytes (another type of white blood cells) originate.

Depending on the cell line the leukaemic clone evolves towards, one speaks of acute lymphoblastic leukaemia (ALL), acute myeloid leukaemia (AML), chronic lymphatic leukaemia (CLL) and chronic myeloid leukaemia (CML).

The exact cause of the condition is as of yet unknown. Various factors, both genetic and environmental, are considered to be possible risk factors, including smoking, exposure to ionising radiations or to some chemical substances (such as benzene), previous chemotherapy treatments and Down's syndrome.

Myelodysplastic syndromes (MDSs) are a group of blood diseases characterized by a defect in the bone marrow, which is no longer able to produce several blood cell lines, such as red blood cells, white blood cells and platelets, in a sufficient number. MDSs are also called pre-leukaemic diseases, because over time they may evolve into an acute form of leukaemia.

The diagnosis is usually formulated thanks to a blood test or by means of a bone marrow biopsy.

The treatment of leukaemia entails a combination of chemotherapy, radiotherapy, targeted therapy, and bone marrow transplant, in addition to support therapy and possibly palliative treatments. The transplant of haemopoietic stem cells to replace diseased cells destroyed with high doses of chemo- or radiotherapy with healthy ones from a compatible donor, often a sibling or family member, but sometimes also an unknown individual, is able to cure the disease permanently in some cases, especially in younger patients, and can be used for forms that no longer respond to chemotherapy. There are also therapies which stimulate the immune system to recognize and destroy leukaemia cells. In some types of leukaemia use is made, for example, of interferon to slow the growth of tumour cells.

The forerunner of targeted therapies for leukaemia is Imatinib, a tyrosine kinase inhibitor used for the treatment of CML and ALL and characterized by the presence of the anomalous Bcr-Abl protein, produced as a result of a chromosome translocation which originates the so-called Philadelphia (Ph+) chromosome. The therapy is highly effective, even though a form of resistance may arise over the years.

Notwithstanding the recent progress in the development of new treatments for leukaemias, the average five-year survival rate in the United States is 57%. In children under 15, the five-year survival rate is higher than 60% and 85%, depending on type. Therefore, there is a strongly felt need to identify improved or alternative therapies/molecules to be used, individually or also in combination with the currently available therapies, for the treatment of tumours in general and leukaemias in particular. Recent studies have shown that membrane proteins can have an altered expression in leukaemic haematopoietic cells.

In particular, Pasello et al., in J. Of Cell Communication and Signaling (2018) 12:55-68, describe that the membrane glycoprotein CD99 is overexpressed in various types of tumours, including leukaemias.

WO2016149682 describes anti-CD99 antibodies and demonstrates how the induction of cell death does not necessarily follow antigen-antibody bonding.

WO2011058517 describes an anti-CD99 scFV. Monomeric units of the same scFv have shown to be effective for treating Ewing's sarcoma. However, it is not capable of recognizing and binding leukaemia cells such as JURKAT, CCRF-CEM, HL-60 and MOLT-4.

The authors of the present invention have found the use of a multivalent antibody complex capable of recognizing and binding the human protein CD99 as a solution to the above-mentioned needs. In particular, they have found that a diabody, i.e. two units of a single-chain variable fragment (scFv), directed against CD99 is particularly effective in the treatment and/or the follow-up of leukaemias and/or myelodysplastic syndromes.

Furthermore, the authors of the present invention have also surprisingly found that antibodies, preferably monoclonal, of the immunoglobulins G group type capable of recognizing and binding the human protein CD99, are effective for the therapeutic treatment of various types of cancer, in particular solid tumours expressing CD99, leukaemias and/or myelodysplastic syndromes. Class IgG4 and IgG1 monoclonal antibodies have shown to be particularly effective.

In fact, the authors have found that leukaemia cells undergo death following binding with the diabody and/or IgG forms of the antibody complex described herein. In particular, by means of confocal microscopy, the authors of the present invention have found that leukaemia cells are capable of internalizing the antibody complex described herein. This latter data is particularly interesting and advantageous because it allows the use of the complex in applications that require the internalization of the antibody, as in the case of antibody-drug conjugates (ADCs).

BRIEF DESCRIPTION OF THE DRAWINGS

Further advantages of the present invention will be apparent from the following detailed description and the appended figures, in particular:

BRIEF DESCRIPTION OF THE DRAWINGS

Figure 1:
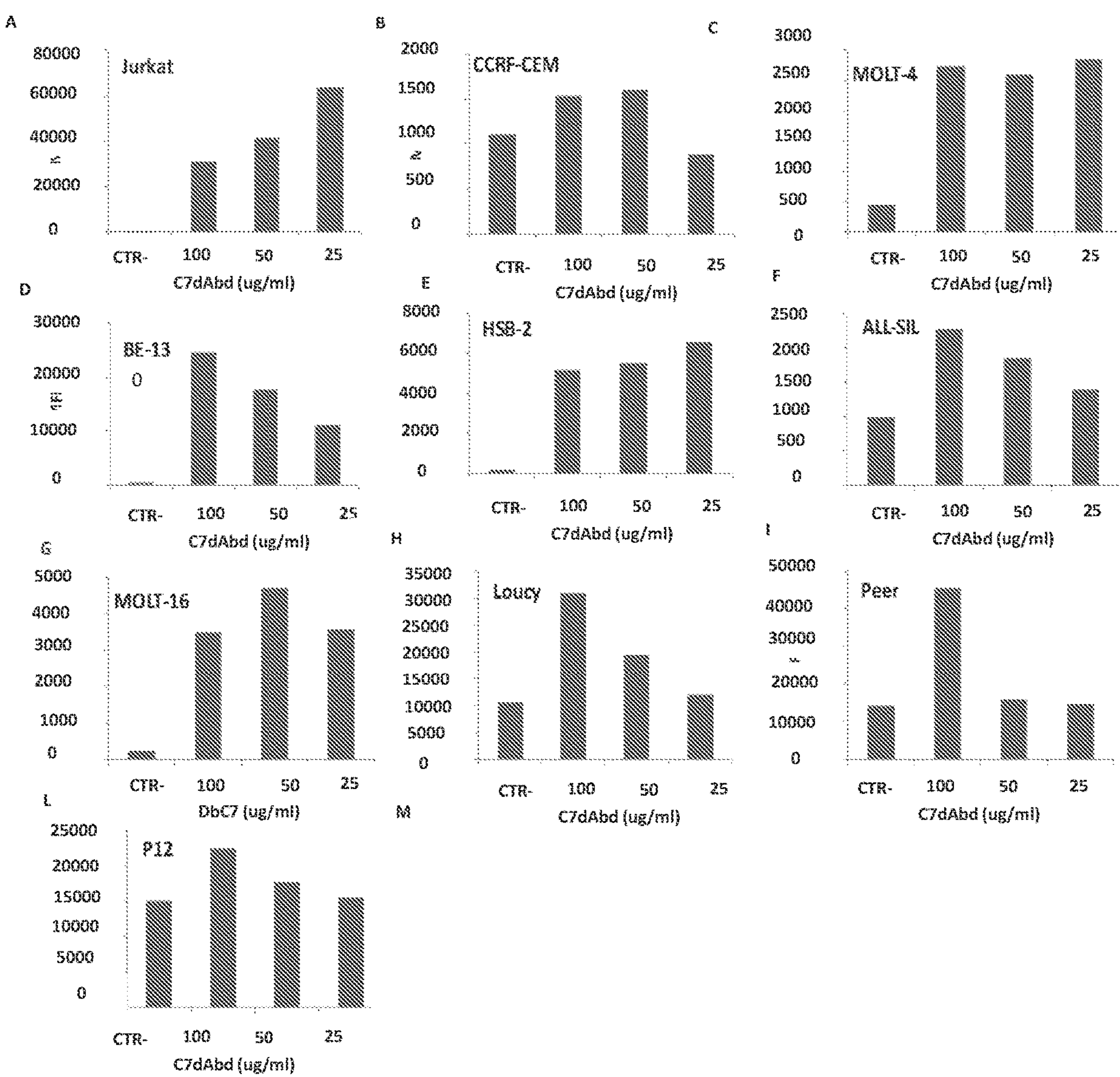

Further advantages of the present invention will be apparent from the following detailed description and the appended figures, in particular:

FIG. 1 shows the results of a cytofluorometric analysis of leukaemia cell lines (A) Jurkat, (B) CCRF-CEM, (C) MOLT-4, (D) BE-13, (E) HSB-2, (F) ALL-SIL, (G) MOLT-16, (H) Laucy, (I) Peer, and (L) P12, following treatment with example embodiments of the antibody complex of the invention (diabody).

Figure 2:
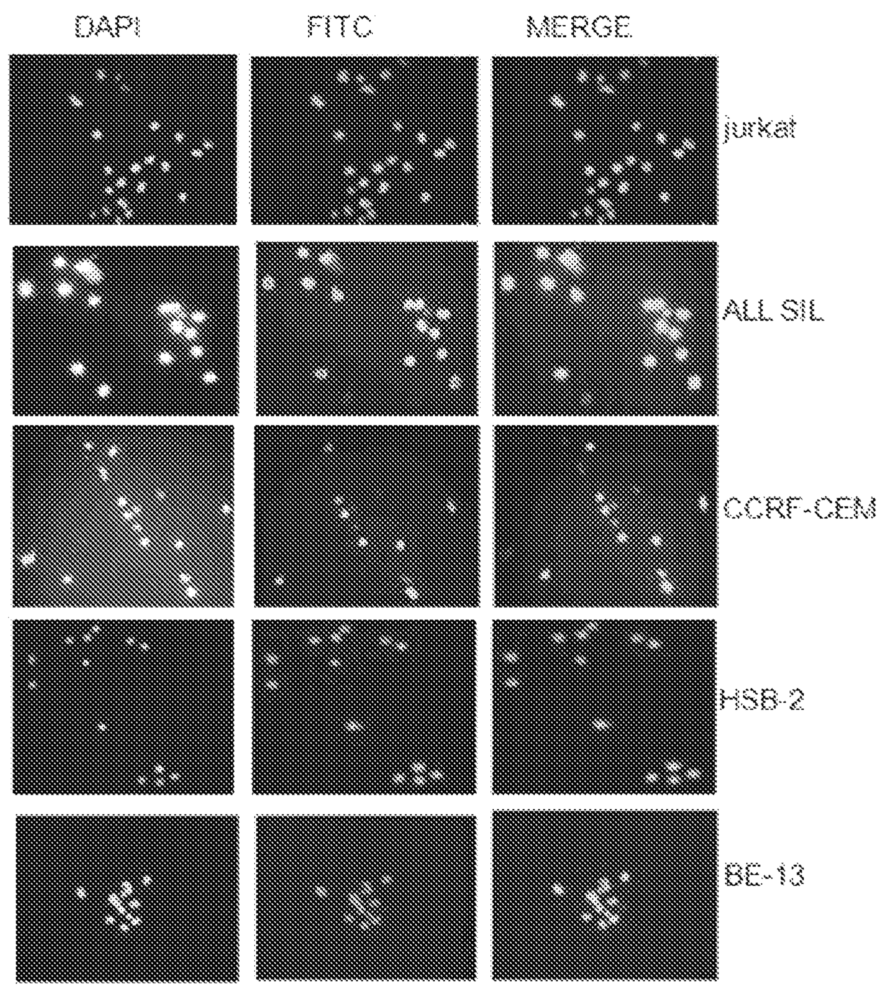

FIG. 2 shows a fluorescence microscopy analysis of leukaemia cells treated with example embodiments of the antibody complex of the invention (diabody).

FIG. 3 shows the results of a reactivity analysis of some example embodiments of the antibody complex of the invention (diabody) with cell lines of acute myeloid leukaemia. (A) cytofluorometry; (B) cell activity. The peak delineated by the dark line represents the peak of the cells marked only with the secondary antibody, whereas the peak delineated by the light grey line represents the cells marked with the diabody form of the complex.

FIG. 4 shows the results of an analysis of the reactivity of the monomer scFv C7 with cell lines of acute myeloid and lymphoid leukaemia. The peak delineated by the dark line represents the peak of the cells marked only with the secondary antibody, whereas the peak delineated by the light grey line represents the cells marked with the monomer scFv C7.

Figure 5:
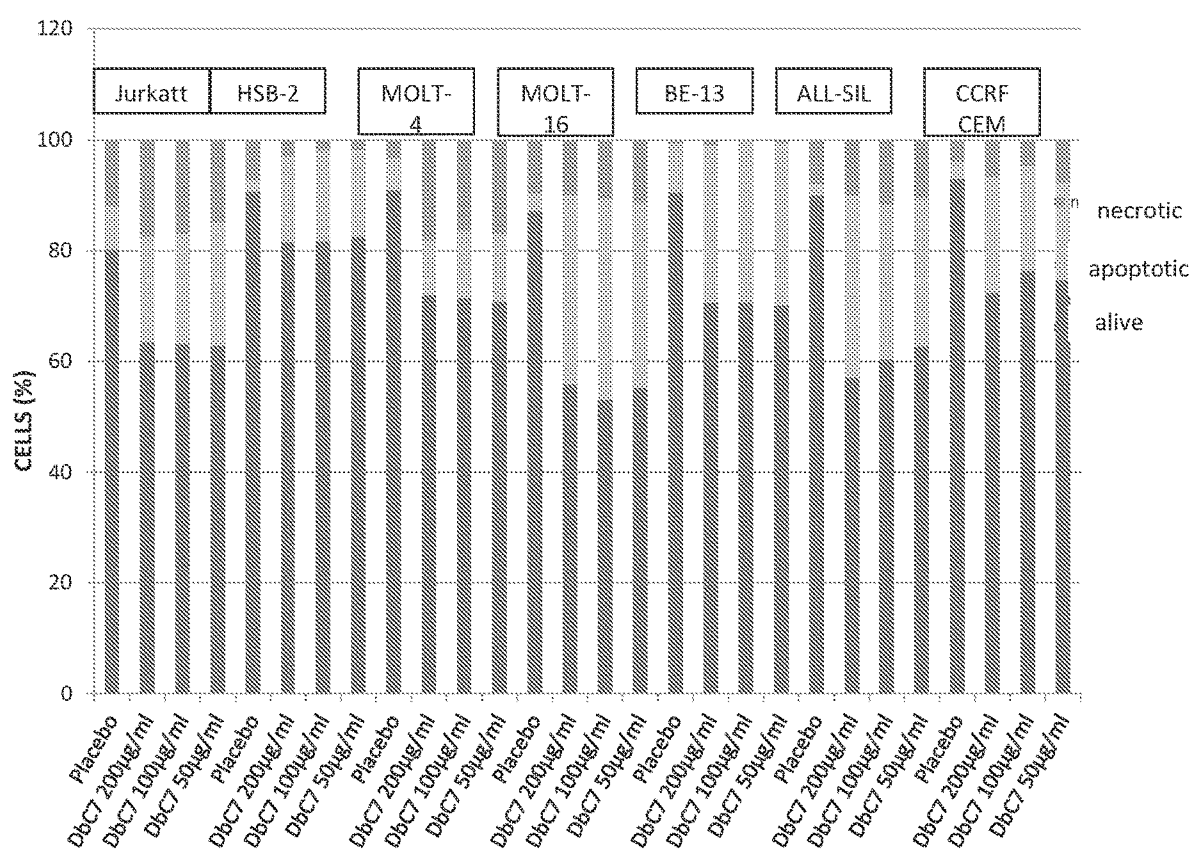

FIG. 5 shows the results of an analysis of leukaemia cell death induced by some example embodiments of the antibody complex of the invention (diabody), measured by cytofluorometry.

Figure 6:
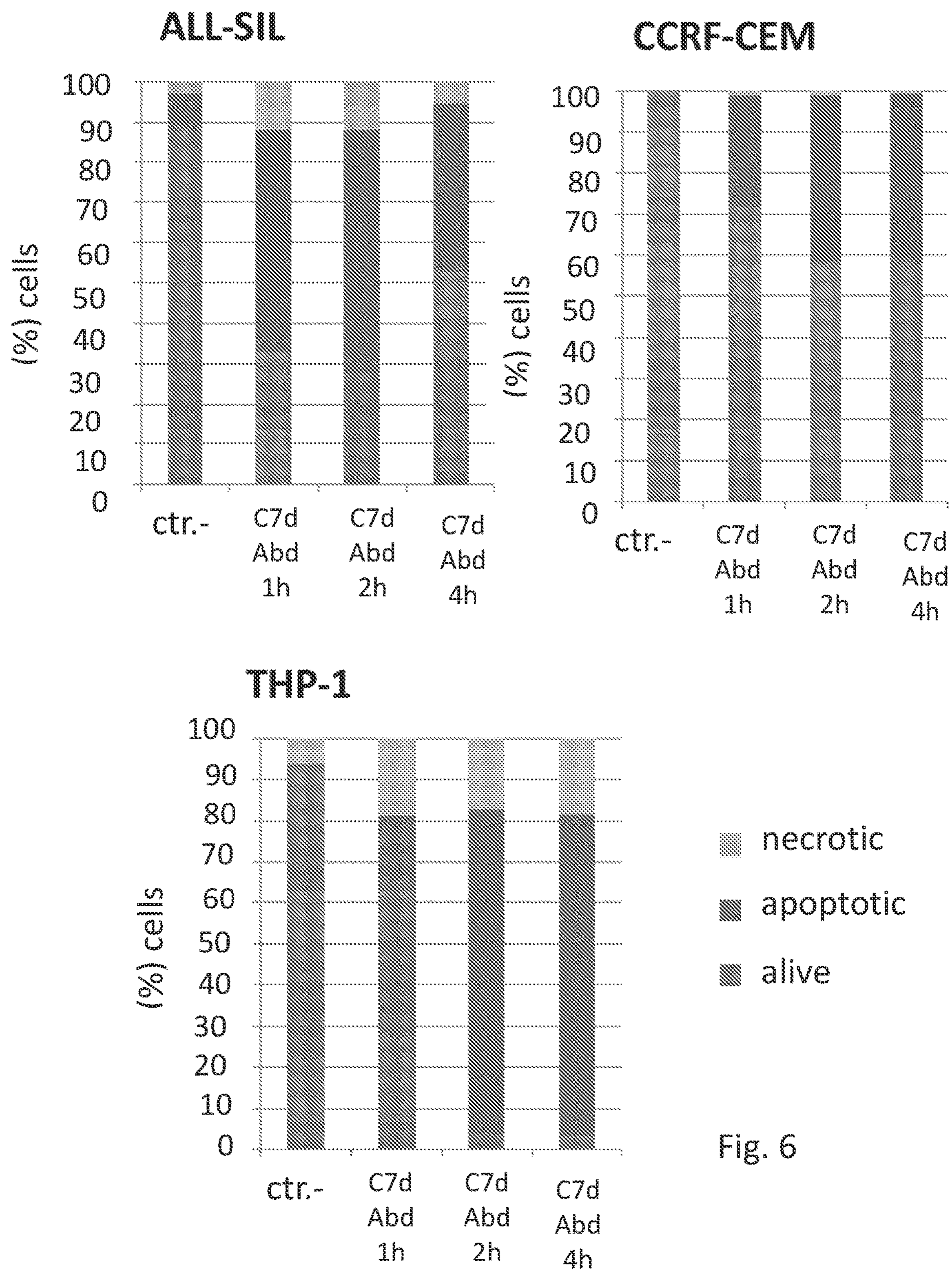

FIG. 6 shows the results of an analysis of leukaemia cell death induced by some example embodiments of the antibody complex of the invention (diabody) measured by cytofluorometry.

Figure 7:
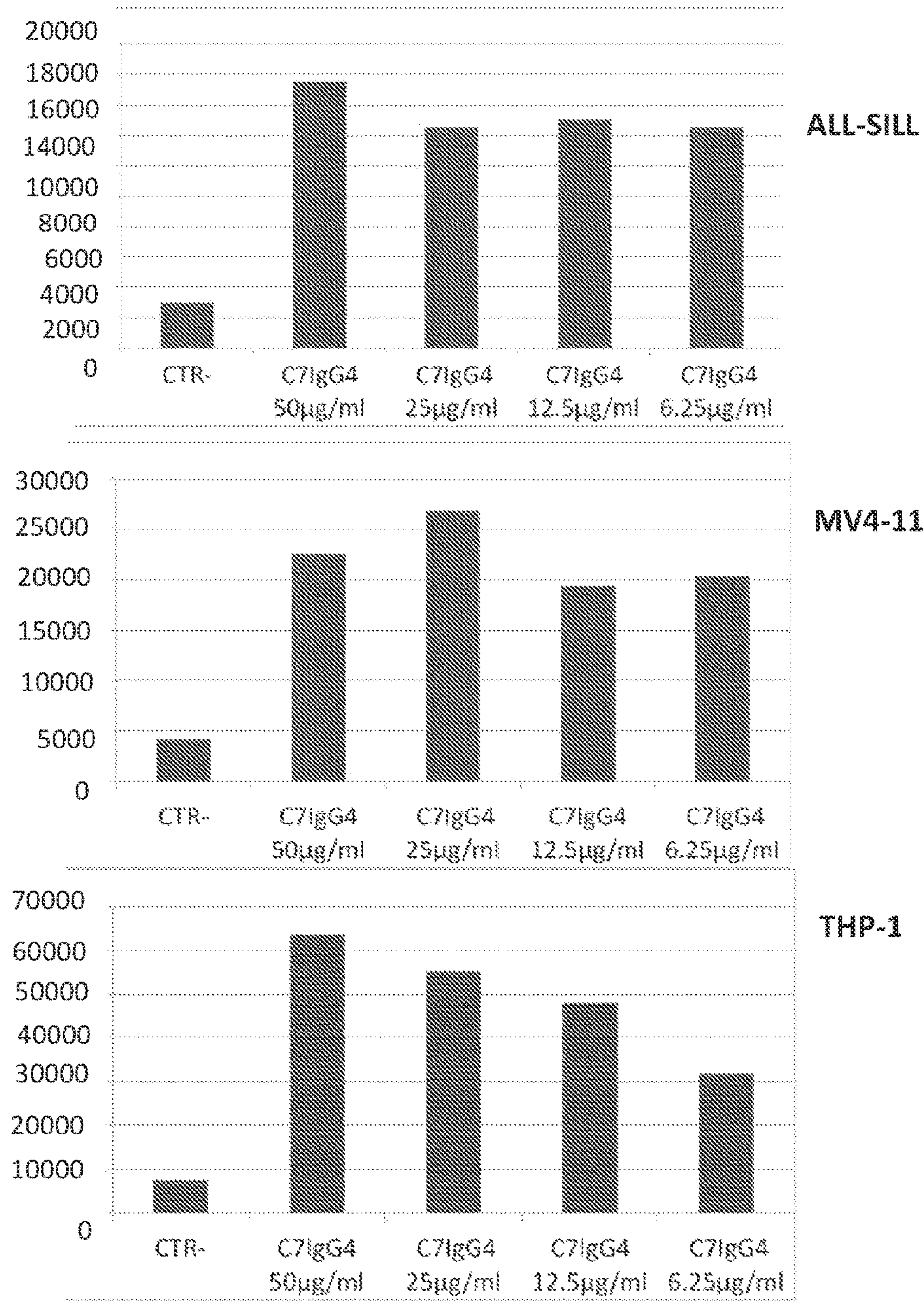
Figure 8:
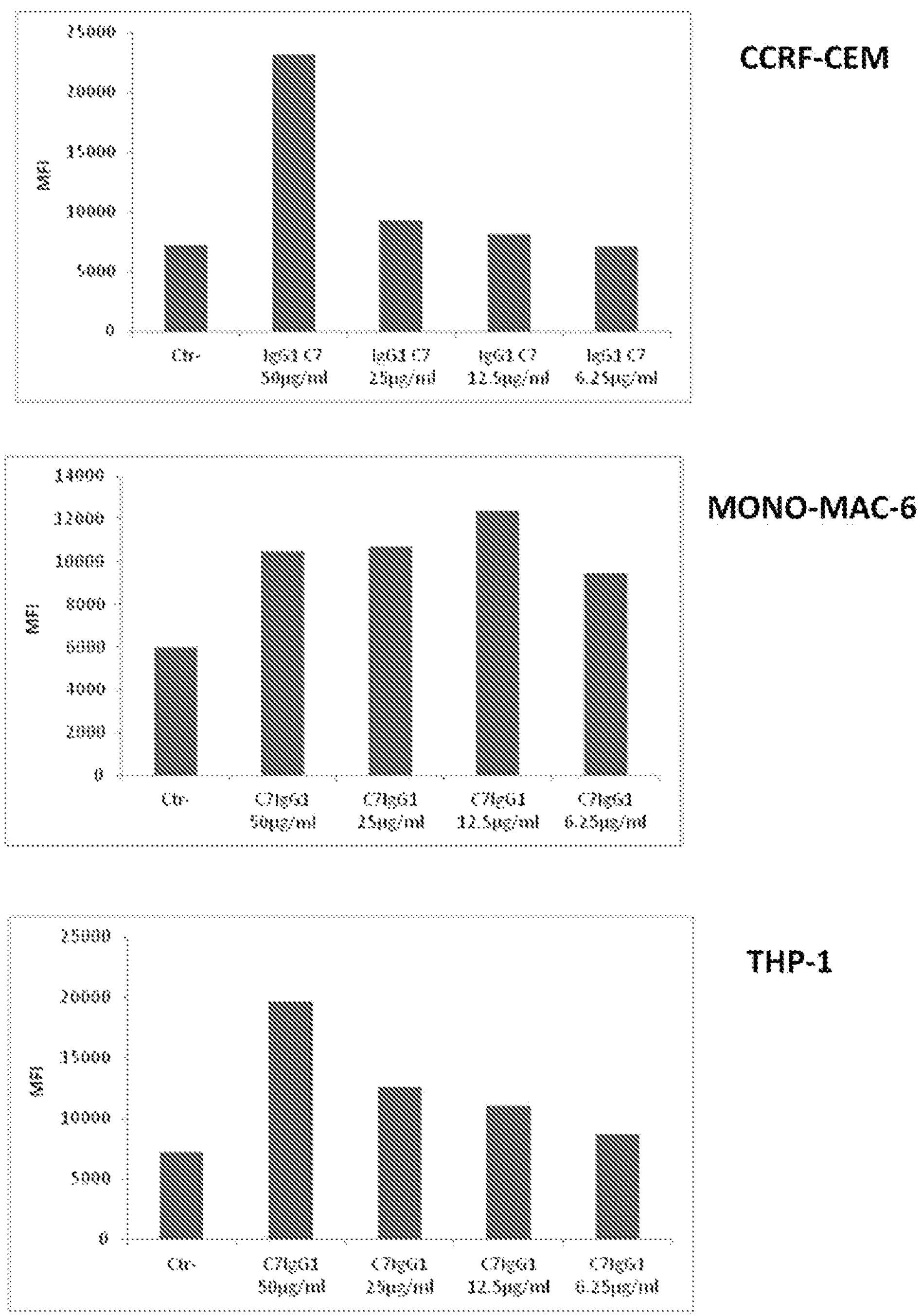

FIGS. 7 and 8 show the results of a cytofluorometric analysis of reactivity of some example embodiments of the antibody complex of the invention (antibodies in the form of IgG1 and IgG4, i.e. C7IgG1 and C7IgG4) obtained in the following cell lines: T-ALL: ALL-SIL, CCRF-CEM and of AML: MV4-11, THP-1 and MONO-MAC-6.

Figure 9:
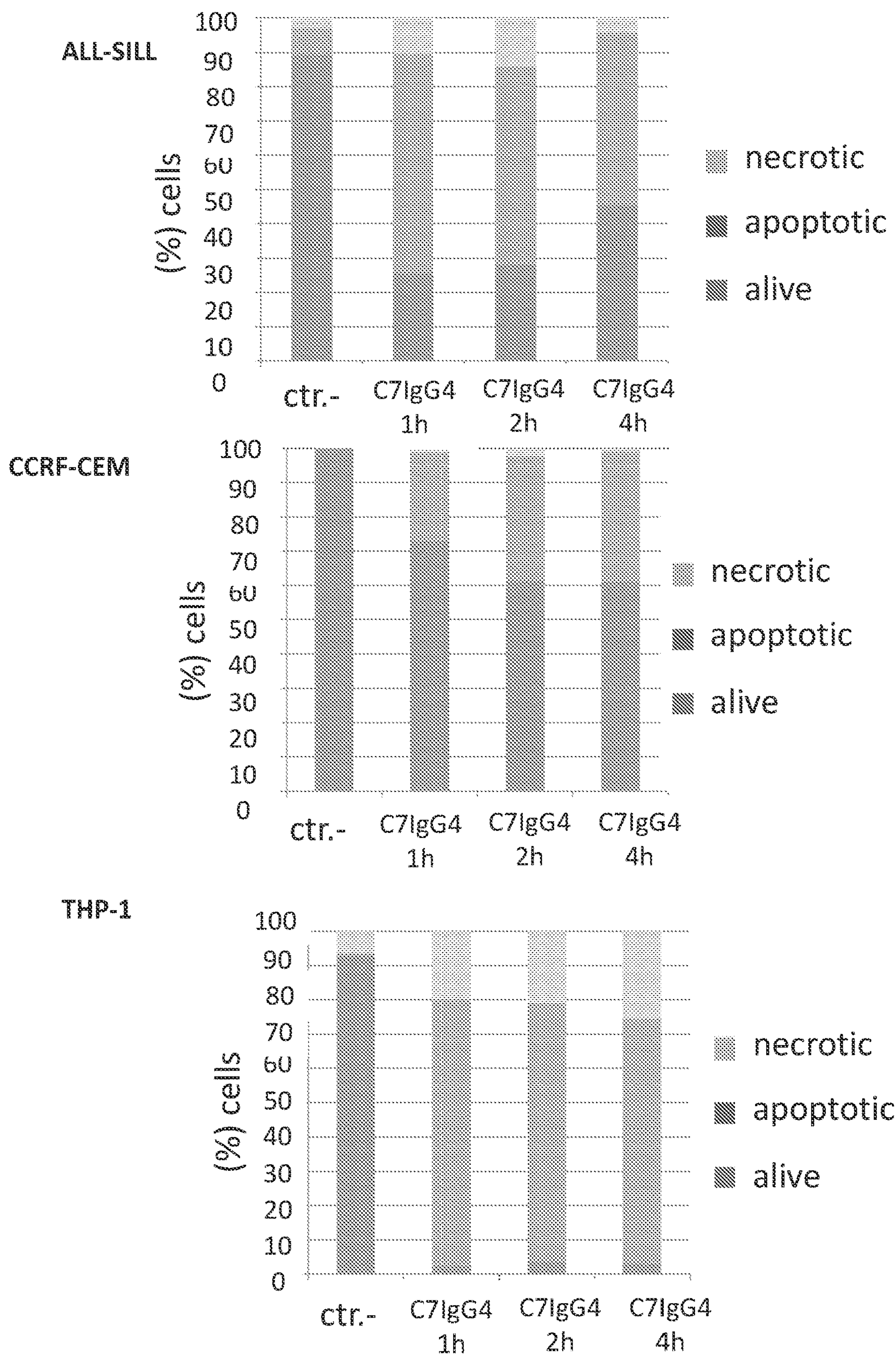
Figure 10:
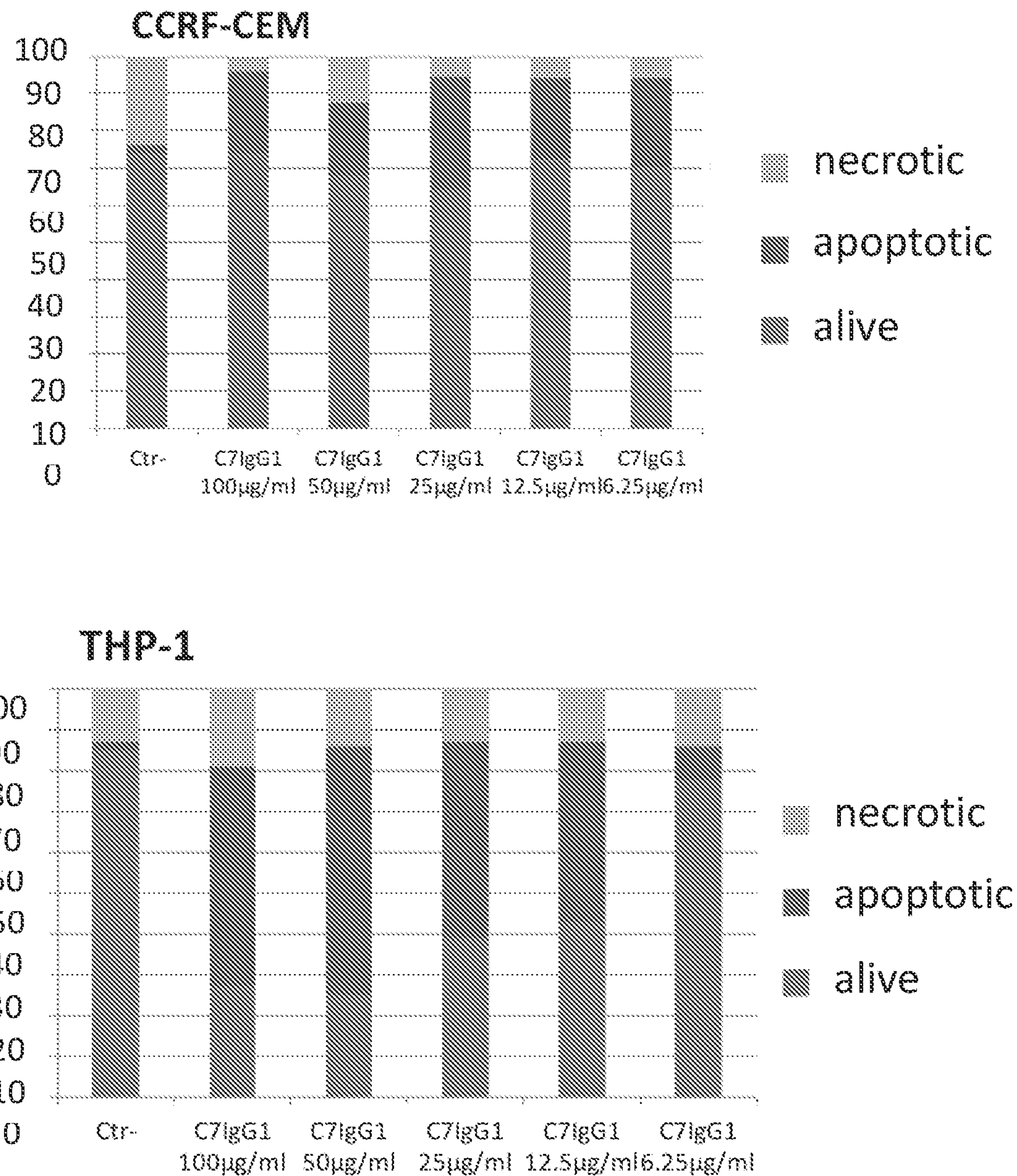

FIGS. 9 and 10 show the results of an analysis of leukaemia cell death induced by some example embodiments of the antibody complex of the invention (antibodies in the form of IgG1 and IgG4, i.e. C7IgG1 and C7IgG4) in leukaemia cells.

Figure 11:
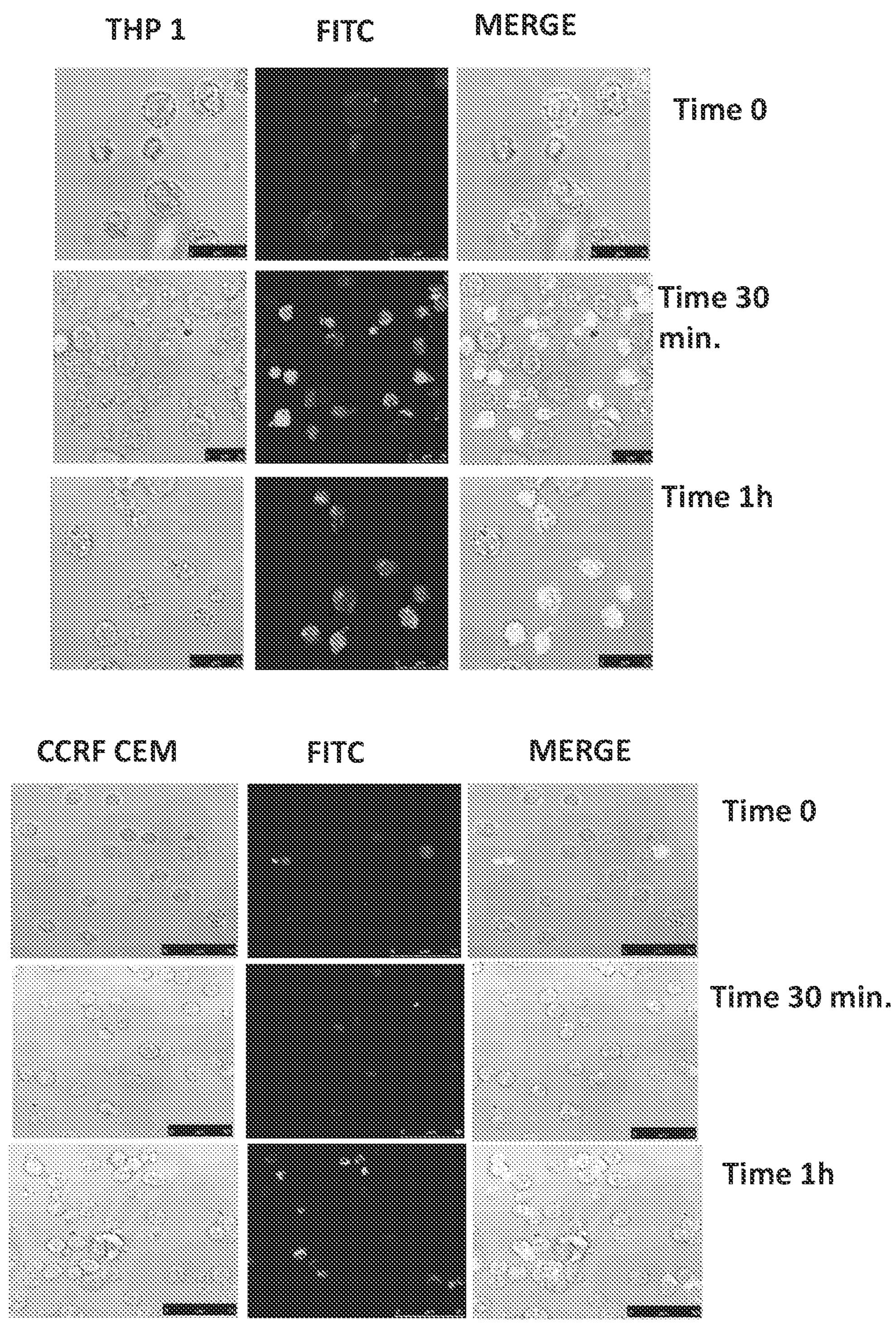

FIG. 11 shows the results of confocal microscopy regarding the capacity of leukaemia cells to internalize the antibody complex of the invention in diabody form following binding with CD99.

FIG. 12 shows (A) the alignment of the amino acid sequences of the extracellular domain of human, cynomolgus monkey, green monkey and mouse CD99 (the identical residues are marked with an asterisk (*), whereas two dots (:) indicate the conservative substitutions and one dot (.) the semi-conserved ones); (B) the alignment of the amino acid sequences of the epitope of scFvC7.

Figure 13:
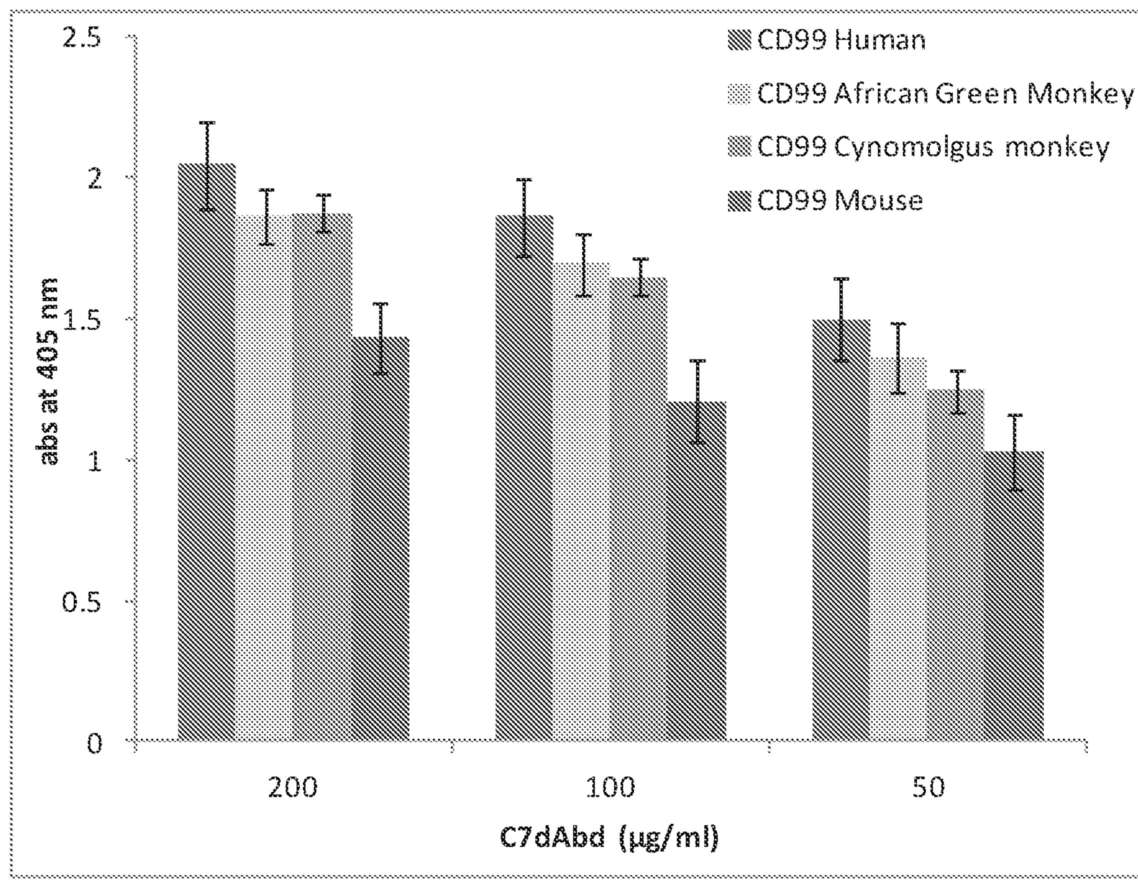

FIG. 13 shows the results regarding the reactivity of the antibody complex of the invention in diabody form for CD99 of different species, obtained by ELISA assays.

Figure 14:
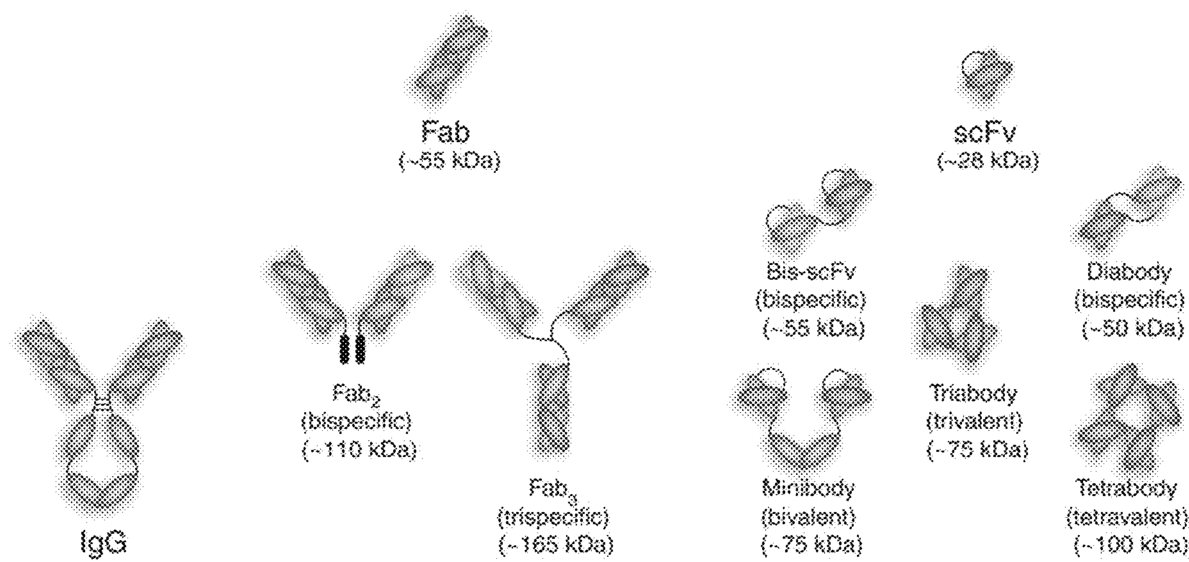

FIG. 14 shows a diagram of the various forms of the antibody complex of the present invention, in particular the IgG form and the diabody, triabody and tetrabody forms.

FIG. 15 shows a Western Blot analysis performed under nonreducing conditions on purified C7IgG4, C7IgG4S228P and C7 IgG1. The signal is given by an anti-C7Ab revealed by an anti-rabbit HRP. Panels A, B and C refer to 3 different productions of the antibody C7IgG4S228P.

Figure 16:
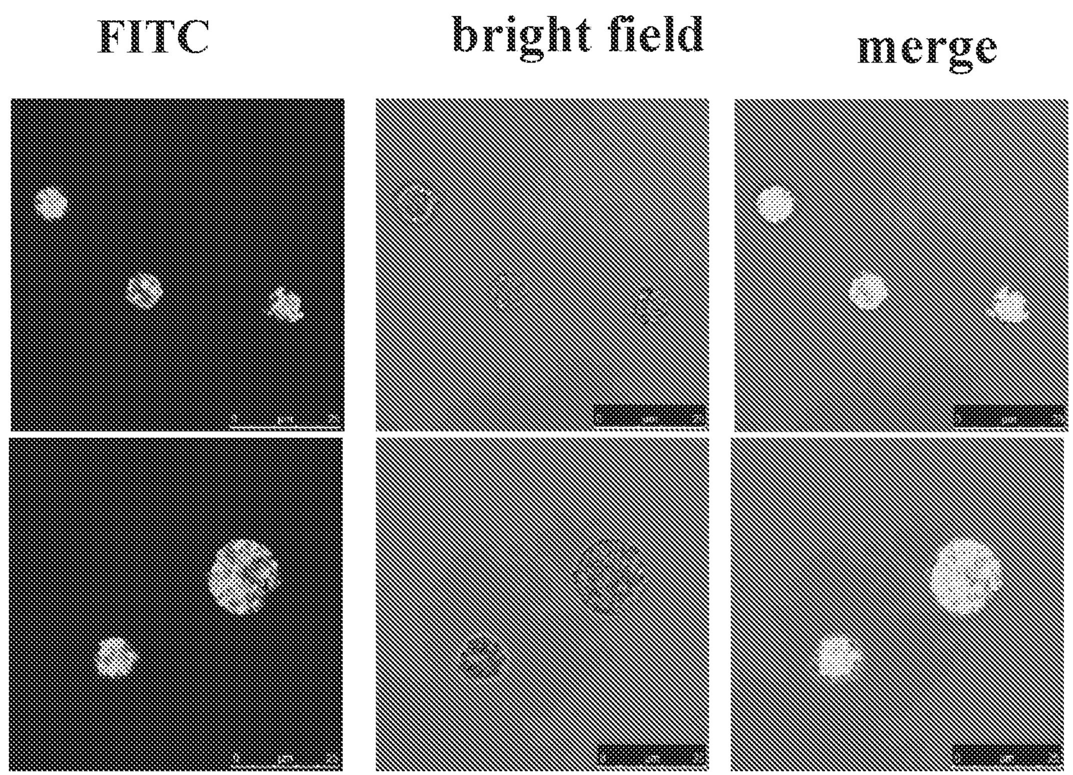

FIG. 16 shows the ability of a leukaemia cell line MOLM13 to internalize the diabody analysed by confocal microscopy.

Figure 17:
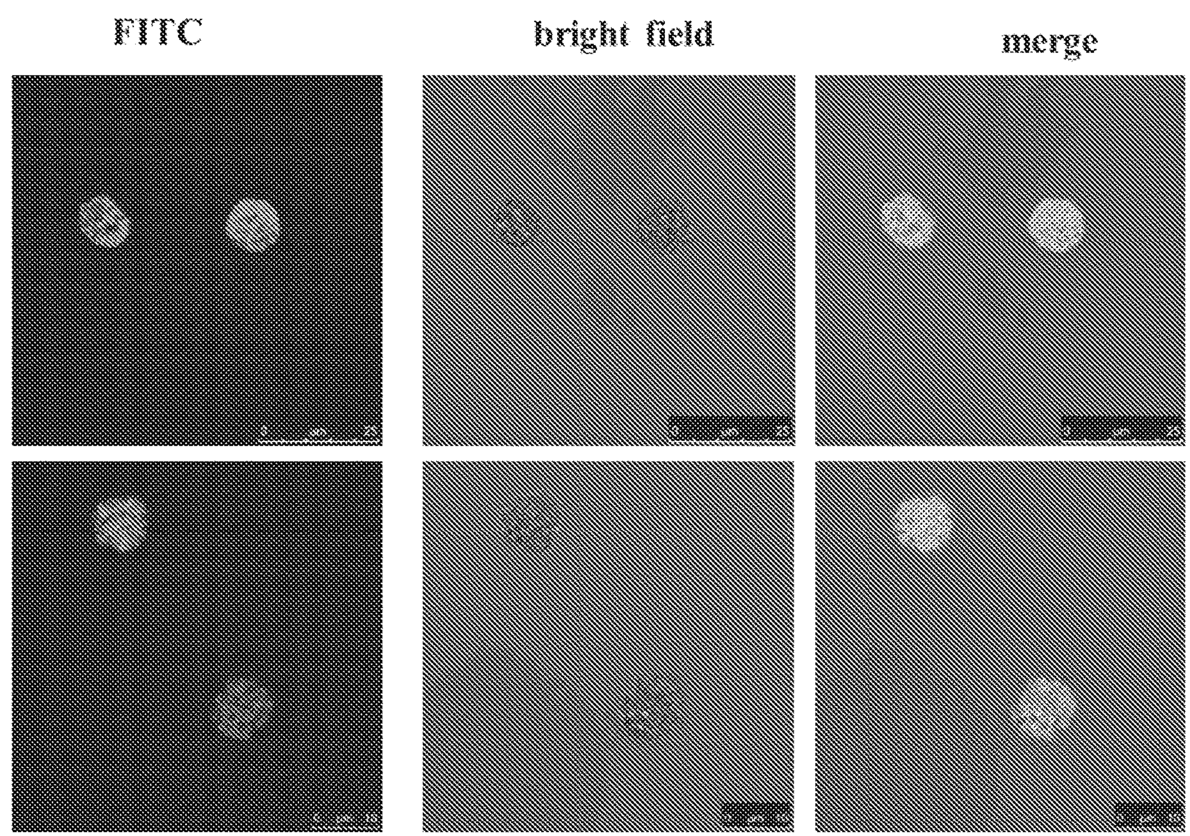

FIG. 17 shows the ability of a leukaemia cell line MOLM13 to internalize IgG4 analysed by confocal microscopy.

FIG. 18 shows the effectiveness of the diabody and of IgG4 according to the present invention in inducing apoptosis in spinal cord cells of an ALL leukaemia patient. (A) fluorescence intensity of the cells after binding with the antibody marked with FITC; (B) % of cells positive to binding of the antibody; (C) % live cells (in black), apoptotic cells (grey), necrotic cells (white).

Figure 19:
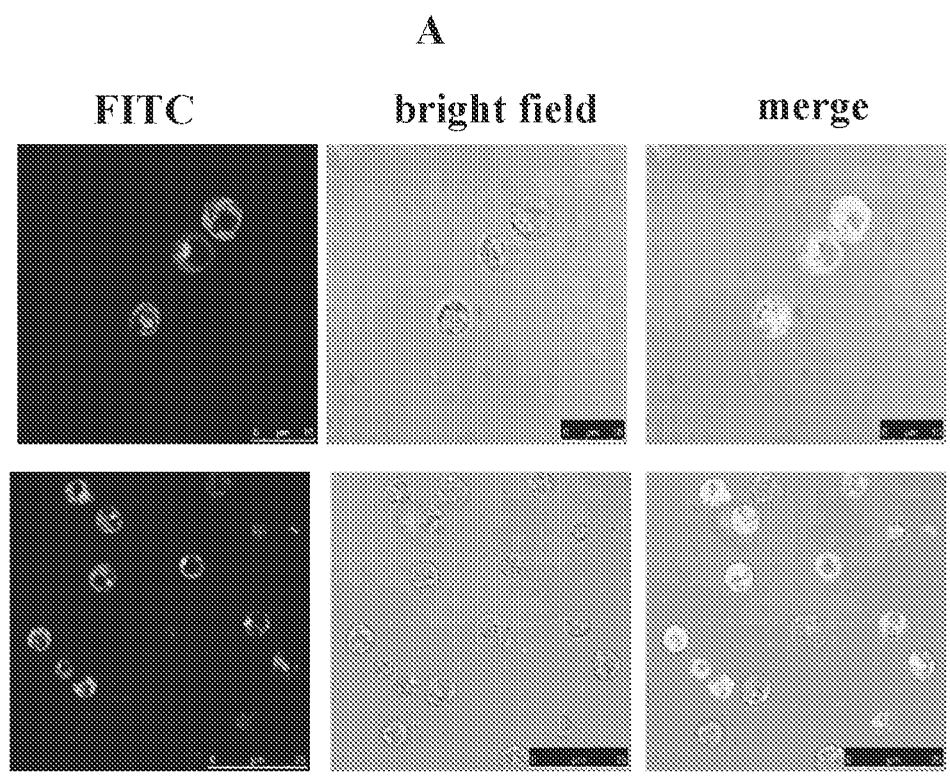
Figure 19:
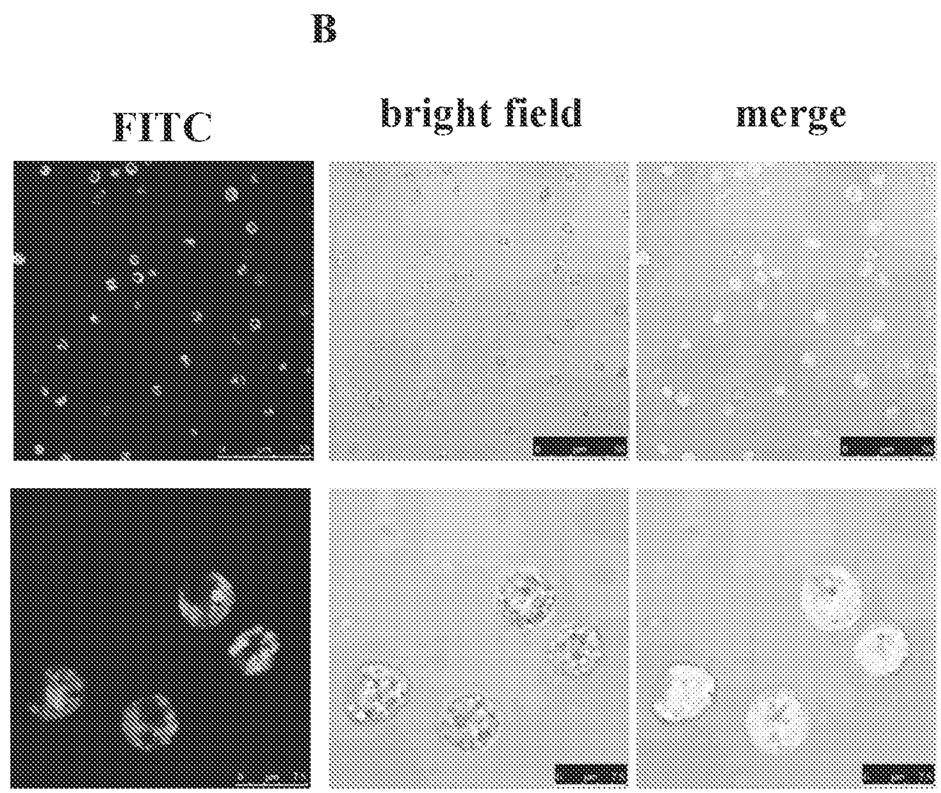
Figure 19:
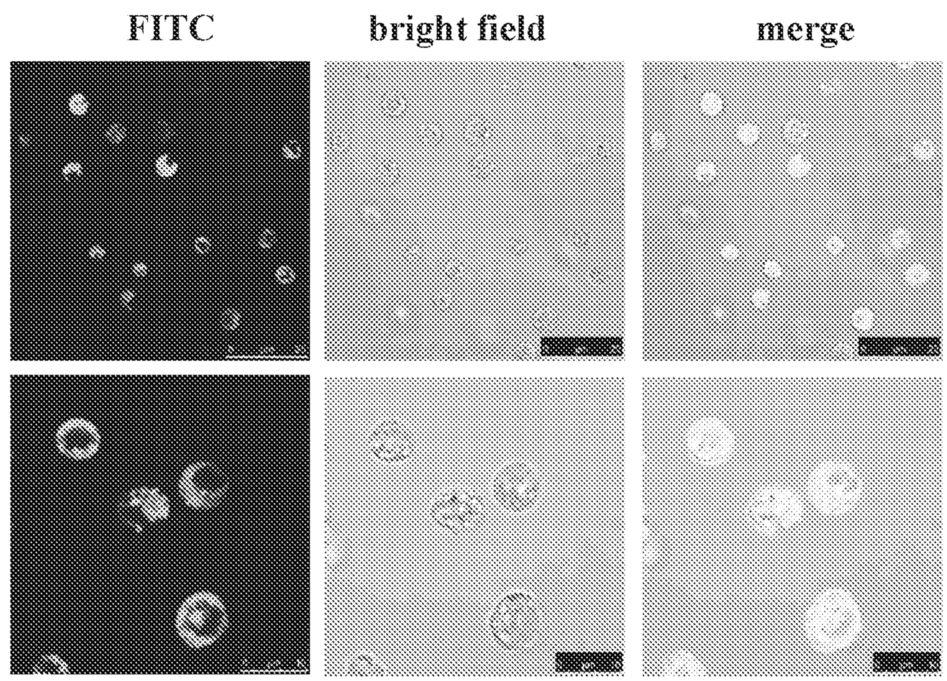
Figure 19:
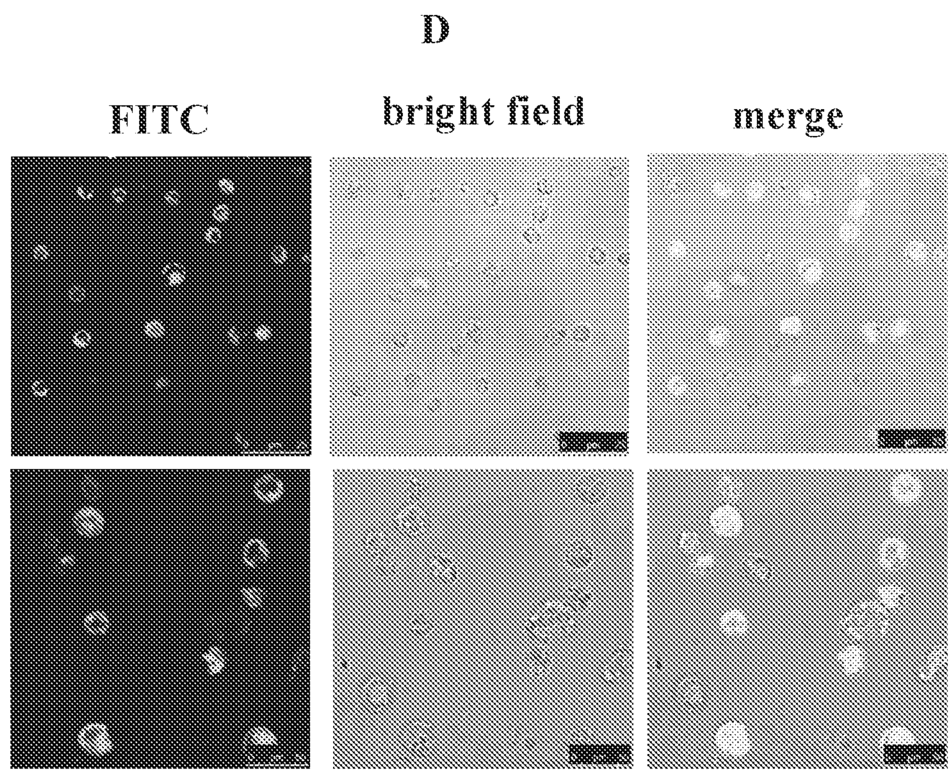

FIG. 19 shows the internalization of the diabody and of IgG4 in cells from an ALL patient analysed by confocal microscopy. (A) diabody after 1 h of incubation; (B) diabody after 2 h of incubation; (C) IgG4 after 1 h of incubation; (D) IgG4 after 2 h of incubation.

Figure 20:
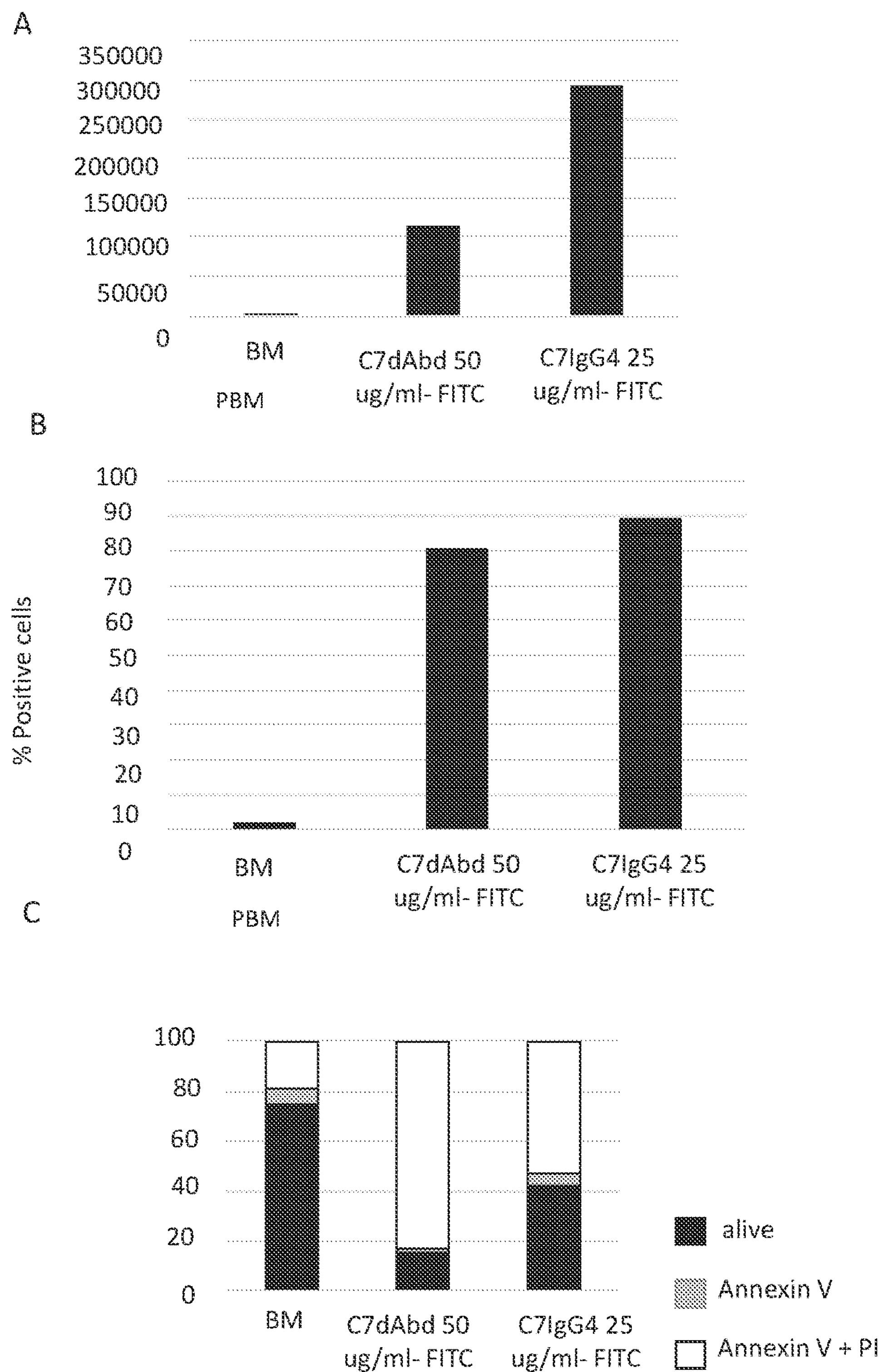

FIG. 20 shows the effectiveness of the diabody and of IgG4 according to the present invention in inducing apoptosis in peripheral blood cells of an AML leukaemia patient. (A) fluorescence intensity of the cells after binding with the antibody marked with FITC; (B) % of cells positive to binding of the antibody; (C) cytofluorometric assay of apoptosis by marking with Annexin V+propidium iodide (PI). % live cells (in black), apoptotic cells (grey), necrotic cells (white).

Figure 21:
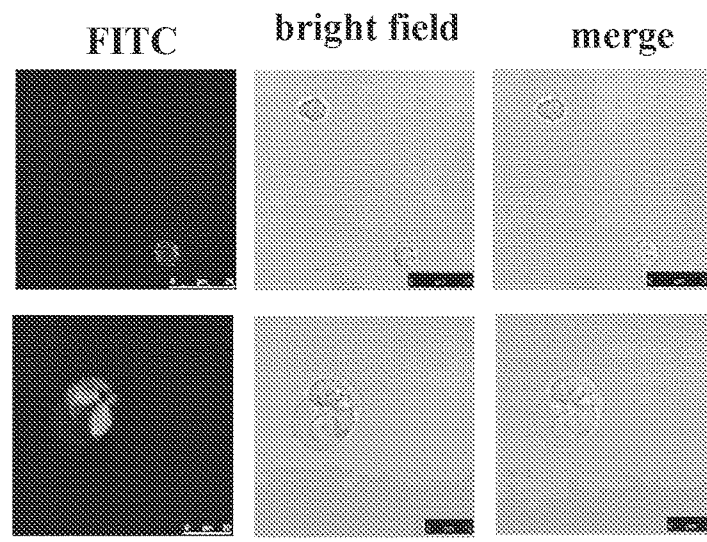

FIG. 21 shows the results obtained with the diabody in CD34+ cells from an AML patient. (A) confocal microscopy; (B) % of cells positive to binding of the antibody; (C) cytofluorometric quantization of apoptosis by marking with Annexin V+propidium iodide (PI).

Figure 22:
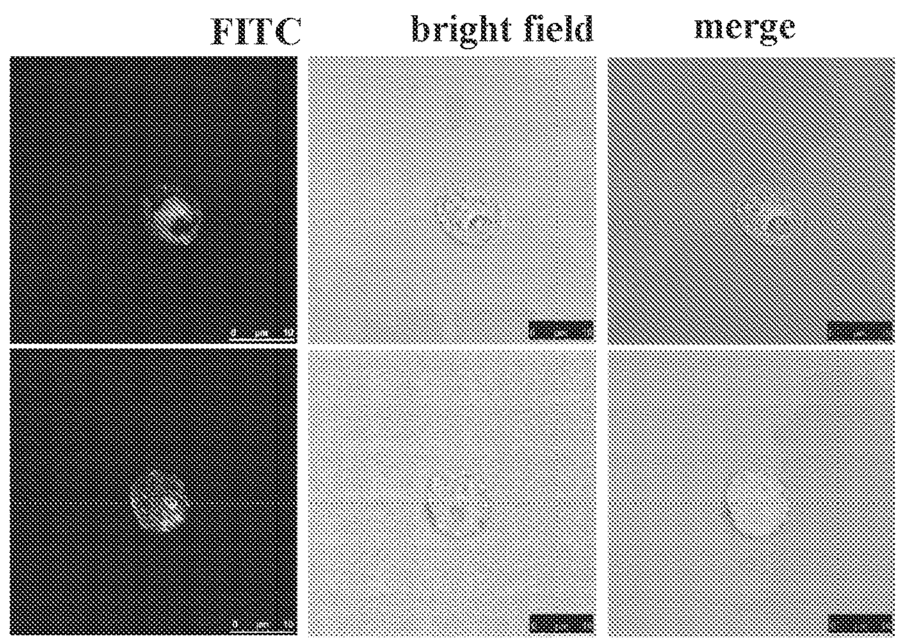
Figure 23A:
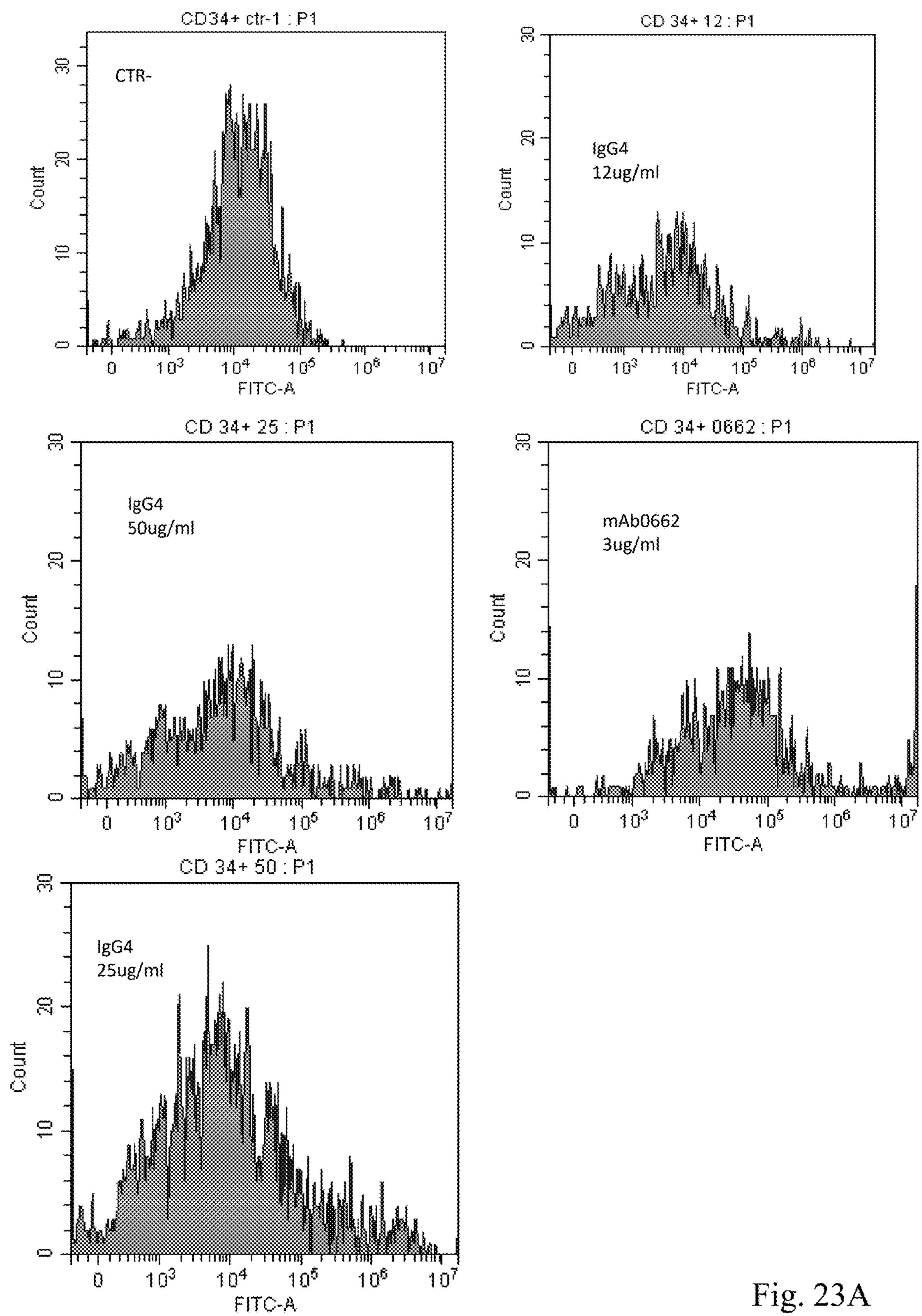
Figure 23B:
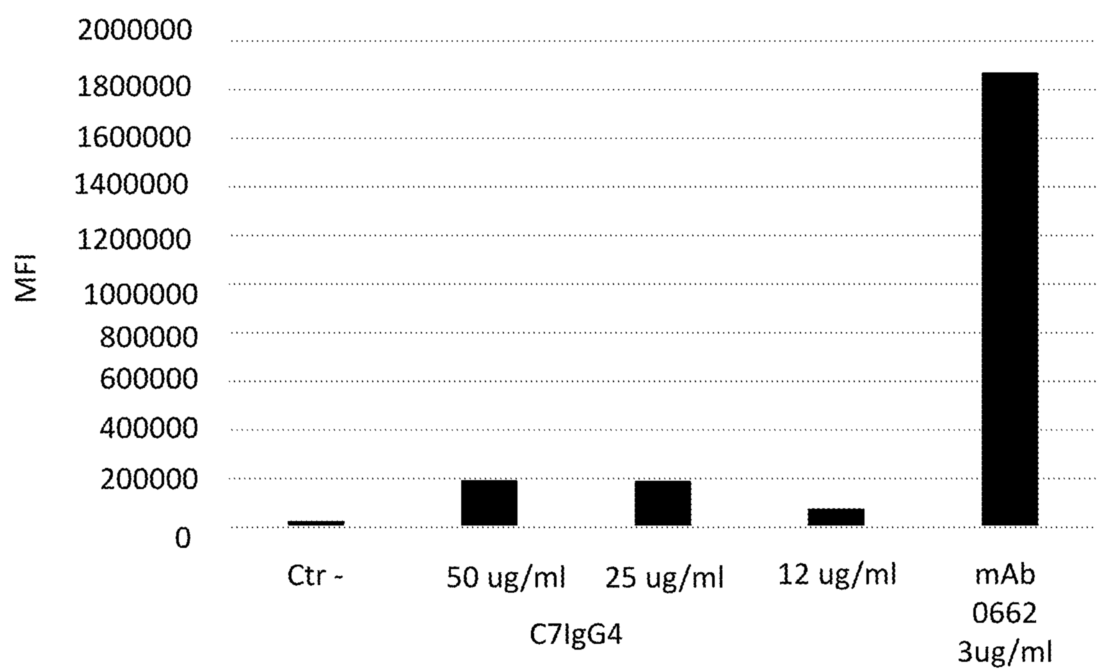
Figure 23C:
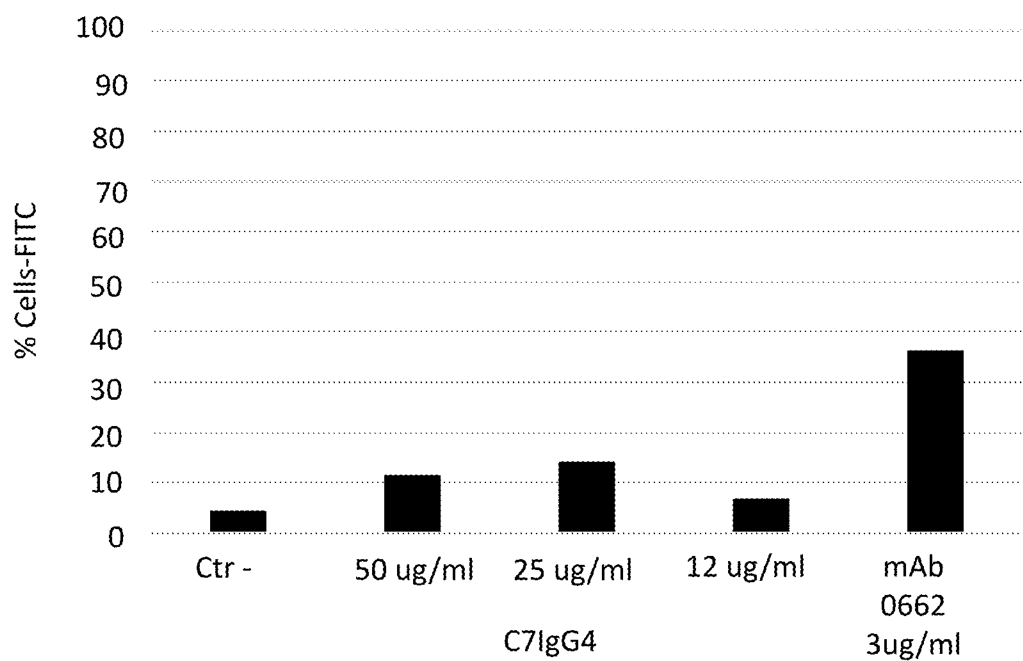
Figure 23D:
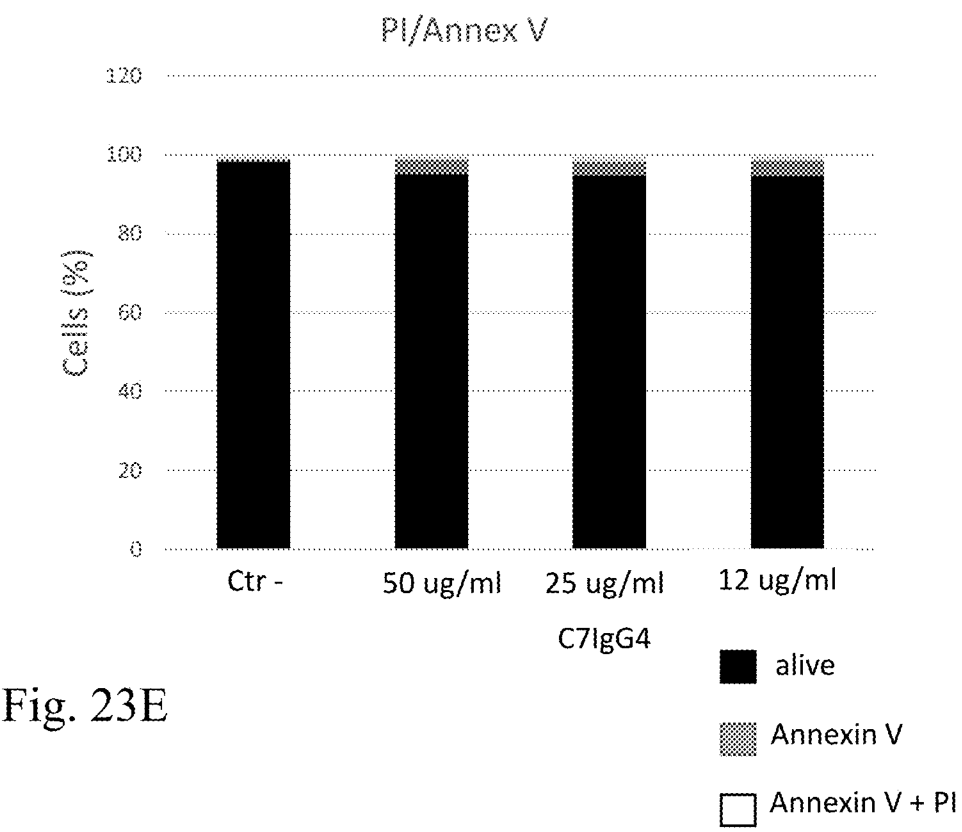
Figure 23E:
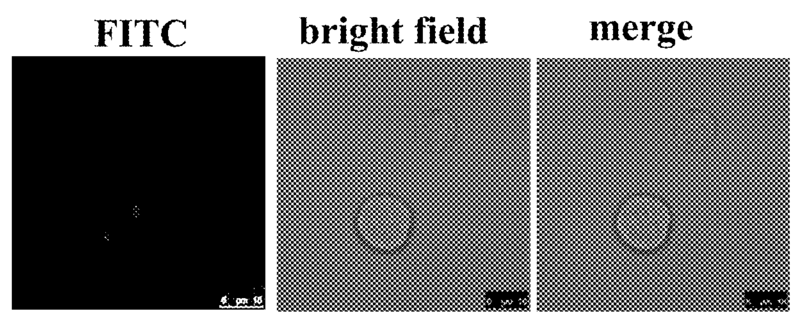
Figure 24A:
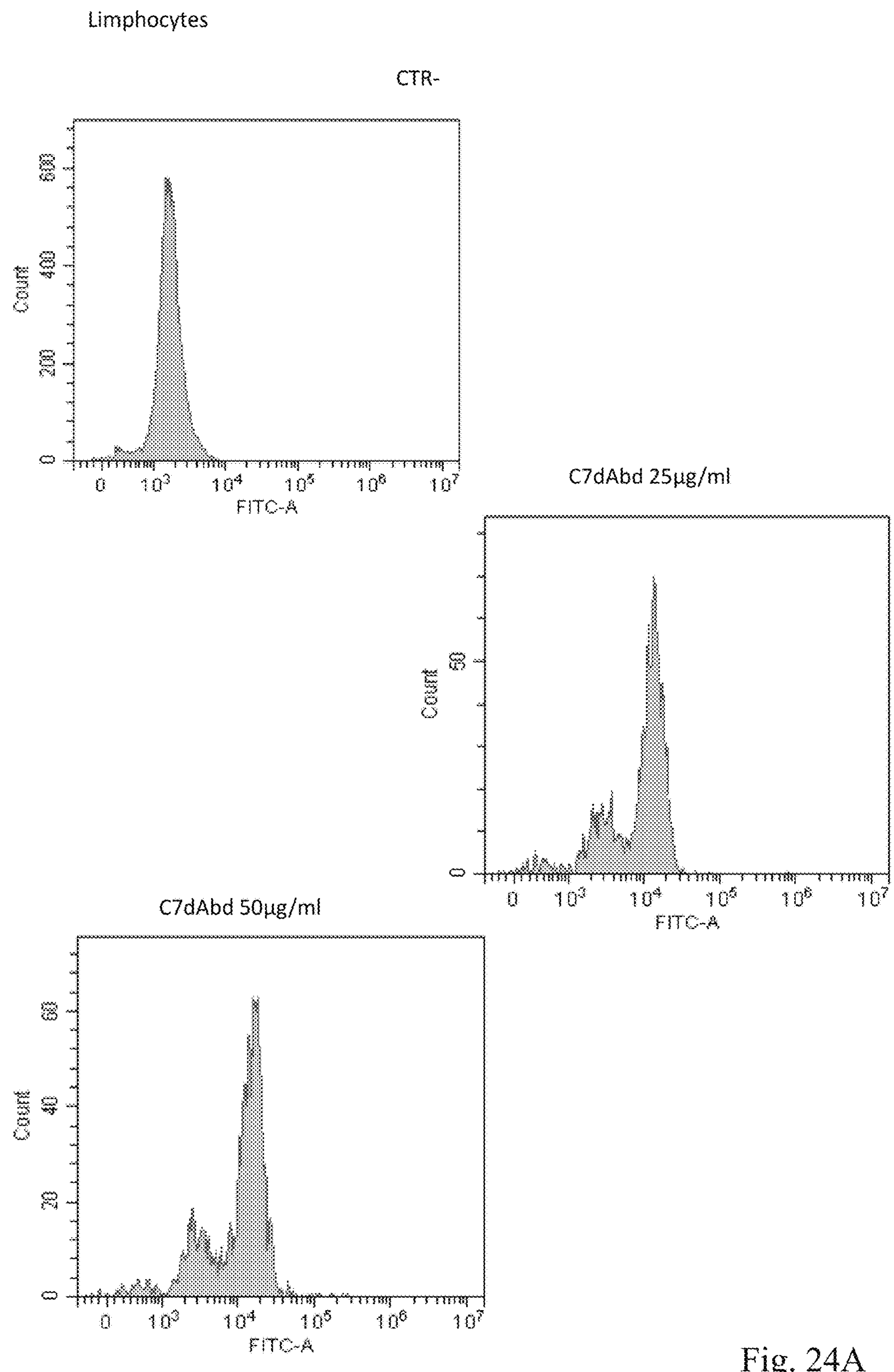
Figure 24B:
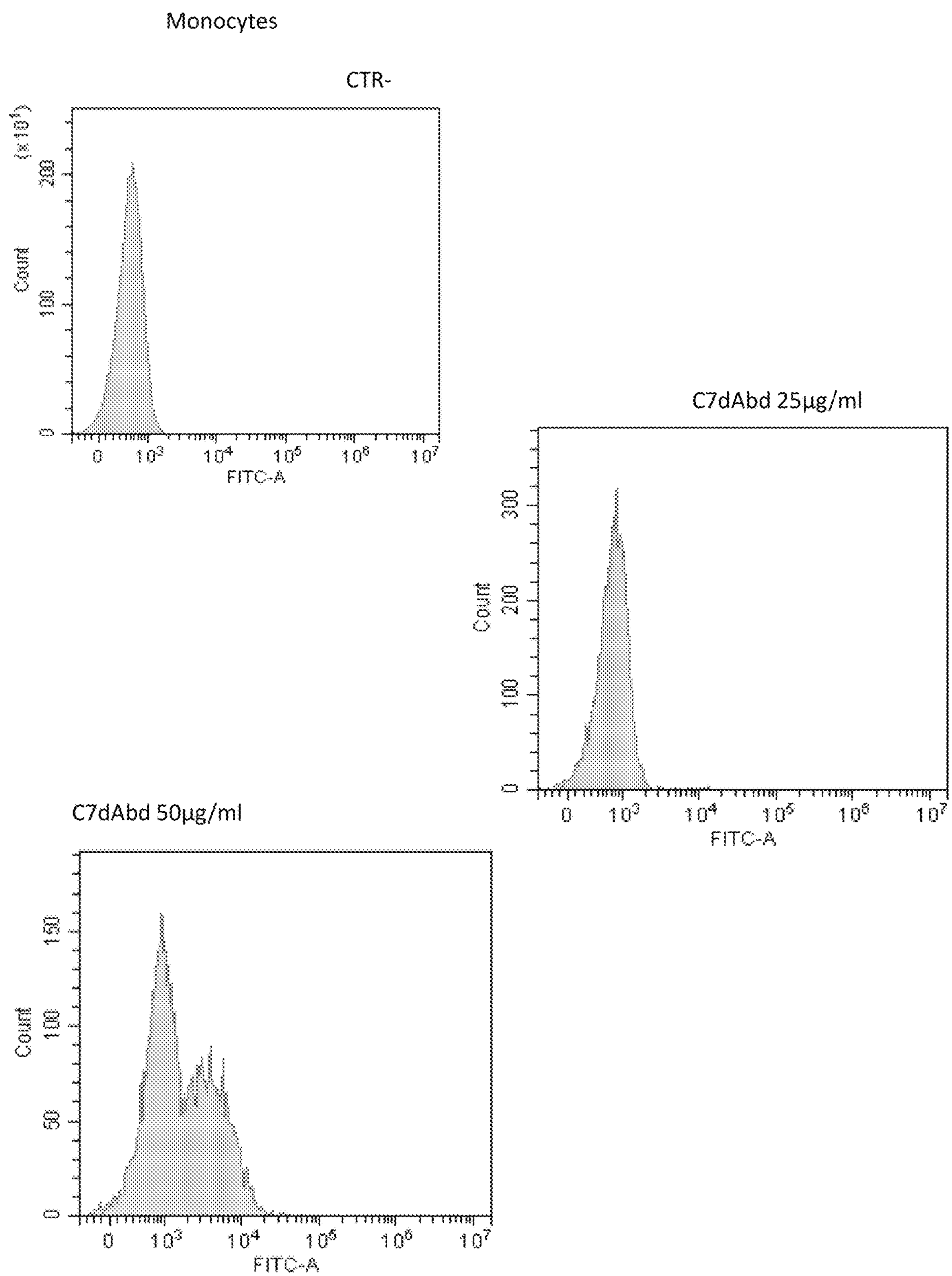
Figure 24C:
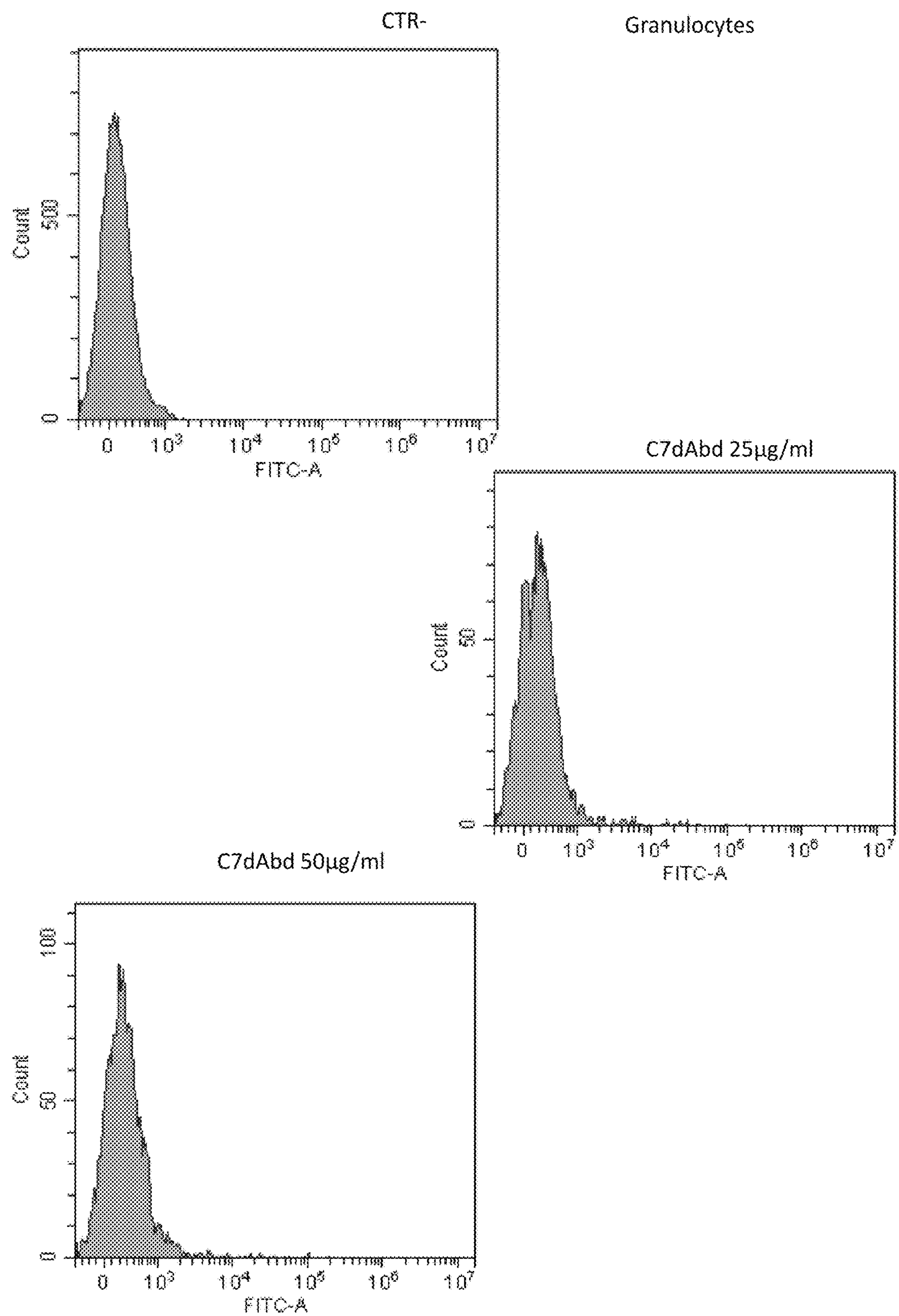
Figure 24D:
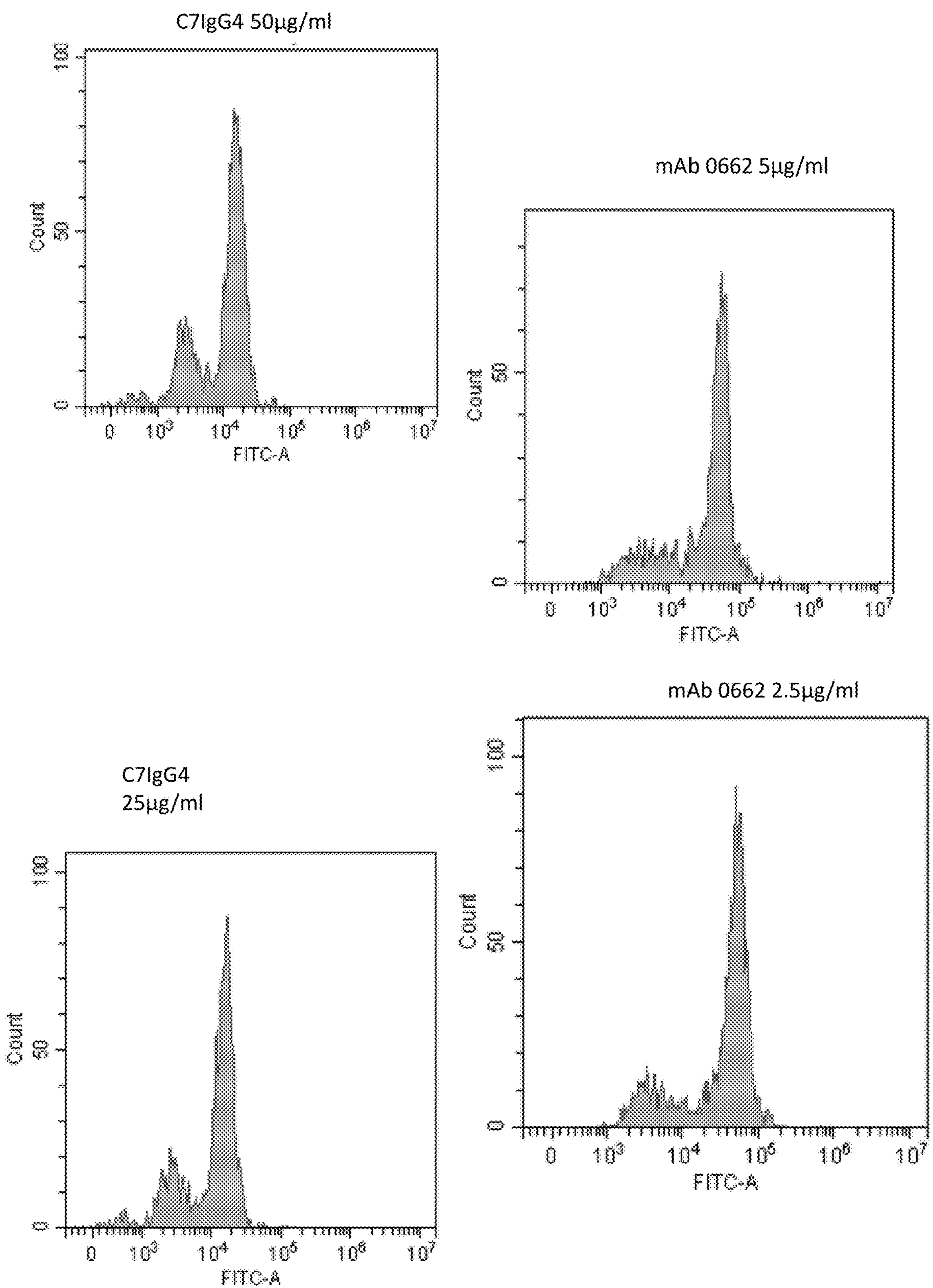
Figure 24F:
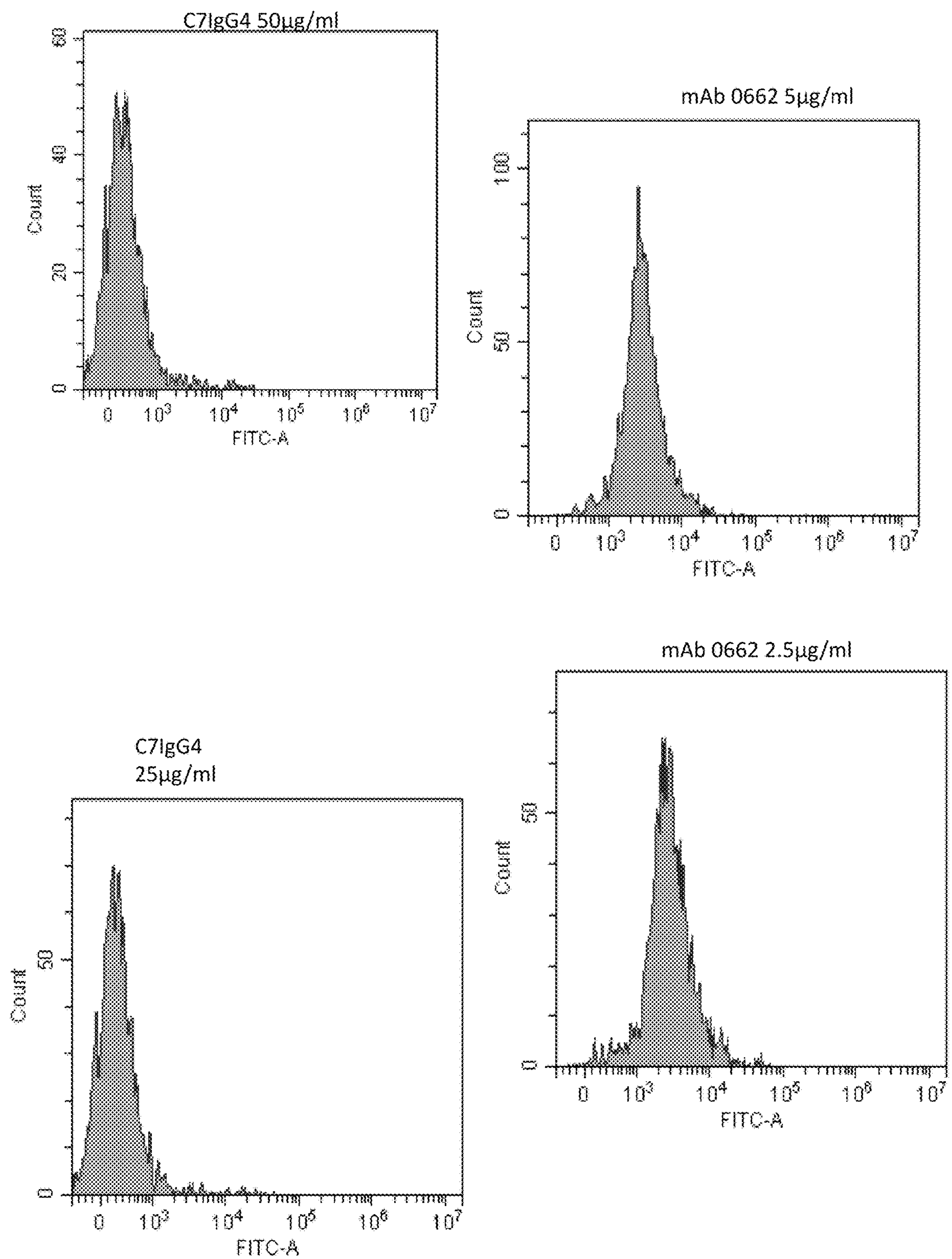
Figure 25A:
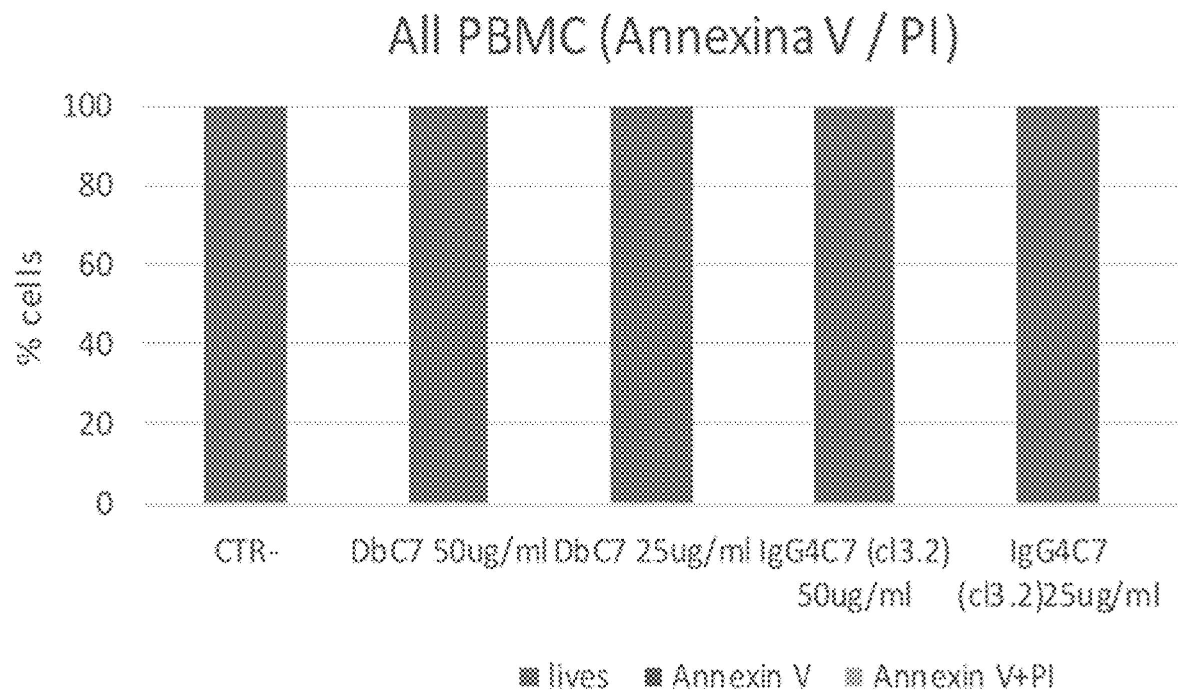
Figure 25B:
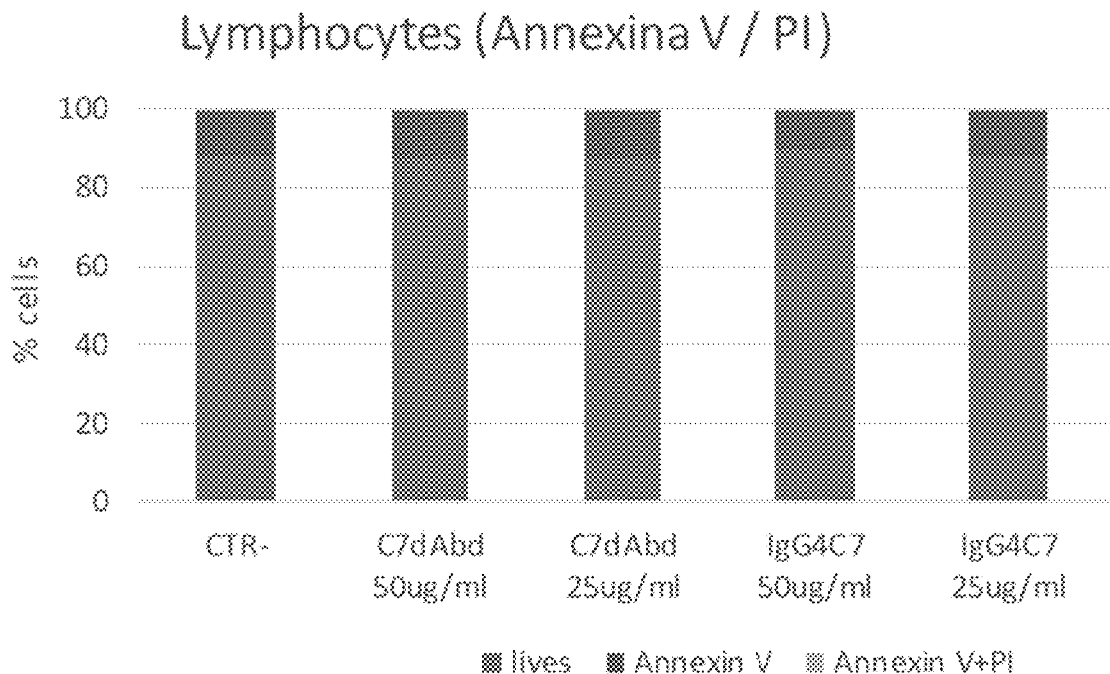
Figure 25C:
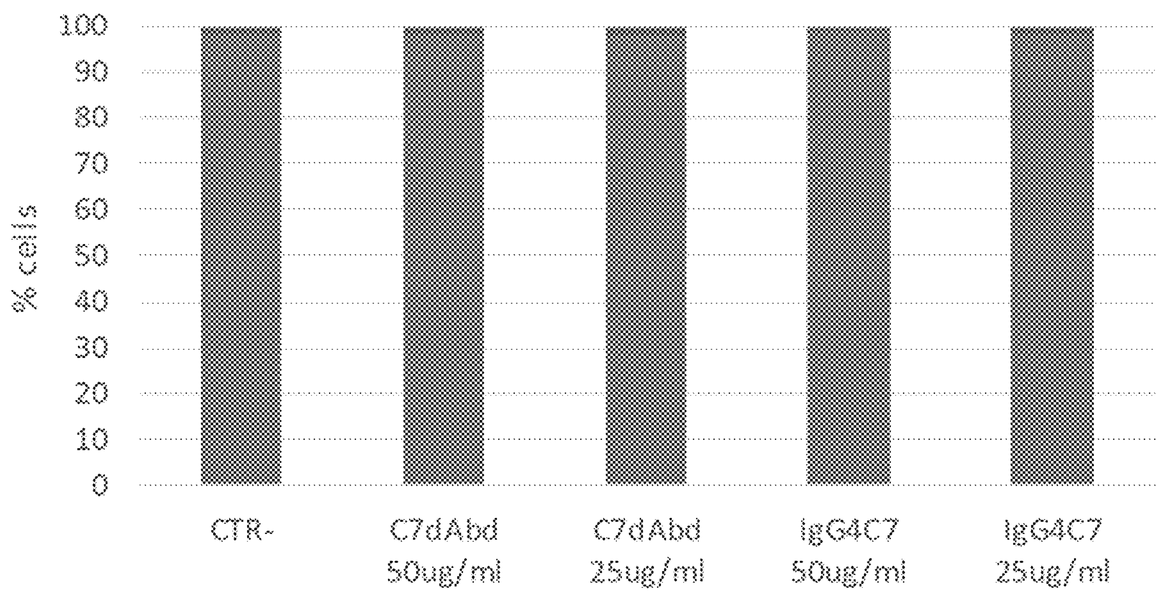
Figure 25D:
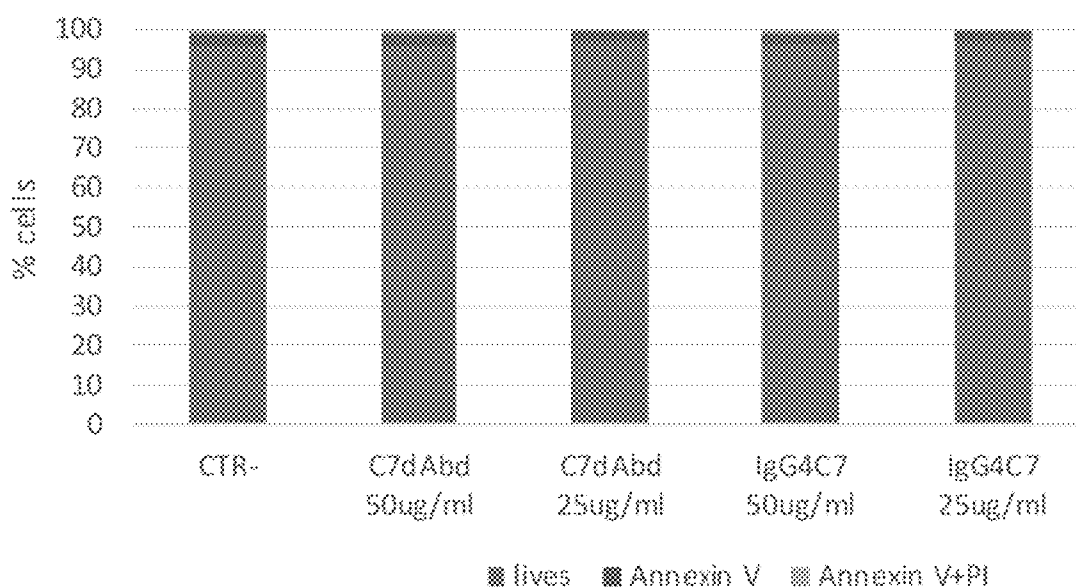

FIG. 22 shows the results obtained with IgG4 in CD34+ cells from an AML patient. (A) confocal microscopy; (B) % of cells positive to binding of the antibody; (C) cytofluorometric quantization of apoptosis by marking with Annexin V+propidium iodide (PI).

FIG. 23 shows the results obtained with IgG4 in CD34+ cells from a healthy donor. (A) fluorescence intensity and % of cells positive to binding of the antibody; the anti-CD99 monoclonal antibody clone 0662 was used as a positive control. (B) (C) and (D) quantization of apoptosis; (E) confocal microscopy.

FIG. 24 shows a cytofluorometric analysis on populations of peripheral blood cells incubated with the diabody (A) Lymphocytes, (B) monocytes, (C) Granulocytes or IgG4: (D) Lymphocytes, (E) monocytes and (F) Granulocytes. The anti-CD99 monoclonal antibody clone 0662 was used as a positive control.

FIG. 25 shows the % of apoptosis, measured with the Annexin V PI assay, in peripheral blood cells treated as per the experiment in FIG. 24: (A) All PBMC, (B) Lymphocytes, (C) monocytes and (D) Granulocytes.

Figure 26:
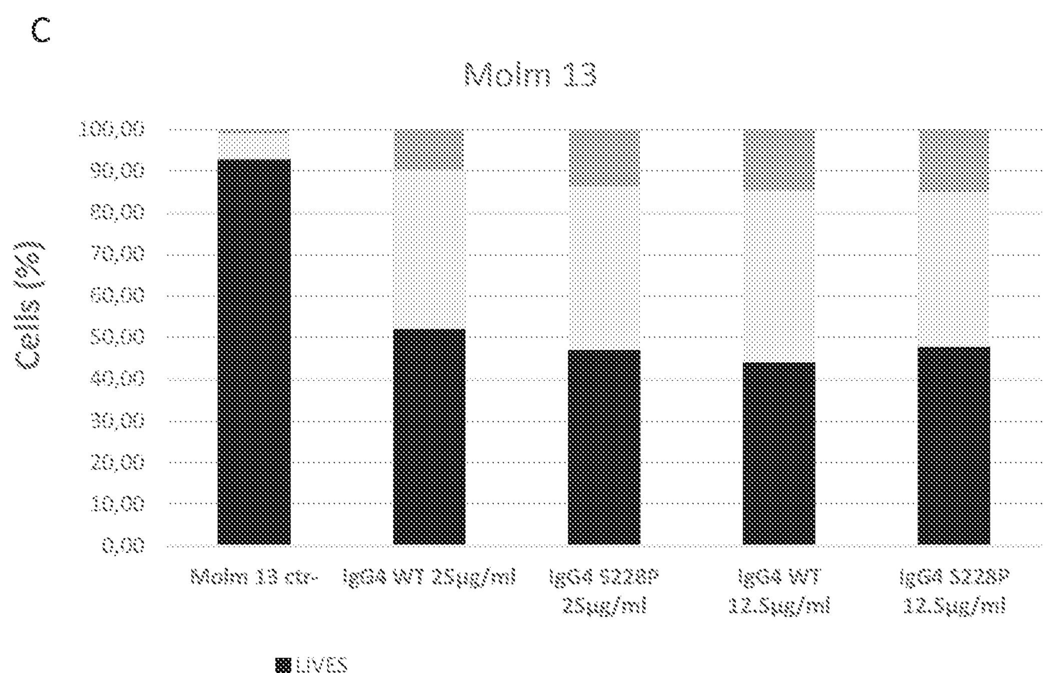

FIG. 26 shows a comparison between the results obtained with IgG4 wt and the mutated form IgG4S228P. (A) reactivity towards recombinant CD99, assessed by means of the ELISA assay. (B) confocal microscopy on the AML cell line MOLM13. (C) quantization of apoptosis.

DETAILED DESCRIPTION OF PREFERRED EMBODIMENTS OF THE INVENTION

In this context, "single-chain variable fragment" (scFv) means a particular type of antibody fragment obtained, for example, by means of the phage display technique.

This molecule is a fusion of the light chain (VL) and heavy chain (VH) variable regions of immunoglobulins, held together by a linker, i.e. the scFv is an antibody fragment of the Fv type consisting of a VH and a VL of an immunoglobulin joined by a linker, i.e. a flexible peptide of varying length which allows the VH-VL chains to take on the correct structure as a functional monomer unit.

The scFv can be engineered to form antibody complexes such as a diabody (dAbd) or bivalent scFv, or else a triabody or a tetrabody which bind together two, three or four scFvs, respectively, in other words the scFv can be engineered to form multivalent complexes, i.e. multivalent scFvs. Unlike monoclonal antibodies, which are often produced in cultured mammal cells, mono- and multivalent scFvs are often produced in cells of bacteria such as *Escherichia coli.*

In this context, an antibody, or, more precisely, an immunoglobulin, means a protein with a particular "Y"-shaped modular quaternary structure capable of binding in a highly specific manner to complementary structures called antigens.

Two fundamental components can be distinguished in an antibody

- a constant region (C), which mediates the interaction of the antibody with the complement or with innate immune cells ("Fc" portion).
- a variable region (V), which contains the site of combination with the antigen and thus varies according to the specificity of the antibody for a given antigen ("Fab" portion).

These components are structured so as to form a protein complex of the tetrameric type, which is composed of four glycoprotein chains, two heavy chains (H) identical to each other and two light chains (L) likewise identical to each other.

Moreover, each chain consists of a variable domain (VH in the case of the heavy chain, VL in the case of the light chain) located at the amino-terminal end and one or more constant domains at the carboxy-terminal end. Finally, in each variable domain, at the antigen-binding site, there are 3 hypervariable regions (CDR1, CDR2 and, finally, the most variable portion consisting of CDR3) interspersed with the so-called framework regions. On a structural level, the hypervariable regions are organized so as to form three closely spaced loops within a complex structure of beta sheets derived from the framework regions.

Human immunoglobulins are divided into 5 main classes: IgG, IgA, IgM, IgD and IgE.

The heavy chains are of the γ type, specific to each class of immunoglobulins, and each contain a variable Ig domain (VH or Vγ) and three constant domains (CH1/2/3 or Cγ1/2/3). In the case of IgGs, the γ chains can be produced in four different subtypes: γ1, γ2, γ3 and γ4. Therefore, immunoglobulins G are distinguished into a corresponding number of sub-families: IgG1, IgG2, IgG3 and IgG4, all with a similar structure and functions.

Monoclonal antibodies can be obtained by relying on different procedures, which include:

- the conventional system, which provides for the immunization of mice with a given antigen and the production of hybridomas that secrete the mouse antibody. The clinical use of mouse antibodies was conditioned right from the start by their intrinsic immunogenicity, but thanks to the availability of molecular techniques it was possible to reduce the immunogenicity by constructing chimeric or humanized antibodies which preserve the specificity of the variable regions or mouse CDRs, but use human sequences for the constant part and the framework regions.
- The use of transgenic mice capable of producing human antibodies.
- Phage-display technology, which is currently the most widely used method for selecting completely human recombinant antibody fragments and antibodies with a high affinity for the antigen.

In this context, CD99 is a transmembrane glycoprotein which, in humans, does not show any homology with other known proteins (except Xga). CD99 has a molecular mass of 32 kDa and is involved in important physiological functions which include cell adhesion, apoptosis, differentiation of T cells and thymocytes, migration of monocytes and the intracellular adhesion between lymphocytes and endothelial cells. In humans, the MIC2 gene encodes two distinct proteins following a process of alternative splicing: a full-length CD99 or type 1 (CD99 wt) and a truncated form called CD99 type II (CD99sh) with a shorter cytoplasmatic domain. The two CD99 isoforms are expressed in a cell-specific manner and have a different functional role. CD99 can be found on the cell surface both as a monomer and a homodimer, where two molecules of CD99 interact through the extracellular domain. These dimers can also be formed between the full-length and truncated isoforms. Furthermore, the interaction can also take place between two molecules of CD99 expressed on the surface of different cells.

Particularly relevant in this context is the extracellular domain of the CD99 protein recognized and bound by the molecules described here. The amino acid sequence and the encoding nucleotide sequence (CDS) of the extracellular domain of CD99 are respectively SEQ ID NO: 21 and 22. In particular, the sequence of the specific epitope of CD99 against which the molecules described here are directed comprises the amino acids 50-74 of the extracellular domain of CD99, i.e. SEQ ID NO: 23.

A first aspect of the present invention relates to an antibody complex comprising at least two variable regions capable of recognizing and binding the human protein CD99, for use in the diagnosis and/or the treatment and/or the follow-up of leukaemias and myelodysplastic syndromes, wherein each of said at least two variable regions comprises a variable domain/portion of the light chain (VL) and a variable domain/portion of the heavy chain (VH) of an immunoglobulin. In other words, the antibody complex to which the present invention makes reference comprises at least two variable regions of the light chain (VL) and at least two variable regions of the heavy chain (VH) of an immunoglobulin.

According to a preferred embodiment, said antibody complex is a diabody (dAbd) or bivalent scFv, or else a triabody or a tetrabody as defined earlier and characterized respectively by two, three and four variable regions, each having a variable domain/portion of the light chain (VL) and a variable domain/portion of the heavy chain (VH), as shown in FIG. 14.

According to a preferred embodiment, said antibody complex is an antibody in the IgG format, preferably a class 1 and/or 4 IgG. In this case as well, like for the diabody, the IgGs have at least two variable regions capable of recognizing and binding the human protein CD99, each of said at least two variable regions comprises a variable domain/portion of the light chain (VL) and a variable domain/portion of the heavy chain (VH).

In the case of the IgG forms there is obviously no linker, which exists, by contrast, in the multivalent scFvs and serves to hold together the individual monomeric units.

At the antigen-binding site, each VH and VL chain comprises 3 hypervariable regions which are defined, as is well known, CDR1, CDR2 and CDR3, which are interspersed with the so-called framework regions. CDR stands for Complementarity-Determining Region and CDR3 is the most variable region.

According to a preferred embodiment of the invention, at least one of the VH chains of the antibody complex comprises a CDR3 characterized by an amino acid sequence comprising SEQ ID NO: 1. Said at least two VH chains of the antibody complex preferably each comprise a CDR3 characterized by an amino acid sequence comprising SEQ ID NO: 1. That is, both of the VH chains comprise a CDR3 characterized by an amino acid sequence comprising SEQ ID NO: 1.

In the context of the present invention, "comprises, comprising" also means that the amino acid or nucleotide sequence in question is, or essentially corresponds to, the identified sequence.

Said multivalent, preferably bivalent (diabody), or trivalent (triabody) or quadrivalent (tetrabody) scFv, preferably has at least one VH chain comprising a CDR3 characterized by an amino acid sequence comprising SEQ ID NO: 1, preferably, the diabody has at least two VH chains, each comprising a CDR3 characterized by an amino acid sequence comprising SEQ ID NO: 1, the triabody has three VH chains, each comprising a CDR3 characterized by an amino acid sequence comprising SEQ ID NO: 1, the tetrabody has four VH chains, each comprising a CDR3 characterized by an amino acid sequence comprising SEQ ID NO: 1.

Said IgG, more preferably said IgG1 and/or said IgG4, preferably comprises at least one VH chain comprising a CDR3 characterized by an amino acid sequence comprising SEQ ID NO: 1; said IgG, more preferably said IgG1 and/or said IgG4, preferably comprises at least two VH chains, each comprising a CDR3 characterized by an amino acid sequence comprising SEQ ID NO: 1.

According to a preferred embodiment of the invention, at least one of the VL chains of the antibody complex comprises a CDR3 characterized by an amino acid sequence comprising SEQ ID NO: 2. Said at least two VL chains of the antibody complex preferably each comprise a CDR3 characterized by an amino acid sequence comprising SEQ ID NO: 2. That is, both of the VL chains comprise a CDR3 characterized by an amino acid sequence comprising SEQ ID NO: 2.

Said multivalent, preferably bivalent (diabody), or trivalent (triabody) or quadrivalent (tetrabody) scFv, preferably has at least one VL chain comprising a CDR3 characterized by an amino acid sequence comprising SEQ ID NO: 2, preferably, the diabody has at least two VL chains, each comprising a CDR3 characterized by an amino acid sequence comprising SEQ ID NO: 2, the triabody has three VL chains, each comprising a CDR3 characterized by an amino acid sequence comprising SEQ ID NO: 2, the tetrabody has four VL chains, each comprising a CDR3 characterized by an amino acid sequence comprising SEQ ID NO: 2.

Said IgG, more preferably said IgG1 and/or said IgG4, preferably comprises at least one VL chain comprising a CDR3 characterized by an amino acid sequence comprising SEQ ID NO: 2; said IgG, more preferably said IgG1 and/or said IgG4, preferably comprises at least two VL chains each comprising a CDR3 characterized by an amino acid sequence comprising SEQ ID NO: 2.

Said multivalent, preferably bivalent (diabody), or trivalent (triabody) or quadrivalent (tetrabody) scFv, preferably has at least one VH chain and one VL chain, each chain comprising a CDR3 characterized by an amino acid sequence comprising, respectively, SEQ ID NO: 1 and SEQ ID NO: 2. The diabody preferably has at least two VH chains and two VL chains, each VH and VL chain comprising a CDR3 characterized by an amino acid sequence comprising, respectively, SEQ ID NO: 1 and SEQ ID NO: 2. The triabody preferably has three VH chains and three VL chains, each VH and VL chain comprising a CDR3 characterized by an amino acid sequence comprising, respectively, SEQ ID NO: 1 and SEQ ID NO: 2. The tetrabody preferably has four VH chains and four VL chains, each VH and VL chain comprising a CDR3 characterized by an amino acid sequence comprising, respectively, SEQ ID NO: 1 and SEQ ID NO: 2.

Said IgG, more preferably said IgG1 and/or said IgG4, preferably comprises at least one VH chain and one VL chain, each VH chain and VL chain comprising a CDR3 characterized by an amino acid sequence comprising, respectively, SEQ ID NO: 1 and SEQ ID NO: 2; said IgG, more preferably IgG1 and/or IgG4, preferably comprises at least two VH chains and at least two VL chains, each VH and VL chain comprising a CDR3 characterized by an amino acid sequence comprising, respectively, SEQ ID NO: 1 and SEQ ID NO: 2.

In a preferred embodiment, the antibody variants as described above, preferably said multivalent scFv, more preferably said bivalent (diabody) and/or trivalent (triabody) and/or quadrivalent (tetrabody) scFv, or said IgG, preferably IgG1 and/or IgG4, comprise at least one CDR1 and/or CDR2 of the VH chain characterized by an amino acid sequence comprising SEQ ID NO: 3 (CDR1) and SEQ ID NO: 4 (CDR2). All of the CDR1s and/or the CDR2s of the VH chain of said variants are preferably characterized by an amino acid sequence comprising SEQ ID NO: 3 (CDR1) and SEQ ID NO: 4 (CDR2).

In a further preferred embodiment, the antibody variants as described above, preferably said multivalent scFv, more preferably said bivalent (diabody) and/or trivalent (triabody) and/or quadrivalent (tetrabody) scFv, or said IgG, preferably IgG1 and/or IgG4, comprise at least one CDR1 and/or CDR2 of the VL chain characterized by an amino acid sequence comprising SEQ ID NO: 5 (CDR1) and SEQ ID NO: 6 (CDR2). All of the CDR1s and/or the CDR2s of the VL chain of said variants are preferably characterized by an amino acid sequence comprising SEQ ID NO: 5 (CDR1) and SEQ ID NO: 6 (CDR2).

According to one embodiment of the invention, the VH chain and the VL chain of said antibody complex have an amino acid sequence comprising, respectively, SEQ ID NO: 7 and SEQ ID NO: 8. Said multivalent, preferably bivalent (diabody), or trivalent (triabody) or quadrivalent (tetrabody)

scFv, preferably has at least one VH chain and one VL chain characterized, respectively, by an amino acid sequence comprising SEQ ID NO: 7 and SEQ ID NO: 8. The diabody preferably has at least two VH chains and two VL chains, each chain being characterized by an amino acid sequence comprising, respectively, SEQ ID NO: 7 and SEQ ID NO: 8. The triabody preferably has three VH chains and three VL chains, each chain being characterized by an amino acid sequence comprising, respectively, SEQ ID NO: 7 and SEQ ID NO: 8. The tetrabody preferably has four VH chains and four VL chains, each chain being characterized by an amino acid sequence comprising, respectively, SEQ ID NO: 7 and SEQ ID NO: 8.

Said IgG, more preferably said IgG1 and/or said IgG4, preferably comprises at least one VH chain and one VL chain, each VH chain and VL chain being characterized by an amino acid sequence comprising, respectively, SEQ ID NO: 7 and SEQ ID NO: 8; said IgG, more preferably IgG1 and/or IgG4, preferably comprises at least two VH chains and at least two VL chains, each VH and VL chain being characterized by an amino acid sequence comprising, respectively, SEQ ID NO: 7 and SEQ ID NO: 8.

According to a preferred embodiment of the invention, the amino acid sequence of each heavy chain of said IgG4 comprises SEQ ID NO: 34 and/or the amino acid sequence of each light chain of said IgG4 comprises SEQ ID NO: 35. Said IgG4 preferably comprises two heavy chains characterized by an amino acid sequence comprising SEQ ID NO: 34 and/or two light chains characterized by an amino acid sequence comprising SEQ ID NO: 35.

SEQ ID NO: 34 comprises SEQ ID NO: 7—i.e. the variable portion of the heavy chain (VH)—and the constant portion of the heavy chain (CH1 hinge CH2CH3) of the IgG4s. SEQ ID NO: 35 comprises SEQ ID NO: 8—i.e. the variable portion of the light chain (VL)—and the constant portion of the light chain (CL).

According to a preferred embodiment of the invention, the amino acid sequence of each heavy chain of said IgG1 comprises SEQ ID NO: 38 and/or the amino acid sequence of each light chain of said IgG1 comprises SEQ ID NO: 39. Said IgG1 preferably comprises two heavy chains characterized by an amino acid sequence comprising SEQ ID NO: 38 and/or two light chains characterized by an amino acid sequence comprising SEQ ID NO: 39.

SEQ ID NO: 38 comprises SEQ ID NO: 7—i.e. the variable portion of the heavy chain (VH)—and the constant portion of the heavy chain of the IgG1s (CH1 hinge CH2CH3).

SEQ ID NO: 39 comprises SEQ ID NO: 8—i.e. the variable portion of the light chain (VL)—and the constant portion of the light chain (CL).

According to one embodiment of the invention:

- the nucleotide sequence of CDR3 of the VH chain comprises SEQ ID NO: 11;
- the nucleotide sequence of CDR3 of the VL chain comprises SEQ ID NO: 12.
- the nucleotide sequences of CDR1 and CDR2 of the VH chain respectively comprise SEQ ID NO: 13 and 14;
- the nucleotide sequences of CDR1 and CDR2 of the VL chain respectively comprise SEQ ID NO: 15 and 16.
- the nucleotide sequence of the VH chain comprises SEQ ID NO: 17;
- the nucleotide sequence of the VL chain comprises SEQ ID NO: 18;
- the nucleotide sequence of the heavy chain of said IgG4 comprises SEQ ID NO: 36;
- the nucleotide sequence of the light chain of said IgG4 comprises SEQ ID NO: 37;
- the nucleotide sequence of the heavy chain of said IgG1 comprises SEQ ID NO: 40;
- the nucleotide sequence of the light chain of said IgG1 comprises SEQ ID NO: 41.

According to a preferred embodiment of the invention, said complex comprises at least two variable regions directed against the extracellular domain of CD99, they are preferably directed against the amino acid sequence SEQ ID NO: 21. In this context, to be directed against means that the antibody complex being referred to, preferably as described above, is capable of recognizing and binding the extracellular domain of CD99, i.e. SEQ ID NO: 21. This is the so-called epitope, which preferably comprises the amino acid sequence 50-74 of the extracellular fraction of CD99, i.e. SEQ ID NO: 23.

According to a preferred embodiment, every scFv unit of the multivalent scFv molecule, more preferably a bivalent (diabody) and/or trivalent (triabody) and/or quadrivalent (tetrabody) scFv, has an amino acid sequence comprising SEQ ID NO: 10. The sequence marked grey is the linker and in some embodiments it can be repeated more than once. The nucleotide sequence of every scFv unit of the multivalent scFv molecule comprises SEQ ID NO: 20.

Each fragment scFv of the multivalent scFv molecule comprises a variable portion of the light chain (VL) and a variable portion of the heavy chain (VH) as described above. The VH and VL chains of each scFv are joined together by a linker whose amino acid sequence comprises at least one copy of SEQ ID NO: 9 (the portion in grey in SEQ ID NO: 10), preferably one copy.

The nucleotide sequence of said linker comprises at least one copy of SEQ ID NO: 19 or nucleotide sequences derived therefrom as a result of the degeneration of the genetic code, and preferably one, two or three units.

A second aspect of the invention relates to a composition comprising the antibody complex as described in detail above, preferably comprising said multivalent, more preferably bivalent (diabody), trivalent (triabody) or quadrivalent (tetrabody) scFvs, or the IgG antibody forms, preferably the classes IgG1 and/or IgG4.

Said composition can further comprise a pharmacologically acceptable carrier, preferably selected from among: an adjuvant, a delivery agent, a buffer, a salt, an antioxidant, a preservative, a surfactant, a polyol, a disaccharide, a polysaccharide, amino acids and combinations thereof.

The pharmacologically acceptable carriers are generally nontoxic for persons receiving them at the dosages and concentrations employed. The buffers are preferably selected from among: phosphate, citrate, acetate, other organic acids and combinations thereof. The antioxidants are preferably selected from among: ascorbic acid and methionine. The salts are preferably selected from among: sodium chloride. The preservatives are preferably selected from among: octadecyl dimethyl benzyl ammonium chloride; hexamethonium chloride; benzalkonium chloride; benzethonium chloride; phenol, butyl or benzyl alcohol. The surfactants are preferably selected from among: polysorbate 80 (Tween 80), polysorbate 20 (Tween 20), poloxamer 188 and combinations thereof. The polyols are preferably selected from among: mannitol and sorbitol, the disaccharides and polysaccharides are preferably selected from among: sucrose, trehalose, dextran, dextran 40 and combinations thereof. The amino acids are preferably selected from among: arginine, glycine, histidine, lysine, glutamine, asparagine and combinations thereof. The proteins are preferably selected from among: serum albumin, gelatine, immunoglobulins and combinations thereof. The hydrophilic polymers are preferably selected from among: polyvinylpyrrolidone and/or polyethylene glycol (PEG). The chelating agent is preferably EDTA. The metal complex is preferably a Zn-protein complex.

According to the present description, the antibody variants as described above, and the composition described above, can be effectively used for the purpose of diagnosis and/or in the treatment and/or the follow-up of leukaemias and myelodysplastic syndromes.

In fact, the antibody forms described above have shown this therapeutic capacity against leukaemias and myelodysplastic syndromes. This was surprising, as already partly discussed above, because the monovalent scFv molecule directed against the same epitope of CD99 as described above has not shown such capacities. Only when at least two sites of recognition for this epitope are present on an antibody complex may the therapeutic advantages described and claimed herein be observed. The multivalent, more preferably bivalent (diabody), trivalent (triabody) or quadrivalent (tetrabody) scFvs, or the IgG antibody forms, preferably the classes IgG1 and/or IgG4, are particularly effective. The molecules that perform best for the purposes described herein are the diabody and/or the IgG1s and/or the IgG4s, preferably the IgG4s, which show a greater ability to recognize and bind to the epitope, as well as an improved biological/therapeutic action, above all by virtue of their ability to specifically induce the death of leukaemia cells expressing CD99, i.e. CD99 positive (+) cells.

In fact, as shown in detail in the experimental part, IgG antibodies show considerable advantages for some therapeutic applications, namely: (i) they show a higher affinity for CD99 than the monomer and diabody scFv; (ii) in particular, the class IgG4 shows a dissociation constant ($K_d$) that is a good two orders of magnitude lower than that of scFv; (iii) they have better pharmacokinetics than scFv fragments; (iv) they have a longer half-life than scFv, ranging between 7 and 21 days; (v) they have effector functions such as antibody-dependent cellular cytotoxicity, antibody-dependent cellular phagocytosis and complement-dependent cytotoxicity, which are useful in certain therapeutic applications.

The leukaemias to which the present invention makes reference are preferably selected from among: acute lymphoblastic leukaemia (ALL), acute myeloid leukaemia (AML), chronic lymphatic leukaemia (CLL), chronic myeloid leukaemia (CML) and myelodysplastic syndrome (MDS). Acute leukaemia is particularly preferred, more preferably ALL, or AML.

Furthermore, the IgG antibody forms, preferably the classes IgG1 and IgG4, have shown therapeutic effectiveness against types of tumours other than leukaemias, i.e. also against solid tumours expressing CD99.

Therefore, a further aspect of the present invention relates to the IgG antibody forms and the derivatives thereof, preferably the classes IgG1 and IgG4, as described in detail above, for the therapeutic treatment and/or the follow-up of pathologies associated with CD99, preferably in pathologies caused by or associated with an altered expression, preferably overexpression, of CD99. Said pathologies are, preferably: solid tumours and blood cancers, sarcomas, including Ewing's sarcoma and soft tissue sarcomas (synovial sarcoma, mesenchymal chondrosarcoma and rhabdomyosarcoma), gastrointestinal cancer, liver cancer, lung cancer, breast cancer, prostate cancer, pancreatic cancer, head and neck cancer, kidney cancer, testicular cancer, ovarian cancer, neuroendocrine tumours, melanoma, malignant glioma and astrocytoma, lymphomas, leukaemias and myelodysplastic syndrome.

The derivatives of the IgG antibody form described herein are fragments derived therefrom; said fragments are preferably selected from among: F (ab') 2, fragment F (ab), VH, VHH, VL, VLL and combinations thereof.

According to a preferred embodiment of the invention, the amino acid sequence of each heavy chain of said IgG4 comprises SEQ ID NO: 34 and/or the amino acid sequence of each light chain of said IgG4 comprises SEQ ID NO: 35. Said IgG4 preferably comprises two heavy chains characterized by an amino acid sequence comprising SEQ ID NO: 34 and/or two light chains characterized by an amino acid sequence comprising SEQ ID NO: 35.

SEQ ID NO: 34 comprises SEQ ID NO: 7—i.e. the variable portion of the heavy chain (VH)—and the constant portion of the heavy chain (CH1 hinge CH3) of the IgG4s. SEQ ID NO: 35 comprises SEQ ID NO: 8—i.e. the variable portion of the light chain (VL)—and the constant portion of the light chain (CL).

According to a preferred embodiment of the invention, the amino acid sequence of each heavy chain of said IgG1 comprises SEQ ID NO: 38 and/or the amino acid sequence of each light chain of said IgG1 comprises SEQ ID NO: 39. Said IgG1 preferably comprises two heavy chains characterized by an amino acid sequence comprising SEQ ID NO: 38 and/or two light chains characterized by an amino acid sequence comprising SEQ ID NO: 39.

SEQ ID NO: 38 comprises SEQ ID NO: 7—i.e. the variable portion of the heavy chain (VH)—and the constant portion of the heavy chain of the IgG1s (CH1 hinge CH2CH3).

SEQ ID NO: 39 comprises SEQ ID NO: 8—i.e. the variable portion of the light chain (VL)—and the constant portion of the light chain (CL).

The subject matter of the invention also relates to all of the nucleotide sequences derived from the nucleotide sequences shown in Table I, for example, as a result of the degeneration of the genetic code.

The sequences of the invention are annotated according to the international standard WIPO ST.25 and the description thereof was developed with the program Patent-In 3.5.

The description of the sequences is appended hereto.

The sequences identified in Table I and in the description of the sequences appended to the present application are included in the present invention. All of the sequences having an identity with the sequences included in Table I ranging from 80 to 99.9% are to be considered included in the present description.

Table I below shows all the amino acid and nucleotide sequences and the corresponding "Sequence Identifier".

The underlined amino acids are the ones subject to the highest variability.

TABLE I

| | | |
|---|---|---|
| SEQ ID NO: 1 | 97-A K S H K R F D Y-105 | Amino acid sequence of CDR3 of the VH chain |

TABLE I-continued

| | | |
|---|---|---|
| SEQ ID NO: 2 | 88-N S S F P R T S S V V-98 | Amino acid sequence of CDR3 of the VL chain |
| SEQ ID NO: 3 | 26-G F T F S S Y A M S-35 | Amino acid sequence of CDR1 of the VH chain |
| SEQ ID NO: 4 | 50-A I S G S G G S T-58 | Amino acid sequence of CDR2 of the VH chain |
| SEQ ID NO: 5 | 23-Q G D S L R S Y Y A S-33 | Amino acid sequence of CDR1 of the VL chain |
| SEQ ID NO: 6 | 49-G K N N R P S-55 | Amino acid sequence of CDR2 of the VL chain |
| SEQ ID NO: 7 | 1 - E V Q L V E S G G G L V R P G G S L R L S C A A S G F T F S S Y A M S W V R Q A P G K G L and W V S A I S G S G G S T Y Y A D S V K G R F T I S R D N S K N T L Y L Q M N S L R A E D T A V Y Y C A K S H K R F D Y W G Q G T L V T V S R-118 | Amino acid sequence of the VH chain |
| SEQ ID NO: 8 | 1- S S E L T Q D P A V S V A L G Q T V R I T C Q G D S L R S Y Y A S W Y Q Q K P G Q A P V L V I Y G K N N R P S G I P D R F S G S S S G N T A S L T I T G A Q A E D E A D Y Y C N S S F P R T S S V V F G G G T K L T V L G-109 | Amino acid sequence of the VL chain |
| SEQ ID NO: 9 | 1-G G G G S -5 | Amino acid sequence of the unit composing the linker |
| SEQ ID NO: 10 | 1- E V Q L V E S G G G L V R P G G S L R L S C A A S G F T F S S Y A M S W V R Q A P G K G L E W V S A I S G S G G S T Y Y A D S V K G R F T I S R D N S K N T L Y L Q M N S L R A E D T A V Y Y C A K S H K R F D Y W G Q G T L V T V S R G G G G S S E L T Q D P A V S V A L G Q T V R the T C Q G D S L R S Y Y A S W Y Q Q K P G Q A P V L V I Y G K N N R P S G I P D R F S G S S S G N T A S L T I T G A Q A E D E A D Y Y C N S S F P R T S S V V F G G G T K L T V L G-229 | Amino acid sequence of the scFv unit of the multivalent scFv molecule |
| SEQ ID NO: 11 | 289-GCG AAA TCG CAT AAG CGT TTT GAC TAC-315 | Nucleotide sequence of CDR3 of the VH chain |
| SEQ ID NO: 12 | 262-AAC TCC TCT TTT CCC CGG ACT TCT TCT GTG GTA-295 | Nucleotide sequence of CDR3 of the VL chain |
| SEQ ID NO: 13 | 76-GGA TTC ACC TTT AGC AGC TAT GCC ATG AGC-105 | Nucleotide sequence of CDR1 of the VH chain |
| SEQ ID NO: 14 | 148-GCT ATT AGT GGT AGT GGT GGT AGC ACA-174 | Nucleotide sequence of CDR2 of the VH chain |
| SEQ ID NO: 15 | 67- CAA GGA GAC AGC CTC AGA AGC TAT TAT GCA AGC-100 | Nucleotide sequence of CDR1 of the VL chain |

TABLE I-continued

| | | |
|---|---|---|
| SEQ ID NO: 16 | 145-GGT AAA AAC AAC CGG CCC TCA-166 | Nucleotide sequences of CDR2 of the VL chain |
| SEQ ID NO: 17 | 1- GAG gTG CAG CTG GTG GAG TCT GGG GGA GGC TTG GTA CGG CCT GGG GGG TCC CTG AGA CTC TCC TGT GCA GCC TCT GGA TTC ACC TTT AGC AGC TAT GCC ATG AGC TGG GTC CGC CAG GCT CCA GGG AAG GGG CTG GAG TGG GTC TCA GCT ATT AGT GGT AGT GGT GGT AGC ACA TAC TAC GCA GAC TCC GTG AAG GGC CGG TTC ACC ATC TCC AGA GAC AAT TCC AAG AAC ACG CTG TAT CTG CAA ATG AAC AGC CTG AGA GCC GAG GAC ACG GCC GTA TAT TAC TGT GCG AAA TCG CAT AAG CGT TTT GAC TAC TGG GGC CAG GGA ACC CTG GTC ACC GTG TCG AGA-354 | Nucleotide sequence of the VH chain |
| SEQ ID NO: 18 | 1- TGC TCT GAG CTG ACT CAG GAC CCT GCT GTG TCT GTG GCC TTG GGA CAG ACA GTC AGG ATC ACA TGC CAA GGA GAC AGC CTC AGA AGC TAT TAT GCA AGC TGG TAC CAG CAG AAG CCA GGA CAG GCC CCT GTA CTT GTC ATC TAT GGT AAA AAC AAC CGG CCC TCA GGG ATC CCA GAC CGA TTC TCT GGC TCC AGC TCA GGA AAC ACA GCT TCC TTG ACC ATC ACT GGG GCT CAG GCG GAA GAT GAG GCT GAC TAT TAC TGT AAC TCC TCT TTT CCC CGG ACT TCT TCT GTG GTA TTC GGC GGA GGG ACC AAG CTG ACC GTC CTA GGC 327 | Nucleotide sequence of the VL chain |
| SEQ ID NO: 19 | 1- GGC GGT GGC GGA TCG -15 | Nucleotide sequence of the unit composing the linker |
| SEQ ID NO: 20 | 1- GAG GTG CAG CTG GTG GAG TCT GGG GGA GGC TTG GTA CGG CCT GGG GGG TCC CTG AGA CTC TCC TGT GCA GCC TCT GGA TTC ACC TTT AGC AGC TAT GCC ATG AGC TGG GTC CGC CAG GCT CCA GGG AAG GGG CTG GAG TGG GTC TCA GCT ATT AGT GGT AGT GGT GGT AGC ACA TAC TAC GCA GAC TCC GTG AAG GGC CGG TTC ACC ATC TCC AGA GAC AAT TCC AAG AAC ACG CTG TAT CTG CAA ATG AAC AGC CTG AGA GCC GAG GAC ACG GCC GTA TAT TAC TGT GCG AAA TCG CAT AAG CGT TTT GAC TAC TGG GGC CAG GGA ACC CTG GTC ACC GTT TCG AGA GGC GGT GGO GGA TCG TCT GAG CTG ACT CAG GAC CCT GCT GTG TCT GTG GCC TTG GGA CAG ACA GTC AGG ATC ACA TGC CAA GGA GAC AGC CTC AGA AGC TAT TAT GCA AGC TGG TAC CAG CAG AAG CCA GGA CAG GCC CCT GTA CTT GTC ATC TAT GGT AAA AAC AAC CGG CCC TCA GGG ATC CCA GAC CGA TTC TCT GGC TCC AGC TCA GGA AAC ACA GCT TCC TTG ACC ATC ACT GGG GCT CAG GCG GAA GAT GAG GCT GAC TAT TAC TGT AAC TCC TCT TTT CCC CGG ACT TCT TCT GTG GTA TTC GGC GGA GGG ACC AAG CTG ACC GTC CTA GGC-687 | Nucleotide sequence of the scFv unit of the multivalent scFv molecule |
| SEQ ID NO: 21 | 23-D G G F D L S D A L P D N E N K K P T A I P K K P S A G D D F D L G D A V V D G E N D D P R P P N P P K P M P N P N P N H P S S S G S F S D A D L A D G V S G G E G K G G S D G G G S H R K E G E E A D-122 | Amino acid sequence of the extracellular domain of CD99 |
| SEQ ID NO: 22 | 67- GAT GGT GGT TTC GAT TTA TCC GAT GCC CTT CCT GAC AAT GAG AAC AAG AAA CCC ACT GCA ATC CCC AAG AAA CCC AGT GCT GGG GAT GAC TTT GAC TTA GGA GAT GCT GTT GTT GAT GGA GAA AAT GAC GAC CCA CGA CCA CCG AAC CCA CCC AAA CCG ATG CCA AAT CCA AAC CCC AAC CAC CCT AGT TCC TCC GGT AGC TTT TCA GAT GCT GAC CTT GOG GAT GGC GTT TCA GGT GGA GAA GGA AAA GGA GGC AGT GAT GGT GGA GGC AGC CAC AGG AAA GAA GGG GAA GAG GCC GAC -366 | Sequence encoding for the extracellular domain of CD99 |

TABLE I-continued

| | | |
|---|---|---|
| SEQ ID NO: 23 | 50-G D D F D L G D A V V D G E N D D P R P P N P P K-74 | Epitope: amino acids 50-74 of the extracellular domain of CD99 |
| SEQ ID NO: 24 | 5'-CCAGCCGGCCATGGCCGAGGTG-3' | For Primer for scFvC7 VH |
| SEQ ID NO: 25 | 5'-GTCACCGTGTCGAGAGGCGGTGGOGGATCG-3' | Rev Primer for scFvC7 VH |
| SEQ ID NO: 26 | 5'-CGATCCGCCACCGCCTCTCGACACGGTGAC-3' | For Primer for scFvC7 VL |
| SEQ ID NO: 27 | 5'-ATCGAATTCCTAGCCTAGGACGGTCAG-3' | Rev Primer for scFvC7 VL |
| SEQ ID NO: 28 | 5'-GGAACGGATCCGATGGTGGTTTCGAT-3' | For Primer CD99BamHI |
| SEQ ID NO: 29 | 5'-GGCTGGAATTCCTAGTCGGCCTCTTCCC-3' | Rev Primer CD99_EcoRI |
| SEQ ID NO: 30 | 5'-GTCGCGGATCCGATGATGGTTTC-3' | For Primer AGM_CD99_BamHI |
| SEQ ID NO: 31 | 5'-ATCACGAATTCCTAGTCCGCCTCCTCCC-3' | Rev Primer AGM_CD99_BamHI |
| SEQ ID NO: 32 | 5'-GGCGCGGATCCGACGACTTCAACCT-3' | For Primer mmCD99BamHI |
| SEQ ID NO: 33 | 5'-ACCACGAATTCCTACAAGCCCTGGGGCGT-3' | Rev Primer mmCD99EcoRI |
| SEQ ID NO: 34 | 1-<br>EVQLVESGGGLVRPGGSLRLSCAASGFTFSSYAMSW<br>VRQAPGKGLEWVSAISGSGGSTYYADSVKGRFTISRD<br>NSKNTLYLQMNSLRAEDTAVYYCAKSHKRFDYWGQG<br>TLVTVSRASTKGPSVFPLAPCSRSTSESTAALGCLVKD<br>YFPEPVTVSWNSGALTSGVHTFPAVLQSSGLYSLSSV<br>VTVPSSSLGTKTYTCNVDHKPSNTKVDKRVESKYGPP<br>CPSCPAPEFLGGPSVFLFPPKPKDTLMISRTPEVTCVV<br>VDVSQEDPEVQFNWYVDGVEVHNAKTKPREEQFNST<br>YRVVSVLTVLHQDWLNGKEYKCKVSNKGLPSSIEKTIS<br>KAKGQPREPQVYTLPPSQEEMTKNQVSLTCLVKGFY<br>PSDIAVEWESNGQPENNYKTTPPVLDSDGSFFLYSRL<br>TVDKSRWQEGNVFSCSVMHEALHNHYTQKSLSLSLG<br>K-443 | Amino acid sequence of the entire heavy chain of IgG4 |
| SEQ ID NO: 35 | 1-<br>SSELTQDPAVSVALGQTVRITCQGDSLRSYYASWYQ<br>QKPGQAPVLVIYGKNNRPSGIPDRFSGSSSGNTASLTI<br>TGAQAEDEADYYCNSSFPRTSSVVFGGGTKLTVLGQ<br>PKANPTVTLFPPSSEELQANKATLVCLISDFYPGAVTV<br>AWKADGSPVKAGVETTKPSKQSNNKYAASSYLSLTPE<br>QWKSHRSYSCQVTHEGSTVEKTVAPTECS-214 | Amino acid sequence of the entire light chain of IgG4 |
| SEQ ID NO: 36 | 1-GAA GTG CAG CTG GTT GAG TCT GGC GGA GGA<br>CTC GTT AGA CCT GGC GGA AGC CTG AGA CTG<br>TCT TGT GCC GCC AGC GGC TTC ACC TTT AGC<br>AGC TAC GCC ATG AGC TGG GTC CGA CAG GCT<br>CCT GGC AAA GGC CTT GAA TGG GTG TCC GCC<br>ATC TCT GGC TCT GGC GGC AGC ACA TAT TAC<br>GCC GAC TCT GTG AAG GGC AGA TTC ACC ATC<br>AGC CGG GAC AAC AGC AAG AAC ACC CTG TAC<br>CTG CAG ATG AAC AGC CTG AGA GCC GAG GAC<br>ACC GCC GTG TACT ACT GTG CCA AGA GCC ACA<br>AGA GAT TCG ACT ACT GGG GCC AGG GCA CCC<br>TGG TCA CAG TGT CTA GAG CCT CTA CAA AGG<br>GCC CCA GCG TGT TCC CTC TGG CTC CTT GTA<br>GCA GAA GCA CCA GCG AGT CTA CAG CCG CTC<br>TGG GCT GTC TGG TCA AGG ACT ACT TTC CCG<br>AGC CTG TGA CCG TGT CCT GGA ATA GCG GAG<br>CAC TGA CAA GCG GOG TGC ACA CCT TTC CAG<br>CTG TGC TGC AAA GCA GCG GCC TGT ACT CTC<br>TGA GCA GCG TCG TGA CAG TGC CTA GCA GCT<br>CTC TGG GCA CCA AGA CCT ACA CCT GTA ATG<br>TGG ACC ACA AGC CTA GCA ACA CCA AGG TGG<br>ACA AGC GCG TGG AAT CTA AGT ACG GCC CTC | Nucleotide sequence of the entire heavy chain of IgG4 |

TABLE I-continued

| | | |
|---|---|---|
| | CTT GTC CTA GCT GCC CCG CTC CTG AAT TTC<br>TCG GOG GAC CTT CCG TGT TCC TGT TTC CTC<br>CAA AGC CTA AGG ACA CCC TGA TGA TCA GCA<br>GAA CCC CTG AAG TGA CCT GCG TGG TGG TGG<br>ACG TGT CCC AAG AGG ATC CTG AGG TGC AGT<br>TCA ATT GGT ACG TGG ACG GCG TGG AAG TGC<br>ACA ACG CCA AGA CCA AGC CTA GAG AGG AAC<br>AGT TCA ACA GCA CCT ACA GAG TGG TGT CCG<br>TGC TGA CCG TGC TGC ACC AGG ATT GGC TGA<br>ACG GCA AAG AGT ACA AGT GCA AGG TGT CCA<br>ACA AGG GCC TGC CAA GCA GCA TCG AGA AAA<br>CCA TCA GCA AGG CCA AGG GCC AGC CTA GGG<br>AAC CCC AGG TTT ACA CAC TGC CTC CAA GCC<br>AAG AGG AAA TGA CCA AGA ACC AGG TGT CCC<br>TGA CCT GCC TCG TGA AGG GCT TCT ACC CTT<br>CCG ATA TCG CCG TGG AAT GGG AGA GCA ATG<br>GCC AGC CAG AGA ACA ACT ACA AGA CAA CCC<br>CTC CTG TGC TGG ACA GCG ACG GCT CAT TCT<br>TCC TGT ACA GCA GAC TGA CCG TGG ACA AGA<br>GCA GAT GGC AAG AGG GCA ACG TGTT CAG CTG<br>CAG CGT GAT GCA CGA GGC CCT GCA CAA CCA<br>CTA CAC CCA GAA GTC TCT GAG CCT GAG CCT<br>GGG CAA ATG A-1332 | |
| SEQ ID NO: 37 | 1-TCT<br>AGTGAACTGACCCAGGATCCAGCCGTGTCTGTGGC<br>TCTGGGCCAGACAGTGCGGATTACCTGTCAGGGCG<br>ATAGCCTGAGAAGCTACTACGCCAGCTGGTATCAG<br>CAGAAGCCTGGACAGGCTCCCGTGCTGGTCATCTA<br>CGGCAAGAACAACAGACCCAGCGGCATCCCCGATA<br>GATTCAGCGGCTCTAGCTCTGGCAATACCGCCAGC<br>CTGACAATCACTGGCGCCCAGGCTGAAGATGAGGC<br>CGACTACTACTGCAACAGCAGCTTCCCCAGAACCA<br>GCAGCGTGGTGTTTGGCGGCGGAACAAAGCTGACA<br>GTGCTGGGCCAGCCTAAGGCCAATCCTACCGTGAC<br>ACTGTTCCCTCCAAGCAGCGAAGAACTGCAGGCCA<br>ACAAGGCCACACTCGTGTGCCTGATCAGCGACTTTT<br>ATCCTGGCGCCGTGACCGTGGCCTGGAAGGCTGAT<br>GGATCTCCTGTGAAAGCCGGCGTGGAAACCACCAA<br>GCCTAGCAAGCAGAGCAACAACAAATACGCCGCCA<br>GCAGCTACCTGAGCCTGACACCTGAGCAGTGGAAG<br>TCCCACAGATCCTACAGCTGCCAAGTGACCCACGA<br>GGGCAGCACCGTGGAAAAAACAGTGGCCCCTACCG<br>AGTGCAGCTGA-645 | Nucleotide sequence of the entire light chain of IgG4 |
| SEQ ID NO 38 | 1-<br>EVQLVESGGGLVRPGGSLRLSCAASGFTFSSYAMSW<br>VRQAPGKGLEWVSAISGSGGSTYYADSVKGRFTISRD<br>NSKNTLYLQMNSLRAEDTAVYYCAKSHKRFDYWGQG<br>TLVTVSRASTKGPSVFPLAPSSKSTSGGTAALGCLVK<br>DYFPEPVTVSWNSGALTSGVHTFPAVLQSSGLYSLSS<br>VVTVPSSSLGTQTYICNVNHKPSNTKVDKKVEPKSCD<br>KTHTCPPCPAPELLGGPSVFLFPPKPKDTLMISRTPEV<br>TCVVVDVSHEDPEVKFNWYVDGVEVHNAKTKPREEQ<br>YNSTYRVVSVLTVLHQDWLNGKEYKCKVSNKALPAPI<br>EKTISKAKGQPREPQVYTLPPSRDELTKNQVSLTCLVK<br>GFYPSDIAVEWESNGQPENNYKTTPPVLDSDGSFFLY<br>SKLTVDKSRWQQGNVFSCSVMHEALHNHYTQKSLSL<br>SPGK-446 | Amino acid sequence of the entire heavy chain of IgG1 |
| SEQ ID NO 39 | 1-<br>SSELTQDPAVSVALGQTVRITCQGDSLRSYYASWYQ<br>QKPGQAPVLVIYGKNNRPSGIPDRFSGSSSGNTASLTI<br>TGAQAEDEADYYCNSSFPRTSSVVFGGGTKLTVLGQ<br>PKANPTVTLFPPSSEELQANKATLVCLISDFYPGAVTV<br>AWKADGSPVKAGVETTKPSKQSNNKYAASSYLSLTPE<br>QWKSHRSYSCQVTHEGSTVEKTVAPTECS-214 | Amino acid sequence of the entire light chain of IgG1 |
| SEQ ID NO 40 | 1-<br>GAAGTGCAGCTGGTTGAGTCTGGCGGAGGACTCGT<br>TAGACCTGGCGGAAGCCTGAGACTGTCTTGTGCCG<br>CCAGCGGCTTCACCTTTAGCAGCTACGCCATGAGC<br>TGGGTCCGACAGGCTCCTGGCAAAGGCCTTGAATG<br>GGTGTCCGCCATCTCTGGCTCTGGCGGCAGCACAT<br>ATTACGCCGACTCTGTGAAGGGCAGATTCACCATCA<br>GCCGGGACAACAGCAAGAACACCCTGTACCTGCAG<br>ATGAACAGCCTGAGAGCCGAGGACACCGCCGTGTA<br>CTACTGTGCCAAGAGCCACAAGAGATTCGACTACTG<br>GGGCCAGGGCACCCTGGTCACAGTGTCTAGAGCCA<br>GCACCAAGGGCCCTTCCGTGTTTCCACTGGCCCCC | Nucleotide sequence of the entire heavy chain of IgG1 |

TABLE I-continued

| | | |
|---|---|---|
| | TCCTCTAAATCCACATCTGGCGGCACCGCCGCCCT GGGCTGTCTGGTGAAGGACTACTTCCCAGAGCCTG TGACAGTGTCCTGGAACTCTGGCGCCCTGACATCC GGCGTGCACACATTTCCAGCCGTGCTGCAGAGCTC CGGCCTGTACAGCCTGTCTAGCGTGGTGACAGTGC CCTCCTCTAGCCTGGGCACACAGACCTATATCTGCA ACGTGAATCACAAGCCAAGCAATACCAAGGTGGAC AAGAAGGTGGAGCCCAAGTCCTGTGATAAGACACA CACCTGCCCCCCTTGTCCTGCTCCCGAGCTGCTGG GCGGCCCTAGCGTGTTCCTGTTTCCACCCAAGCCT AAGGACACCCTGATGATCTCCCGGACACCCGAGGT GACCTGCGTGGTGGTGGACGTGTCTCACGAGGATC CTGAGGTGAAGTTCAACTGGTATGTGGATGGCGTG GAGGTGCACAATGCCAAGACCAAGCCCAGAGAGGA GCAGTACAACTCTACATATAGGGTGGTGAGCGTGCT GACCGTGCTGCACCAGGACTGGCTGAACGGCAAGG AGTATAAGTGCAAGGTGTCCAATAAGGCCCTGCCC GCCCCCATCGAGAAGACAATCAGCAAGGCCAAGGG CCAGCCTCGGGAGCCACAGGTGTACACCCTGCCTC CATCCAGAGACGAGCTGACAAAGAACCAGGTGTCT CTGACATGTCTGGTGAAGGGCTTCTATCCTAGCGAT ATCGCCGTGGAGTGGGAGTCCAATGGCCAGCCAGA GAACAATTACAAGACCACACCCCCTGTGCTGGACTC CGATGGCTCCTTCTTTCTGTATTCCAAGCTGACCGT GGATAAGTCTCGGTGGCAGCAGGGCAACGTGTTCA GCTGTTCCGTGATGCACGAAGCCCTGCATAATCACT ATACTCAGAAATCCCTGTCCCTGTCACCTGGAAAG- 1338 | |
| SEQ ID NO 41 | 1- TCTAGTGAACTGACCCAGGATCCAGCCGTGTCTGT GGCTCTGGGCCAGACAGTGCGGATTACCTGTCAGG GCGATAGCCTGAGAAGCTACTACGCCAGCTGGTAT CAGCAGAAGCCTGGACAGGCTCCCGTGCTGGTCAT CTACGGCAAGAACAACAGACCCAGCGGCATCCCCG ATAGATTCAGCGGCTCTAGCTCTGGCAATACCGCCA GCCTGACAATCACTGGCGCCCAGGCTGAAGATGAG GCCGACTACTACTGCAACAGCAGCTTCCCCAGAAC CAGCAGCGTGGTGTTTGGCGGCGGAACAAAGCTGA CAGTGCTGGGCCAGCCTAAGGCCAATCCTACCGTG ACACTGTTCCCTCCAAGCAGCGAAGAACTGCAGGC CAACAAGGCCACACTCGTGTGCCTGATCAGCGACT TTTATCCTGGCGCCGTGACCGTGGCCTGGAAGGCT GATGGATCTCCTGTGAAAGCCGGCGTGGAAACCAC CAAGCCTAGCAAGCAGAGCAACAACAAATACGCCG CCAGCAGCTACCTGAGCCTGACACCTGAGCAGTGG AAGTCCCACAGATCCTACAGCTGCCAAGTGACCCA CGAGGGCAGCACCGTGGAAAAAACAGTGGCCCCTA CCGAGTGCAGC-642 | Nucleotide sequence of the entire light chain of IgG1 |
| SEQ ID NO 42 | EVQLVESGGGLVRPGGSLRLSCAASGFTFSSYAMSW VRQAPGKGLEWVSAISGSGGSTYYADSVKGRFTISRD NSKNTLYLQMNSLRAEDTAVYYCAKSHKRFDYWGQG TLVTVSRASTKGPSVFPLAPCSRSTSESTAALGCLVKD YFPEPVTVSWNSGALTSGVHTFPAVLQSSGLYSLSSV VTVPSSSLGTKTYTCNVDHKPSNTKVDKRVESKYGPP CPPCPAPEFLGGPSVFLFPPKPKDTLMISRTPEVTCVV VDVSQEDPEVQFNWYVDGVEVHNAKTKPREEQFNST YRVVSVLTVLHQDWLNGKEYKCKVSNKGLPSSIEKTIS KAKGQPREPQVYTLPPSQEEMTKNQVSLTCLVKGFY PSDIAVEWESNGQPENNYKTTPPVLDSDGSFFLYSRL TVDKSRWQEGNVFSCSVMHEALHNHYTQKSLSLSLG K | Amino acid sequence of the entire heavy chain of IgG4 mutated into S228P |

In a further aspect of the invention, the antibody complex or the composition as described above are used individually or in combination with other conventional therapeutic treatments, i.e. with other chemotherapeutic agents and/or surgery and/or immunotherapy and/or radiotherapy and/or targeted therapy.

Chemotherapeutic agents that may be used in combination are selected from among: cytarabine, daunorubicin, idarubicin, azacytidine, decitabine, doxorubicin and combinations thereof. Targeted drugs that may be used in combination are selected from among: protein-kinase and tyrosine-kinase inhibitors and FLT3 inhibitors, including midostaurin and Imatinib, inhibitors of the enzyme isocitrate dehydrogenase-1 or 2 (IDH2), including enasidenib and other epigenetic drugs; Bcl-2 inhibitors. Antibodies and immunotherapeutic agents that may be used in combination are selected from among: antibodies against CD33, CD44, CD37, CD123, immunoconjugates (ADCs), BiTe, DARTs, CAR-T cells, TCR-T cells, immune checkpoint inhibitors and vaccines.

In a further aspect of the invention, the antibody complex or composition as described above is used for diagnostic purposes in order to identify and distinguish tumour cells, preferably leukaemia cells, preferably leukaemia cells that overexpress CD99, from those of other types of tumours or normal cells. More preferably, the typing of tumour cells takes place by means of cytofluorometric or immunohistochemical studies or by immunofluorescence and molecular biology in order to determine messenger RNA expression for CD99.

According to a specific embodiment of the present invention, the antibody complex or the composition as described above is used to deliver the following into tumour cells, preferably into leukaemia cells expressing CD99: cytotoxic compounds, preferably with an anti-tumour action, which include agents from the calicheamicin class, microtubule inhibitors such as DM1, antimitotics such as monomethyl auristatin E (MMAE) and the like.

In fact, the antibody complex of the present invention can be conjugated with cytotoxic compounds, for example metals, toxins of microbial or plant origin, radioisotopes, enzymes and compounds generally used for that purpose.

The antibody complex, preferably the multivalent, more preferably bivalent (diabody), trivalent (triabody) or quadrivalent (tetrabody) scFvs, or the IgG antibody forms, preferably the classes IgG1 and/or IgG4, can preferably be modified with the addition of PEG to increase the retention time in the bloodstream in a person who receives said antibody complex.

Alternatively, it can be conjugated with a marker/tracer that can be detected, for example, with imaging techniques. Alternatively, it can be immobilized on a solid medium and/or conjugated with a heterologous compound.

According to one embodiment of the invention, the antibody complex as described in detail above can be bi-specific or multi-specific reactive with one or more further antigens, preferably antigens known as targets for therapies against cancer.

According to a preferred embodiment of the invention, the antibody complex as described in detail above can also be used in the production of T lymphocytes with chimeric antigen receptors (CAR-T cells) directed against tumour cells expressing CD99.

The invention also relates to an immunodiagnostic kit for the recognition of the human protein CD99, in particular the extracellular domain of CD99, preferably the epitope 50-74 comprising the antibody complex as described in detail above, preferably comprising said multivalent, more preferably bivalent (diabody), trivalent (triabody), or quadrivalent (tetrabody) scFvs, or the IgG antibody forms, preferably the classes IgG1 and/or IgG4. Said immunodiagnostic kit is preferably used for tumour diagnosis, preferably to diagnose pathologies characterized by the expression of CD99, preferably overexpression of CD99, said pathologies preferably being selected from among: leukaemias, myelodysplastic syndromes, and solid tumours expressing CD99, preferably selected from among: sarcomas, including Ewing's sarcoma and soft tissue sarcomas (synovial sarcoma, mesenchymal chondrosarcoma and rhabdomyosarcoma), gastrointestinal cancer, liver cancer, lung cancer, breast cancer, prostate cancer, pancreatic cancer, head and neck cancer, kidney cancer, testicular cancer, ovarian cancer, neuroendocrine tumours, melanoma, malignant glioma, astrocytoma and lymphomas.

The kit also comprises single-use sterile material for carrying out the diagnostic procedure.

A further aspect of the present invention relates to a method for the prevention and/or the treatment and/or the follow-up of leukaemias expressing the protein CD99, in particular of the forms of leukaemia that overexpress the protein CD99.

Said method comprises a step of administering at least one therapeutically effective dose of the antibody complex of the present invention and/or of the composition comprising said complex or of the anti-CD99 antibody of the present invention to patients who need a differential diagnosis of leukaemia or a treatment for leukaemia expressing CD99.

As used here, the term "therapeutically effective dose" refers to an amount that is sufficient to obtain the desired therapeutic result or to have an effect on undesirable symptoms, but is generally insufficient to cause adverse side effects.

The administration can be oral, intravenous, intraperitoneal, subcutaneous, pulmonary, transdermal, intramuscular, intranasal, buccal, sublingual or suppository.

EXAMPLES

C7dAbd

The C7 diabody (C7dAbd) is a dimeric derivative of scFv C7 characterized by a reduced length of the linker between the variable region of the heavy chain (VH) and the variable region of the light chain (VL) in the scFvC7, from 15 to 5 amino acids. The scFv C7 specific for the extracellular domain of the human adhesion molecule CD99 was isolated from a human synthetic phage antibody library using the CD99 antigen for panning as described in patent application WO2011058517.

Evaluation of the Affinity of C7dAbd and C71aG for the CD99 Antigen

The affinity of C7 in the scFv, dAbd, IgG4 and IgG1 formats for the extracellular domain of the CD99 antigen was evaluated by means of an ELISA method as described in Rath S et al. 1988 with small modifications, using the CD99ecd/GST antigen as the target.

The results are presented in Table II and show an apparent affinity, expressed as a dissociation constant (kd) that is similar between scFv and diabody, whereas the affinity of C7IgG4 showed to be surprisingly high and that of IgG1 instead lower. In this case the IgG4 variant shows a kd that is a good two orders of magnitude lower than that of the original scFvC7. This is surprising because several studies have reported a loss of affinity after the conversion of scFv fragments into IgG as in the case of C7IgG1, or that the IgG variants maintain the same affinity as the scFv they derive from.

TABLE II

| C7 antibody format | Affinity (kd) |
|---|---|
| scFv | $3.05 \times 10^{-7}$M |
| Diabody | $4.89 \times 10^{-7}$M |
| IgG4 | $5.86 \times 10^{-9}$M |
| IgG1 | $9.0 \times 10^{-6}$M |

Evaluation of Reactivity on Leukaemia Tumour Cells scFvC7 (i.e. the monomer scFv) was characterized for its specificity on cells expressing CD99 as described in patent application WO2011058517. The results of these studies show that scFvC7 is capable of binding specifically to Ewing's sarcoma cells and tissues whereas—according to these studies—it does not demonstrate to be reactive in other types of tumour cells expressing CD99.

Unexpectedly, in a cytofluorometry analysis of a panel of lines of acute lymphoblastic leukaemia (T-ALL), the same C7 antibody in the diabody format having an affinity for CD99 similar to scFvC7 showed to be reactive in 9/9 lines tested including the ones that were negative to binding with scFv (FIG. 1A-L).

The fluorescence intensity levels (mean fluorescence intensity, MFI) vary according to the line tested.

This is an unexpected result, given that scFvC7 and C7dAbd share the same VH and VL sequence and demonstrate a similar affinity for CD99.

Similar results were obtained in a fluorescence microscopy analysis where C7dAb showed to be reactive with all the cell lines of T-ALL analysed (FIG. 2).

The cytofluorometric analysis of the reactivity of C7dAbd for leukaemia cells was then also extended to cell lines of acute myeloid leukaemia (AML). In this case as well, the cells demonstrated to be highly positive for binding with the C7 diabody (FIG. 3).

As further confirmation of the different specificity between C7 in the scFv format and C7 in the diabody format for the leukaemia cells expressing CD99, the MOLT-16 cell line of T-ALL and the THP-1 cell line of AML were tested by cytofluorometry for reactivity to scFvC7. Both cell lines are highly positive to binding with C7dAbd (FIGS. 1G and 3A), while they demonstrated to be completely negative to binding with scFv at the same concentrations of use (FIG. 4).

The different specificities of scFv and the diabody for leukaemia cells is most probably not determined by a different affinity for the antigen, but could rather be tied to the different physicochemical and structural characteristics of the two molecules. ScFv has a smaller size (25 kDa) than the diabody (50 kDa) and only one antigen-binding site and could recognize a more accessible CD99 epitope on Ewing's sarcoma cells and which is masked in leukaemia cells, or there could be a different conformation of CD99 in Ewing's sarcoma and leukaemias.

With the aim of investigating the cell response, in particular cell death, induced by binding with the antibodies concerned, cytofluorometry assays were conducted with Annexin V and propidium iodide. A panel of 7 lines of T-ALL was treated with different concentrations of C7dAbd. The results shown in FIG. 5 show that all of the cells analysed are susceptible to cell death induced by C7dAb, albeit with different levels of intensity.

In another set of experiments, two lines of T-ALL, the highly positive ALL-SILLs and the CCRF-CEMs, which are less positive to binding with C7dAbd (FIGS. 1F and 1B, respectively) and to the induction of cell death (FIG. 5), and the THP-1 cell line of AML, which is highly positive to binding with C7dAbd (FIG. 3), were treated with C7dAbd at the fixed concentration of 100 μg/ml with different incubation times. In this case as well, all of the lines tested showed to be susceptible to treatment with the antibody, with an effectiveness that was already evident after one hour of incubation and reached a maximum after two hours (FIG. 6). The ALL-SILL cell lines and particularly the THP-1 line of AML confirmed to be highly susceptible to death induced by C7dAbd.

C7 IaG

Antibody fragments such as scFvs are characterized by a half-life in the bloodstream of several hours, whereas IgG antibodies have a half-life ranging from 7 to 21 days. Antibodies in the IgG format also show effector functions such as antibody-dependent cellular cytotoxicity (ADCC), antibody-dependent cellular phagocytosis (ADCP) and complement-dependent cytotoxicity (CDC), which depend on the presence of the constant fragment (Fc) and the binding with different receptors for Fc, which could be useful in certain therapeutic applications (Kellner C 2017).

Two IgG derivatives of scFv C7 were created, the first belonging to the subclass IgG4 and the second to the subclass IgG1.

C7IgG4 was generated by fusing the sequence of the variable region of the light chain (VL) of scFvC7 to the sequence of the constant region of the human IgG4 light chain and fusing the sequence of the variable region of the heavy chain (VH) of scFvC7 to the sequence of the constant region of the human IgG4 heavy chain.

IgG1 was generated in the same manner, but by fusing the VL and VH regions of scFvC7 to the respective constant sequences of human IgG1.

The two IgG derivatives of C7 were tested to evaluate the affinity for recombinant CD99 as shown in Table II and their apparent affinity showed to be surprisingly high for the IgG4 variant while lower for IgG1.

Although the literature has documented a loss of affinity after the conversion of scFv fragments into IgG or that the IgG variants maintain the same affinity as the scFv they derive from, the IgG4 variant described herein and tested shows a kd that is a good two orders of magnitude lower than that of the original scFvC7. C7-IgG4 and C7-IgG1 were then analysed for reactivity towards T-ALL and AML cells by means of cytofluorometry assays.

The results obtained are similar to those of C7 in the diabody format. In this case as well, in fact, IgG1s and in particular IgG4s showed to be highly reactive in the leukaemia cells (FIGS. 7 and 8). As regards C7IgG4, the reactivity in the cells of T-ALL ALL-SIL and AML THP-1 and MV4-11 remain at high levels up to the lowest investigated concentration of 6.25 μg/ml.

Cytofluorometry assays were therefore conducted with Annexin V and propidium iodide in order to analyse the therapeutic effectiveness of C7IgG4 by evaluating the induction of cell death in a panel of lines of T-ALL and AML. The cells were treated with C7IgG4 at a fixed concentration of 50 μg/ml and with different incubation times. The results shown in FIG. 9 demonstrate that all of the cells analysed are susceptible to cell death induced by C7IgG4, with an effectiveness that is already evident after one hour of incubation, but with different levels of intensity.

Similarly, IgG1 is capable of inducing the death of AML THP-1 and T-ALL CCRF-CEM cells after one hour of treatment with different antibody concentrations (FIG. 10). In particular, the THP-1 cells, which are more reactive to the dAbd, IgG4 and IgG1 bond, are particularly sensitive to the treatment, whereas the CCRF-CEM cells are more resistant.

C7IgG4S228P

The mutation into S228P (according to the EU numbering system) of the IgG4 molecule stabilizes it, preventing the Fab-arm exchange that is typically observed. For this reason, a mutated version of C7IgG4 was prepared, where said mutation is in position 228 (EU numbering system) in the hinge region, thus stabilizing the same.

The heavy chain of said mutated version of C7IgG4 has the following amino acid sequence, SEQ ID NO. 42:

```
SEQ ID NO. 42:
EVQLVESGGGLVRPGGSLRLSCAASGFTFSSYAMSWVRQAPGKGLEWVSA

ISGSGGSTYYADSVKGRFTISRDNSKNTLYLQMNSLRAEDTAVYYCAKSH

KRFDYWGQGTLVTVSRASTKGPSVFPLAPCSRSTSESTAALGCLVKDYFP

EPVTVSWNSGALTSGVHTFPAVLQSSGLYSLSSVVTVPSSSLGTKTYTCN

VDHKPSNTKVDKRVESKYGPPCPPCPAPEFLGGPSVFLFPPKPKDTLMIS
```

-continued

```
RTPEVTCVVVDVSQEDPEVQFNWYVDGVEVHNAKTKPREEQFNSTYRVVS

VLTVLHQDWLNGKEYKCKVSNKGLPSSIEKTISKAKGQPREPQVYTLPPS

QEEMTKNQVSLTCLVKGFYPSDIAVEWESNGQPENNYKTTPPVLDSDGSF

FLYSRLTVDKSRWQEGNVFSCSVMHEALHNHYTQKSLSLSLGK.
```

The mutation consists in having substituted the naïve serine (S) with a proline (P).

Said mutant was characterized by Western Blot analysis. 5 μg of each purified C7IgG4, C7IgG4S228P and C7 IgG1 antibody were resolved on 10% SDS-PAGE under non-reducing conditions and then transferred onto a nitrocellulose membrane. The measurement was made with an anti-C7 polyclonal antibody and then with an anti-rabbit HRP conjugate. The bands of the halved antibodies are highlighted by circles in FIG. 15. From the photographs it is evident that the incorporation of the S228P mutation abolishes the formations of the halved antibodies in C7 IgG4 (highlighted in the circle), confirming the stabilization induced by the mutation.

Study on Internalization of the C7 Diabody and C7IgG

Studies were conducted by confocal microscopy in order to evaluate whether C7dAbd is capable of internalizing after binding to CD99 on the cell surface. The experiments were conducted on T-ALL and AML cells and show the ability of C7dAbd to penetrate into the cell (FIG. 11). In particular, the kinetics and the rate of internalization reflect the kinetics and the rate of cell death induced by C7dAbd (FIG. 6). In THP-1 cells that die quickly and on a massive scale after treatment with C7dAbd, the signal is already completely internal after 30 minutes, whereas in the CCRF-CEM cells, which have a slower kinetics and a lower rate of cell death, the signal is found inside some cells after 1 hour of incubation. This result is useful for understanding the mechanism of action of the antibody and also enables the use of C7dAbd in applications that require internalization of the antibody, as in the case of antibody-drug conjugates (ADCs).

The C7dAbd diabody and internalization thereof was also verified in the leukaemia cell line MOLM13, characterized by a FLT3-ITD mutation. FIG. 16, merge panels, shows how the totality of cells visible in the field have internalized the C7dAbd diabody. The ability of the same MOLM13 line to internalize IgG4 was demonstrated, again by confocal analysis, as shown by the photographs in FIG. 17.

Ex Vivo Test

Spinal cord cells were obtained from a patient and the same were reacted with C7dAbd-FITC (50 μg/ml) or C7IgG4S228P-FITC (25 μg/ml). After the treatment, a cytofluorometric analysis was conducted.

FIG. 18 shows the results obtained on cells from an ALL patient. The cells bind the diabody and IgG4 (S228P) according to the present invention, with a higher binding affinity for IgG4, as shown by the graph of panel (A), which shows the MFI (mean fluorescence intensity). The binding % is almost total for both the diabody and IgG4, as shown in (B). As a result of the binding, and the ensuing internalization, in 4 hours of incubation the % of live cells, evaluated as Annexin V and PI negative, is minimal in the presence of the diabody and in any case less than 10% in the presence of IgG4, panel (C).

As confirmation that the diabody and IgG4 exert their proapoptotic effect on cells from the spinal cord of the ALL patient, the confocal analyses, exemplified in the photographs in FIG. 19, show an internalization that is nearly complete.

FIG. 20 shows the results obtained on cells from an AML patient bearing the FLT3-ITD mutation. These cells, too, bind the diabody and IgG4 (S228P) according to the present invention, with a higher binding affinity for IgG4, as shown by the graph in panel (A), which shows the MFI (mean fluorescence intensity). The binding % is almost total for both the diabody and IgG4, as shown in (B). As a result of the binding, and the ensuing internalization, in 4 hours of incubation the % of live cells, evaluated as Annexin V and PI negative, is about 12% in the presence of the diabody and reaches 40% in the presence of IgG4, panel (C).

The percentages indicate the specificity of the antibody according to the present invention in binding and inducing apoptosis only in leukaemia cells.

In cells from the AML patient as well, the internalization of the diabody and of IgG4 is nearly complete (data not shown).

CD34+ cells from the bone marrow of the same AML patient were then isolated. The same cells were incubated with the diabody for 2 hours and a cytofluorometric analysis was then conducted. The fluorescent marking of the diabody shows that about 40% of the CD34+ cells are fluorescent. By means of an Annexin V+PI assay it was shown that a comparable % of cells undergoes apoptosis (FIG. 21). The confocal analysis shows that in this situation as well the positive cells internalize the diabody (FIG. 21A). The result is particularly significant in that it shows that the diabody according to the present invention, in a mixed cell population, is capable of binding only 40% of the cells, which are likely to be leukaemia cells, and of killing a similar %.

The assay was repeated, exposing the CD34+ cells to IgG4 (S228P), and similar results were obtained (FIG. 22A, B, C).

The same CD34+ cells were then obtained from the bone marrow of a healthy donor and the cells were incubated with IgG4 for 2 hours, similarly to what was done on CD34+ cells from the AML patient. The results are shown in FIG. 23 and they demonstrate a weak binding ability (confocal microscopy, C and cytofluorometry, A). A weak binding ability is associated with an induction of apoptosis (B) that is almost zero.

Finally, the diabody and C7IgG4S228P were tested on peripheral blood cells from a healthy donor. The results of the cytofluorometric analysis, shown in FIG. 24, demonstrate that the cells have a binding affinity, albeit a weak one, above all towards the population of lymphocytes, which is not associated, however, with an ability to induce apoptosis (FIG. 25).

Comparison of IgG4 wt IgG4 (S228P)

The reactivity towards CD99, ability to internalize and induction of apoptosis, evaluated in MOLM13 AML cells with the Annexin V+PI assay, are shown in FIG. 26. The data obtained show that C7IgG4 wt and C7IgG4 S228P recognize CD99 with a similar affinity, are both well internalized in AML MOLM-13 cells and are capable of inducing the death of AML cells to a similar degree.

Selection of Species Relevant for the Evaluation of the Preclinical Safety of C7dAbd In the process of developing a new biotherapeutic agent and in the design of preclinical studies aimed at establishing its safety, the selection of the relevant species is of fundamental importance. As stated in the "CHMP Note for guidance on Preclinical Safety Evaluation of Biotechnology-Derived Pharmaceuticals (ICH S6) (CHMP/ICH/302/95)", a relevant species is one in which the test material is pharmacologically active due to the expression of the receptor or an epitope in the case of monoclonal antibodies.

The adhesion molecule CD99 is a type I transmembrane protein which is highly glycosylated, small (32 kDa in humans), encoded by the MIC2 gene and it does not belong to any known family of proteins. CD99 has a unique structure and is not related to any other molecule in the human genome, with the exception of the paralog similar to CD99 (CD99L2), which can be originated from a common ancestral gene. The MIC2 gene is in the pseudoautosomal region of the sex chromosomes, X (Xp22.33-Xpter) and Y (Yp11-Ypter). The gene has a length of 50 kb and contains 10 small exons. The search for CD99 homologs through cross-hybridization experiments with cDNA or single-exon probes has had success only in primates, indicating a high level of divergence of this gene over the course of evolution. In humans the MIC2 gene encodes two distinct proteins following an alternative splicing process: a full-length or type 1 CD99 (CD99 wt) and a truncated form of said CD99 type II (CD99sh) with a shorter cytoplasmatic domain. Both isoforms are preserved in primates. The D4 gene situated in the C7-D1 region of chromosome 4 was identified as a mouse ortholog of human CD99. An analysis of the genomic organization revealed that the gene contains 10 putative exons, whereas the cDNA consists of nine exons encoding for a protein that has 46% identity with human CD99. The molecules of rodent CD99 have a short cytoplasmatic domain, as is found in the human CD99 type II isoform. Mouse CD99 shows biochemical characteristics, a functional homology and models of expression that are similar to those of human CD99.

With the aim of identifying the species most relevant for preclinical studies of C7dAbd, account was taken not only of data from the scientific literature and analyses of the homology of the target antigen in public sequence databases, but also experimental data on the recognition of the target epitope in three different species (two primates and one rodent).

With the aim of finding a species relevant for non-clinical studies of C7dAbd, the homology of the CD99 sequence and scFvC7 epitope across different species was analysed. Finally, the extracellular domain CD99 of the species selected for the analysis of the C7dAbd binding affinity was cloned and purified.

Sequence Homology of CD99 in Different Species

The homology between human CD99 and the CD99 of different species was studied using the program NCBI BLAST (www.ncbi.nlm.nih.gov/BLAST/); the analysis was focused on the cynomolgus monkey (*Macaca fascicularis*) and the African green monkey (*Chlorocebus aethiops*), which are two species of non-human primates (NHPs) widely used in preclinical studies on monoclonal antibodies and the homology of mouse CD99. The sequence alignments (Table III and FIG. 12) showed that human CD99 shares a 55-93% homology with the homologs of the species analysed, with the highest values (92-93%) for the proteins of primates. Furthermore, the entire region of the epitope is well conserved in primates but not in the mouse (FIG. 12B).

TABLE III

Human amino acid sequence of CD99 compared with that of other species.

| Species | Common name | Accession number | Identities | Positives | Gaps |
|---|---|---|---|---|---|
| *Homo sapiens* | human | CAG29282.1 | — | — | — |
| *Macaca fascicularis* | Cynomolgus monkey | XP_005592936.1 | 152/167 (91%) | 152/167 (91%) | 3/167 (1%) |
| *Chlorocebus aethiops* | African green monkey | AAB58504.1 | 148/161 (92%) | 150/161 (93%) | 0/161 (0%) |
| *Mus musculus* | mouse | AAP91687.1 | 65/142 (46%) | 79/142 (55%) | 14/142 (9%) |

In determining the cross-reactivity and binding power of C7dAbd with respect to the CD99 of the species analysed, the extracellular domains of cynomolgus monkey, African green monkey and mouse CD99 were cloned from the respective genes and the recombinant proteins expressed in *E. coli* and purified. After purification, the proteins were used as target antigens in ELISA assays in order to evaluate the reactivity of C7dAbd. The results are shown in FIG. 13 and they demonstrate that the antibody is capable of reacting with the CD99 of all three species analysed, but with different affinities. In particular, C7dAbd recognizes human CD99 and the CD99 of the two primates with a very similar affinity, much higher than that observed for mouse CD99.

In conclusion, the results obtained on the cross-reactivity of C7dAbd, the sequence homologies and the available information strongly suggest that NHPs such as the cynomolgus monkey or African green monkey can be considered as the most relevant species for the preclinical determination of the safety of C7dAbd.

Preparation of the Gene Constructs of C7dAbd, C7IgG4 and C7IgG1.

C7dAbd. The gene construct of C7dAbd was created starting from that of scFv C7, by reducing the length of the linker between VH and VL from 15 to 5 amino acids. The primers used for cloning are listed in Table 1. In a first PCR step the VH sequence of scFvC7 was amplified using the primer pair SEQ ID NO: 24 and SEQ ID NO: 25, introducing a cut site for the enzyme NcoI at the 5' end of the amplified product; whereas the VL sequence was amplified with the primer pair SEQ ID NO: 26 and SEQ ID NO: 27 (the NcoI, NdeI and EcoRI restriction sites are in italics. The stop codon is underlined), the latter containing a stop codon followed by a cut site for the enzyme EcoRI. The SEQ ID NO: 25 and SEQ ID NO: 26 primers contain a mutually overlapping region corresponding to the 5 residues composing the linker between VH and VL; in this manner the amplified VH and VL sequences contain this overlapping region, which can be extended in a PCR reaction. The amplified VH and VL sequences were used as a template and joined in a second PCR using the primers SEQ ID No 24 and SEQ ID No 27 (for amplification). The amplified products were digested, together with the pET22b(+) vector (Merck Millipore), with the NcoI and EcoRI enzymes (New England Biolabs, Ipswich, MA, USA) at 37° C. for 3 hours. The digested products were purified and ligated together with T4 DNA ligase (Promega, Madison, WI, USA) overnight at 4° C. The ligation mixture was transformed in the *E. coli* BL21(DE3) strain ((F-ompT hsdSB(rB-mB-) gal dcm (DE3)) to enable the expression and purification of the protein. The positive clones were analysed to verify the correct insertion of the construct by sequencing.

C7IgG4 and C7IgG1. The genes encoding for the light chain and heavy chain of C7IgG4 and C7IgG1 were synthesised by GenScript (Piscataway, NJ, USA) and inserted into the pcDNA3.1(−) vector (Invitrogen, Carlsbad, CA, USA). In particular, the gene constructs of the light chains contain the VL sequence of scFvC7 fused to the sequence of the constant region of human IgG4 (in the case of C7IgG4) or IgG1 (in the case of C7IgG1), whereas the gene constructs of the heavy chains contain the VH sequence of scFvC7 fused to the sequence of the constant region of human IgG4 (in the case of C7IgG4) or IgG1 (in the case of C7IgG1).

Purification of C7dAbd

Purification of C7dAbd was performed as described in Moricoli D, 2015. Briefly, cells of *E. coli* BL21(DE3) containing the gene construct of C7dAbd, were cultured overnight at 37° C. under stirring in LB medium supplemented with ampicillin at the concentration of 100 μg/ml. The culture was then inoculated into a synthetic medium supplemented with 50 μg/ml ampicillin in a 20 L bioreactor (Biostat C, Sartorius). The bacteria were cultured in the bioreactor until reaching an O.D.600 of 10. The expression of C7dAbd was then induced by adding 1 mM isopropyl-β-D-thiogalactopyranoside (IPTG) and 40 mM sucrose to the culture. Three hours after induction the cell culture was collected by centrifugation. The cell pellet was then resuspended in a lysis buffer (L buffer) containing: 30 mM sucrose, 2 mM EDTA, 1 mM DTT and 20 mM of a phosphate buffer at pH 7.0; and subjected to cell destruction by means of a homogenizer (GEA Niro Soavi) at 680 bar and then centrifuged at 8000 rpm for 60 min at 4° C. The supernatant was used for the purification of C7dAbd by means of an automatic chromatography system, AKTA explorer 100 (GE-Healthcare). The first chromatography step consists in a cation exchange with an SP sepharose fast flow resin (GE Healthcare) balanced with L buffer. After loading of the sample and subsequent washes, the protein was eluted with L buffer to which 0.5M NaCl was added. The second and last purification step provides for a chromatographic analysis of affinity with the recombinant protein A using the rProtein Sepharose fast flow resin (GE Healthcare) balanced with PBS (saline phosphate buffer). The eluate of the SP resin was loaded into a column and after washes the C7dAbd was eluted with a buffer containing 0.1 M Sodium citrate pH 3 and 0.05% (v/v) glycerol and immediately neutralized to pH 7 with 1 M Tris. Finally, C7dAbd was filtered using the Sartobind Q device (Sartorius) and 0.22 μm filters and stored at −80° C. in aliquots. The protein concentration was determined by absorption at 280 nm and purity by SDS-PAGE.

Production of C7IgG4 and C7IgG1

For the production of C7IgG4 and C7IgG1, plasmids containing the light chain and heavy chain of C7IgG4 or C7IgG1 were co-transfected into Expi293F™ cells cultured in serum-free Expi293™ Expression Medium (Thermo Fisher Scientific). The cells were maintained in Erlenmeyer flasks (Corning Inc.) at 37° C. with 8% $CO_2$ in an orbital shaker (VWR Scientific). The day before transfection the cells were seeded at the appropriate density in Corning Erlenmeyer flasks. On the day of transfection the DNA and ExpiFectamine™ 293 Reagent (Thermo Fisher Scientific) were mixed and added to the flasks containing the cells. 16-18 hours after transfection, ExpiFectamine™ 293 Transfection Enhancer 1 and ExpiFectamine™ 293 Transfection Enhancer 2 (Thermo Fisher Scientific) were added to every flask. The supernatants of the cell cultures containing the antibodies were collected 6 days after transfection, centrifuged, filtered and used for purification on protein A. After elution the pool was dialyzed in PBS, aliquoted and stored at −80° C. The protein concentration was determined by absorption at 280 nm and purity by SDS-PAGE.

Cloning and Purification of Human CD99ecd/GST

The extracellular domain of CD99 was amplified from the CD99ecd gene construct in pQE30Xa with the primers CD99BamHI Fw: 5'-GGAACGGATCC-GATGGTGGTTTCGAT-3' (SEQ ID NO: 28) and CD99_EcoRI Rev:5'-GGCTGGAAT-TCCTAGTCGGCCTCTTCCC-3' (SEQ ID NO: 29), introducing a cut site for the enzyme BamHI at the 5' end of the amplified product and a site for EcoRI at the 3' end. The amplified product was digested together with the vector pGEX-2T (GE Healthcare Life Sciences), which enables the gene of interest to be fused downstream of the gene for glutathione-S-transferase, with the enzymes BamHI and EcoRI (New England Biolabs, Ipswich, MA, USA) at 37° C. for 3 hours. The digested insert and vector were purified and ligated together with T4 DNA ligase (Promega, Madison, WI, USA) at 4° C. overnight. The ligation mixture was transformed in the *E. coli* BL21(DE3) strain to enable the expression and purification of the protein. The positive clones were analysed for the correct insertion of the construct by sequencing.

The *E. coli* cells containing the plasmid pGEX+CD99ecd/GST were cultured in a flask in 1 L of LB medium supplemented with 100 μg/ml ampicillin at 37° C. in an orbital shaker until an OD600 of about 0.6 was reached. At that point the protein expression was induced by adding 1 mM IPTG to the culture. Cell growth was maintained at 37° C. under shaking for an additional 3 hours, after which the cells were collected by centrifugation. The cell pellet was resuspended in 100 ml of PBS and then lysed by sonication. The cell lysate was centrifuged at 10,200 rpm for 30' at 4° C. and the supernatant was collected, filtered and loaded for the purification of CD99ecd/GST by affinity chromatography on Glutathione Sepharose 4B resin (GE Healthcare Life Sciences) previously balanced in PBS. After washing with PBS, the protein of interest was eluted with 50 mM Tris-HCl, 10 mM GSH buffer, pH 8.0. The protein concentration was determined by means of a Bradford assay and purity by SDS-PAGE. The pool was aliquoted and the aliquots maintained at −80° C.

Determination of Kd by ELISA

The binding affinity, expressed as the dissociation constant (kd) of scFv C7, C7dAbd, C7IgG4 and C7IgG1 for CD99, was determined by analysing the saturation of binding at equilibrium with a competitive ELISA assay according to the procedure described in Rath S 1988 with small variations. A first titration assay was performed by ELISA to determine the antibody concentration which determines 50% of binding to the antigen (EC50). For this purpose, 96-well plates were sensitized by distributing 500 ng/well of CD99ecd/GST diluted in 0.5M carbonate buffer, pH 9.6, and incubating ON at 4° C. After 3 washes with PBS supplemented with 0.05% V/V of Tween20, the plates were blocked with a 1% W/V solution of BSA in PBS (PBSB), pH 7.4, for 60 min. at 37° C. After washing, the plates were incubated for 1 hour at 37° C. with serial dilutions of C7 (from 200 μg/ml to 0.03 μg/ml in triplicate) diluted in PBSB and dispensed (100 μl/well). The plates were incubated at 37° C. for 90 minutes. After washing a dilution of polyclonal anti-scFv diluted 1:500 in PBSB was dispensed, 100 μl/well, and incubated for 60 minutes at 37° C. After washes a dilution of 1:1000 v/v of the detection antibody, consisting of anti-rabbit HRP in PBSB, was added in an amount of 100 μl/well. After 1 hour of incubation at 37° C. the plates were washed again and the staining solution, consisting of ABTS, was added.

The staining intensity was read at 405 nm with a microplate reader.

The subtracted results of the background were used to construct a Michaelis Menten curve with statistical software (Graphpad 4) in order to establish the value of EC50.

A competitive ELISA assay was then set up. For this purpose, a coating of CD99ecd/GST diluted in 0.5M carbonate buffer, pH 9.6, was applied at 500 ng per well and incubated ON at 4° C. After 3 washes with PBS supplemented with 0.05% V/V of Tween20 the plates were blocked with a solution of PBSB dispensed in an amount of 100 μl per well and incubated for 60 minutes at 37° C. After washes, serial dilutions of the CD99ecd/GST antigen from 400 μg/ml to 0.015 ug/ml diluted in PBSB in the presence of the antibody in the amount established by the EC50 calculated with the previous direct ELISA were plated. The scFvC7 and C7 diabody signal was determined by dispensing, in a first step, a polyclonal anti-scFv antibody generated in rabbits immunized with scFvC7 and diluted 1:500 v/v in PBSB and subsequently with an anti-rabbit HRP diluted 1:1000 v/v. The detection of C7IgG4 and C7IgG1 was carried out by dispensing an anti-human IgG HRP diluted 1:1000 v/v. After incubation and washes, the signal was highlighted by adding ABTS as a chromogenic substrate. After a reading of absorbances at 405 nm, the result was calculated with GraphPad software creating a monoexponential decay curve and defining the IC50, i.e. the amount, in molar concentration, of the inhibitor required to provide 50% inhibition of the signal.

Cell Lines

The leukaemia cell lines were cultured in RPMI-1640 (Carlo Erba) medium completed with 10% of de-complemented fetal bovine serum (FBS), 2 mM L-glutamine and 1% v/v of penicillin-streptomycin. All of the cell lines were kept in an incubator at 37° C. in a humidified atmosphere with 5% CO2.

Immunofluorescence

The cells were treated under a laminar flow hood, maintaining the conditions of sterility, and their viability was monitored under a microscope.

The cells were washed with a culture medium pre-heated to 37° C. and centrifuged for 6 minutes at 1600 rpm; the supernatant was eliminated, whereas the pellet was resuspended in 10 mL of PBS and washed in this solution 3 times. A count was then made in a haemocytometer chamber after staining with Trypan Blue, then $3.5\times10^6$ cells were collected in order to be fixed.

Fixing was carried out with 4% formaldehyde (v/v) in PBS; after centrifuging the cells were resuspended in 6 ml of this solution, bringing their concentration to $5\times10^5$ cells/ml. This suspension was seeded in a 6-well plate, 1 ml per well with a coverslip placed on the bottom. The fixing phase was maintained for 15 minutes at room temperature, the cells were subsequently washed 3 times with 3 mL of PBS. The cells were treated at room temperature for 60 minutes with a blocking solution consisting of PBS 1×, 1% W/V BSA and 0.05% W/V gelatine dissolved at 37° C. At this point the C7dAbd antibody diluted in PBS was added, 1 mL per well, and left to incubate for 90 minutes. After the incubation phase, 3 washes were carried out with 3 mL of PSB 1× per well. Subsequently, the protein A-FITC diluted 1:1000 v/v in a blocking solution was dispensed and incubated in darkness for 60 minutes. After 3 washes, DAPI diluted 1:10000 v/v in PBS 1× was added; this solution was maintained in contact with the cells for one minute; finally, the cells were washed again and subjected to microscopic analysis. The signals were visualized with a Leica DMLB fluorescence microscope equipped with a DC300F CCD digital camera.

Binding Assay by Cytofluorometry

The cells were taken from the flasks and placed in tubes with 11 mL of culture medium pre-heated to 37° C., precipitated by centrifuging for 6 minutes at 1600 rpm, the supernatant was eliminated after centrifuging; the pellet was resuspended in 3 ml of medium and a count was made in a haemocytometer chamber after staining with Trypan Blue, the cell density was then brought to $5\times10^5$ cells/ml by adding medium. Cytofluorometry tubes were prepared by dispensing 1 ml of the cell suspension per tube.

The cells were then washed twice in 4 ml of PBS 1× by centrifuging at 1600 rpm for 6 min; the supernatant was eliminated each time. Subsequently, they were resuspended in 200 μl of blocking solution consisting of PBS 1× and BSA 1% w/v; this condition was maintained for 30 minutes at room temperature. After this step, the antibody was added to the 200 μl of blocking solution that had been kept at room temperature for 60 minutes. At the end of incubation, each tube was washed twice with 4 mL of PBS 1× and subsequently centrifuged for 6 minutes at 1600 rpm, decanting the supernatant each time. Each cell pellet was resuspended in 200 μl of a solution consisting of protein A-FITC diluted 1:1000 v/v in a blocking solution; incubation was maintained for 60 minutes at room temperature. After this step the cells were washed once with 4 mL of PBS 1× and centrifuged as described above; the supernatant was removed by suction with a pump, leaving about 500 μl of washing solution in every tube. The samples were subjected to cytofluorometric analysis with FacScan (Becton Dickinson).

Evaluation of Apoptosis

Apoptosis in the leukaemia cells was evaluated by means of the Annexin V and propidium iodide test using cytofluorometry techniques. The cells were collected, counted and transferred into 50 mL test tubes and brought to a concentration of $5\times10^5$ cells/ml with RPMI medium; the cell suspension was subsequently dispensed, 1 ml per tube ($5\times10^5$ cells). After centrifuging at 1600 rpm for 6 minutes, the cells were treated with the antibody; samples were prepared in parallel and treated with a placebo. The samples were maintained in incubation for 4 hours at 37° C. At the end of incubation, the cells were centrifuged at 1200 rpm for 8 minutes, the supernatant was removed and 150 μl of Binding Buffer of the Human Annexin V FITC kit (Valter Occhiena) were added to every tube. After that, the resuspended cells were transferred into cytofluorometry tubes, to which 3 μl of Annexin V-FITC and 3 μl of propidium iodide were added; the samples were mixed thoroughly and then left to incubate in darkness for 20 minutes at room temperature. After incubation, the samples were washed with 4 ml of PBS by centrifuging at 1200 rpm for 8 minutes and decanting the supernatant, 200 μl of Binding Buffer were added to every tube and the samples were examined by cytofluorometry.

Confocal Microscopy

The cells were taken from the flasks and placed in tubes with 11 mL of culture medium pre-heated to 37° C., then precipitated by centrifuging for 6 minutes at 1600 rpm, the supernatant was eliminated after centrifuging; the pellet was resuspended in 3 ml of medium and a count was made in a haemocytometer chamber after staining with Trypan Blue, the cell density was then brought to $5\times10^5$ cells/ml by adding medium. The various conditions were prepared by dispensing 1 ml of the cell suspension per tube. The cells were then washed twice in 4 ml of PBS 1× by centrifuging at 1600 rpm for 6 min; the supernatant was eliminated each time. Subsequently, they were resuspended in 200 μl of blocking solution consisting of PBS 1× and BSA 1% w/v; this condition was maintained for 30 minutes at room temperature. After this step, the C7dAbd antibody, previously marked with FITC, was added to the 200 μl of blocking solution that had been maintained for 30 minutes, 1 hour, 2 hours and 4 hours. At the end of every incubation, each tube was washed twice with 4 mL of PBS 1× and subsequently centrifuged for 6 minutes at 1600 rpm, decanting the supernatant each time. Each cell pellet was resuspended in 200 μl and the samples were subjected to confocal analysis.

Cloning and Purification of Cynomolgus Monkey, African Green Monkey and Mouse CD99ecd/GST The extracellular domains of CD99 of the cynomolgus monkey (*Macaca fascicolaris*) and African green monkey (*Cercopithecus aethiops*) were amplified from the respective CD99ecd gene constructs in pET45b previously created from cDNA reverse transcribed from RNA of cynomolgus monkey lymphocytes or from RNA originating from the African green monkey COS-1 cell line.

Amplification was obtained for both species with the primers AGM_CD99_BamHI_Fw:5'-GTCGCGGATCC-GATGATGGTTTC-3' (SEQ ID NO 30) and AGM_CD99_EcoRI Rev: 5'-ATCACGAAT-TCCTAGTCCGCCTCCTCCC-3' (SEQ ID NO 31). The extracellular domain of mouse CD99 was amplified from a plasmid containing the CD99 gene using the primers: mmCD99BamHI Fw2: 5'-GGCGCGGATCCGACGACTT-CAACCT-3' (SEQ ID NO 32) and mmCD99EcoRI Rev: 5'-ACCACGAATTCCTACAAGCCCTGGGGCGT-3' (SEQ ID NO 33). All of the primers used introduce a cut site for the enzyme BamHI at the 5' end of the amplified product and a site for EcoRI at the 3' end. The amplified products were digested together with the vector pGEX-2T (GE Healthcare Life Sciences), which enables the gene of interest to be fused downstream of the gene for glutathione-S-transferase, with the enzymes BamHI and EcoRI (New England Biolabs, Ipswich, MA, USA) at 37° C. for 3 hours. The digested inserts and vector were purified and ligated together with T4 DNA ligase (Promega, Madison, WI, USA) a 4° C. overnight. Each ligation mixture was transformed in the *E. coli* BL21(DE3) strain so as to enable the expression and purification of the protein. The positive clones were analysed by sequencing for the correct insertion of the construct.

The purification of the three proteins took place as described for human CD99ecd/GST. The CD99ecd/GSTs of the different species were used in ELISA titration assays in order to evaluate the reactivity of C7dAbd, as described above.

The invention claimed is:

1. An isolated IgG type immunoglobulin capable of recognizing and binding an epitope of the extracellular domain of the human protein CD99, wherein said immunoglobulin comprises at least two variable regions capable of recognizing and binding an epitope of the extracellular domain of the human protein CD99 characterized by an amino acid sequence comprising SEQ ID NO: 21, said at least two variable regions each comprising:

a heavy variable chain (VH) characterized by a CDR3 comprising SEQ ID NO: 1 and a light variable chain (VL) characterized by a CDR3 comprising SEQ ID NO: 2 wherein:

(1) said VH chain comprises a CDR1 region and a CDR2 region characterized by an amino acid sequence comprising, respectively, SEQ ID NO: 3 and 4 and (2) said VL chain comprises a CDR1 region and a CDR2 region characterized by an amino acid sequence comprising, respectively, SEQ ID NO: 5 and 6.

2. The immunoglobulin according to claim 1, wherein said epitope is characterized by an amino acid sequence comprising SEQ ID NO: 23.

3. The immunoglobulin according to claim 1, wherein (1) said VH chain is characterized by an amino acid sequence comprising SEQ ID NO: 7 or sequences with an identity of at least 95%; and (2) said VL chain is characterized by an amino acid sequence comprising SEQ ID NO: 8 or sequences with an identity of at least 95%.

4. The immunoglobulin according to claim 1, wherein the immunoglobulin is an IgG4 type immunoglobulin, wherein the amino acid sequence of each heavy chain of said IgG4 comprises SEQ ID NO: 34 or sequences having an identity of at least 95%, and the amino acid sequence of each light chain of said IgG4 comprises SEQ ID NO: 35 or sequences having an identity of at least 95%, wherein SEQ ID NO: 34 comprises SEQ ID NO: 7 and SEQ ID NO: 35 comprises SEQ ID NO: 8.

5. The immunoglobulin according to claim 2, wherein the immunoglobulin is an IgG1 type immunoglobulin, wherein the amino acid sequence of each heavy chain of said IgG1 comprises SEQ ID NO: 38 or sequences having an identity of at least 95% and the amino acid sequence of each light chain of said IgG1 comprises SEQ ID NO: 39 or sequences having an identity of at least 95%, wherein SEQ ID NO: 38 comprises SEQ ID NO: 7 and SEQ ID NO: 39 comprises SEQ ID NO:8.

6. A method for treating a cancer overexpressing CD99 comprising administering an IgG type immunoglobulin according to claim 1 to a subject in need thereof.

7. A method for treating a leukaemia, comprising administering an antibody to a subject in need thereof, wherein said antibody is an IgG type immunoglobulin according to claim 1 or wherein said antibody comprises at least two variable regions capable of recognizing and binding an epitope of the extracellular domain of the human protein CD99 characterized by an amino acid sequence comprising SEQ ID NO: 21, said at least two variable regions each comprising:

a heavy chain variable region (VH) characterized by a CDR3 comprising SEQ ID NO: 1, a light chain variable region (VL) characterized by a CDR3 comprising SEQ ID NO: 2, wherein:

(1) said VH chain of the antibody comprises a CDR1 region and a CDR2 region characterized by an amino acid sequence comprising, respectively, SEQ ID NO: 3 and 4; and (2) said VL chain of the antibody comprises a CDR1 region and a CDR2 region characterized by an amino acid sequence comprising, respectively, SEQ ID NO: 5 and 6, wherein said leukaemia is characterized by leukaemia cells which express CD99.

8. The method according to claim 7, wherein said epitope is characterized by an amino acid sequence comprising SEQ ID NO: 23.

9. The method according to claim 7, wherein: (1) said VH chain of the antibody is characterized by an amino acid sequence comprising SEQ ID NO: 7 or sequences with an identity of at least 95%; and (2) said VL chain of the antibody is characterized by an amino acid sequence comprising SEQ ID NO: 8 or sequences with an identity of at least 95%.

10. The method according to claim 7, wherein said antibody is a fragment of a multivalent single-chain variable region (scFv).

11. The method according to claim 10, wherein the scFv units of said multivalent scFv are joined together by a linker characterized by an amino acid sequence comprising SEQ ID NO: 9 or sequences with an identity of at least 95%.

12. The method according to claim 10, wherein each scFv unit of said multivalent scFv is characterized by an amino acid sequence comprising SEQ ID NO: 10 or sequences with an identity of at least 95%.

13. The method according to claim 7, wherein said antibody is a diabody, or it is an IgG4 wt or IgG4 bearing the S228P mutation.

14. The method according to claim 7, in combination with further chemotherapeutic agents, selected from among: daunorubicin, idarubicin, cytarabine, azacytidine, decitabine and combinations thereof, and/or in combination with surgery and/or immunotherapy and/or radiotherapy and/or targeted therapy.

15. The method according to claim 10, wherein said scFv is selected from among: a diabody, a triabody and a tetrabody.

16. The method according to claim 13, wherein said leukaemia cells overexpress CD99.

17. The method according to claim 7, wherein leukaemia is selected from among: acute lymphoblastic leukaemia (ALL), acute myeloid leukaemia (AML), chronic lymphatic leukaemia (CLL), chronic myeloid leukaemia (CML) and myelodysplastic syndrome (MDS).

* * * * *